(12) United States Patent
Baucke et al.

(10) Patent No.: US 6,740,647 B1
(45) Date of Patent: May 25, 2004

(54) THROMBIN INHIBITORS

(75) Inventors: Dorit Baucke, Mannheim (DE); Udo Lange, Ludwigshafen (DE); Helmut Mack, Ludwigshafen (DE); Werner Seitz, Plankstadt (DE); Hans Wolfgang Höffken, Ludwigshafen (DE); Wilfried Hornberger, Neustadt (DE)

(73) Assignee: Abbott GmbH & Co., KG, Wiesbaden (DE)

( * ) Notice: Subject to any disclaimer, the term of this patent is extended or adjusted under 35 U.S.C. 154(b) by 0 days.

(21) Appl. No.: 09/582,040

(22) PCT Filed: Jan. 23, 1999

(86) PCT No.: PCT/EP98/00434

§ 371 (c)(1),
(2), (4) Date: Jun. 21, 2000

(87) PCT Pub. No.: WO99/37668

PCT Pub. Date: Jul. 29, 1999

(30) Foreign Application Priority Data

Jan. 26, 1998 (DE) .......................................... 198 02 793

(51) Int. Cl.$^7$ .................... C07D 403/12; C07D 407/12; C07D 409/12; C07D 417/12; A61P 7/02

(52) U.S. Cl. .......................... 514/210.18; 514/252.4; 514/236; 514/363; 514/365; 514/403; 514/414; 514/422; 544/238; 546/212; 548/136; 548/200; 548/265.7; 548/467; 548/517; 548/527; 548/953

(58) Field of Search ................... 514/210.18, 252.01, 514/236, 323, 365, 403, 414, 422; 544/238; 546/212; 548/136, 200, 265.7, 467, 517, 527, 953

(56) References Cited

U.S. PATENT DOCUMENTS

| 4,346,078 A | 8/1982 | Bajusz et al. ............ 424/177 |
| 4,703,036 A | 10/1987 | Bajusz et al. ............ 514/18 |
| 5,583,113 A | 12/1996 | Berry et al. ............. 514/18 |
| 5,705,487 A * | 1/1998 | Schacht et al. ........... 514/19 |
| 6,069,232 A | 5/2000 | Malikayl et al. .......... 530/331 |

FOREIGN PATENT DOCUMENTS

| DE | 31 08 810 | 5/1982 |
| EP | 118 280 | 9/1984 |
| EP | 185 390 | 6/1986 |
| EP | 195 212 | 9/1986 |
| EP | 293 881 | 12/1988 |
| EP | 362 002 | 4/1990 |
| EP | 364 344 | 4/1990 |
| EP | 410 411 | 1/1991 |
| EP | 471 651 | 2/1992 |
| EP | 479 489 | 4/1992 |
| EP | 503 203 | 9/1992 |
| EP | 504 064 | 9/1992 |
| EP | 526 877 | 2/1993 |
| EP | 530 167 | 3/1993 |
| EP | 542 525 | 5/1993 |
| EP | 589 741 | 3/1994 |
| EP | 601 459 | 6/1994 |
| EP | 672658 A1 * | 9/1995 |
| EP | 672 658 | 9/1995 |
| HU | P99/01290 | 9/1996 |
| WO | WO 92/07869 | 5/1992 |
| WO | WO 93/11152 | 6/1993 |
| WO | WO 93/15756 | 8/1993 |
| WO | WO 93/18060 | 9/1993 |
| WO | WO 94/08941 | 4/1994 |
| WO | WO 9429336 | 12/1994 |

OTHER PUBLICATIONS

Draetta, G. and Pagano, M. in "Annual Reports in Medicinal Chemistry, vol. 31", 1996, Academic Press, San Diego, p 241–246.*

Wolff, Manfred E. "Burger's Medicinal Chemistry, 5ed, Part I", John Wiley & Sons, 1995, pp. 975–977.*

Banker, G.S. et al, "Modern Pharmaceutics, 3ed.", Marcel Dekker, New York, 1996, pp. 451 and 596.*

Oleksyszyn et al. "Novel Amidine–Containing Peptidyl Phosphonates as Irreversible Inhibitors for Blood Coagulation and Realted Serine Proteases" Jour. Med. Chem. vol. 37 (1994) pp. 226–231.

Muller–Esterl et al. "Human Plasma Kininogens are identical with α–cysteine proteinase inhibitors" FEBS vol. 182 No. 2, (1985) pp. 310–314.

Kettner et al. "Synthesis of Petides of Arginine Chloromethyl Ketone. Selective Inactivation of Human Plasma Kallikrein" Biochemistry vol. 17, No. 22 (1978) pp. 4778–4782.

Kettner et al. "Inactivation of Trypsin–Like Enzymes with Peptides of Arginine Chloromethyl Ketone" Meth. Enzyme vol. 80 (1981) pp. 826–842.

Markwardt et al. "Synthetis Low Molecular Weight Inhibitors of Serum Kallikrein" Biochem. Pharm. vol. 23 (1974) pp. 2247–2256.

Roger et al. "The Chemistry of Imidates" Chem. Reviews vol. 61 (1962) pp. 179–211.

von Heinz Moser et al. "Poly(dipeptamidinium)–Salze: Definition und Methoden zur präparativen Herstellung" Helvetica Chimca Acta vol. 69 (1986) pp. 1224–1262.

(List continued on next page.)

Primary Examiner—Mukund J. Shah
Assistant Examiner—Thomas McKenzie
(74) Attorney, Agent, or Firm—Wood, Phillips, Katz, Clark & Mortimer

(57) ABSTRACT

Novel five-membered heterocyclic amidines, their preparation and use as competitive inhibitors of trypsin-like serine proteases, especially thrombin and kininogenases such as kallikrein. Pharmaceutical compositions which contain the compounds as active ingredients, and use of the compounds as thrombin inhibitors, anticoagulants and antiinflammatory agents.

14 Claims, No Drawings

OTHER PUBLICATIONS

Uray et al. "tert–Butyl Esters and Ethers of (R,R)–Tartaric Acid" Tetrahedron vol. 44 (1988) pp. 4357–4362.

Prätorius et al. Die Darstellung isoleucinverwandter L–α Aminocarbonsäuren Chem. Ber. vol. 108 (1975) pp. 3078–3091.

Prätorius et al. Die Darstellung isoleucinverwandter L–α Aminocarbonsäuren Chem. Ber. vol. 108 (1985) pp. 3078–3091.

Moskal et al. "Synthesis of aldehydes by a one–carbon homologation of ketones and aldehydes via α,β–unsaturated isocyanides" Recl. Trav. Chim–Bas, vol. 106, (1987) pp. 137–141.

Hill et al. "Preparation and resolution of Cyclopentaneglycine" Jour. Organic Chem. vol. 30 (1995) pp. 1321–1322.

Chung et al. "Comformationally Constrained Amino Acids. Synthesis and Optical Resolution of 3–Substituted Proline Derivatives" J. Org. Chem. vol. 55 (1990) pp. 270–275.

Josien et al. "Design and Synthesis of Side–Chain Conformationally Restricted Phenylalinines and their use for Structure–Activity Studies on Tachykinin NK–1 Receptor" J. Med. Chem. vol. 37 (1994) pp. 1586–1601.

Reimann et al. "Zur–Synthese von 2–(1–Tetraly)–und 2–[5–(5,6,7,8–Tetrahydro)–chino–lyl]–glycin" Arch. Pharm. vol. 310 (1977) pp. 102–109.

U. Schöllkopf et al. "Trialkylmethyl–substituierte Glycine und Pyrrol–2,4–dicarbon–säureester aus 2–Isocyanacrylsäureestern und Carganionen" Leibigs Ann. Chem. (1977) pp. 1174–1182.

* cited by examiner

THROMBIN INHIBITORS

The present invention relates to novel five-membered heterocyclic amidines, to their preparation and to their use as competitive inhibitors of trypsin-like serine proteases, especially thrombin and kininogenases such as kallikrein. The invention also relates to pharmaceutical compositions which contain the compounds as active ingredients, and to the use of the compounds as thrombin inhibitors, anticoagulants and antiinflammatory agents.

Thrombin belongs to the group of serine proteases and plays a central part in the blood coagulation cascade as terminal enzyme. Both the intrinsic and the extrinsic coagulation cascade lead via a plurality of amplifying stages to the production of thrombin from prothrombin. Thrombin-catalyzed cleavage of fibrinogen to fibrin then initiates blood coagulation and aggregation of platelets which, in turn, due to the binding of platelet factor 3 and coagulation factor XIII, and a large number of highly active mediators, enhance thrombin formation.

The formation and action of thrombin are central events in the development both of white, arterial and of red, venous thrombi and are therefore potentially effective points of attack for drugs. Thrombin inhibitors are, by contrast with heparin, able independently of cofactors completely to inhibit simultaneously the effects of free thrombin and of that bound to platelets. They are able to prevent in the acute phase thromboembolic events after percutaneous transluminal coronary angioplasty (PTCA) and lysis, and to act as anticoagulants in extracorporeal circulation (heart-lung machine, hemodialysis). They can also be used generally for the prophylaxis of thrombosis, for example after surgical operations.

It is known that synthetic arginine derivatives influence the enzymatic activity of thrombin by interacting with the active serine residue of the protease thrombin. Peptides based on Phe-Pro-Arg in which the N-terminal amino acid is in the D form have-proven particularly beneficial. D-Phe-Pro-Arg isopropyl ester is described as a competitive thrombin inhibitor (C. Mattson et al., Folia Haematol, 109 (1983) 43–51).

Derivatization of the arginine at the C terminus to the aldehyde leads to an enhancement of the inhibitory effect. Thus, a large number of arginals able to bind the hydroxyl group of the "active" serine in a hemiacetal have been described (EP 185390, 479489, 526877, 542525; WO 93/15756, 93/18060.

The thrombin-inhibitory activity of peptide ketones, fluorinated alkyl ketones and of keto esters, boric acid derivatives, phosphoric esters and α-keto carboxamides can likewise be explained by this serine interaction (EP 118280, 195212, 362002, 364344, 410411, 471651, 589741, 293881, 503203, 504064, 530167; WO 92/07869, 94/08941).

The peptide 4-amidinophenylglycinephosphonate diphenyl esters described by J. Oleksyszyn et al. in J. Med. Chem. 37 (1994) 226–231 are irreversible thrombin inhibitors with inadequate selectivity in respect of other serine proteases.

DE 3 108 810, WO 93/11152 and EP 601 459 describe agmatine and hence arginine derivatives which are unable to interact with the active serine in serine proteases.

WO 94/29336, EP 0 601 459 and WO 95/23609 represent a further development in which the agmatine is replaced by an arylamidine residue.

EP 0 672 658 describes not only thrombin inhibitors which have attached to them an agmatine or benzamidine residue, but also a thrombin inhibitor having an amidinothiophene (Example 65).

Kininogenases are serine proteases which liberate vasoactive peptides, called kinins (bradykinin, kallidin and Met-Lys-bradykinin), from kininogens. Kininogens are multifunctional proteins which occur in coagulation and inflammation cascade reactions. As inhibitors, they protect cells from damage by cysteine proteases (Müller Esterl, FEBS Lett. 182 (1985) 310–314). Important kininogenases are plasma kallikrein, tissue kallikrein and mast cell tryptase.

Kinins like bradykinin and kallidin are vasoactive peptides which influence a large number of biological processes. They play an essential part in inflammatory processes. By increasing vascular permeability, they lead to hypotension and edema. Furthermore, they are very potent pain-producing substances produced naturally in the body and have great importance as cellular mediators in the pathophysiology of asthma, of allergic rhinitis and of arthritis (K. D. Bhoola, C. D. Figueroa, K. Worthy, Pharmacological Reviews 44 (1) (1992) 1–80).

Irrespective of the mechanisms underlying inflammatory processes, fluid containing all the protein systems in the circulating blood escapes from blood vessels. This means that escape of plasma fluid from vessels is involved in diseases such as asthma, rhinitis and inflammatory internal diseases. Moreover, mast cell tryptase is released particularly in allergic processes (Salomonsson et al., Am. Rev. Respir. Dis. 146 (1992) 1535–1542).

The arginine chloromethyl ketones H-(D)-Pro-Phe-Arg-CH$_2$Cl and H-(D)-Phe-Phe-Arg-CH$_2$-Cl have been described by Kettner and Shaw as plasma kallikrein inhibitors (Biochem. 17 (1978) 4778–4784 and Meth. Enzym. 80 (1981) 826–842).

Various synthetic derivatives of benzamidines and benzylamines have proven to be inhibitors of plasma kallikrein, with the benzamidines having a considerably stronger inhibitory effect (F. Markward, S. Drawert, P. Walsmann, Biochemical Pharmacology 23 (1974) 2247–2256).

PKSI-527, the hydrochloride of N-(trans-4-aminomethylcyclohexylcarbonyl)-L-phenylalanine 4-carboxymethylanilide, is also an effective inhibitor of this kininogenase (Wanaka, Ohamoto et al., Thromb. Res., 57 (6) (1990) 889–895).

The invention relates to compounds of the formula I

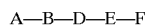   I in which A, B, D, E and F have the following meanings:

A:

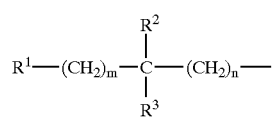

where m is 0, 1 or 2, n is 0, 1 or 2,

R$^1$ is HOOC—, C$_{1-6}$-alkyl-OOC—, aryl-C$_{0-4}$-alkyl-OOC or —OH, $R^2$ is H—, $C_{1-4}$-alkyl- or $R^1$—$(CH_2)_m$— and
$R^3$ is H— or $C_{1-4}$-alkyl-,

B:

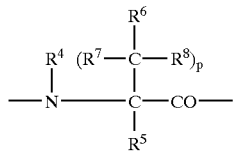

where
$R^4$ is H—, $C_{1-4}$-alkyl- or $R^1$—$(CH_2)_m$— (where $R^1$ and m have the abovementioned meanings),
p is 0 or 1,
$R^5$ is H— or $C_{1-4}$-alkyl-,
$R^6$ is H—, $C_{1-8}$-alkyl-, 2-thienyl-, 3-thienyl-, 3-indolyl-, 4-imidazolyl-, 2-pyridyl-, 3-pyridyl-, 4-pyridyl-, phenyl- which may carry up to three identical or different radicals from the group of $C_{1-4}$-alkyl-, $CF_3$—, $C_{1-4}$-alkoxy-, HO—, BnO—, F— or Cl—, or $C_{3-8}$-cycloalkyl- which may carry up to four identical or different $C_{1-4}$-alkyl radicals and/or where one or two C—C single bonds in the ring can be replaced by a C=C double bond and/or a phenyl ring can be fused on, $C_7$–$C_{12}$-bicycloalkyl- or $C_{10}$-tricycloalkyl- or
$R^4$ and $R^6$ together are an ethylene or propylene group,
$R^7$ is H, $C_{1-8}$-alkyl-, phenyl- which may carry up to three identical or different radicals from the group of $C_{1-4}$-alkyl-, $CF_3$—, $C_{1-4}$-alkoxy-, F— or Cl—, or $C_{3-8}$-cycloalkyl- which may carry up to four identical or different $C_{1-4}$-alkyl radicals, and
$R^8$ is H or $C_{1-4}$-alkyl,

D:

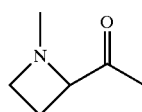 II

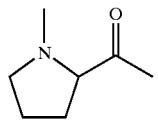 III

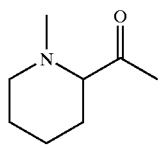 IV

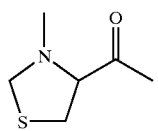 VI

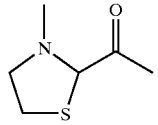 VII

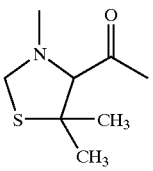 VIII

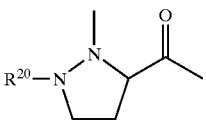 IX

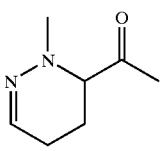 X

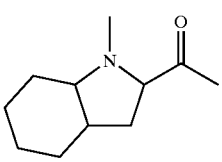 XI where $R^{20}$ is H, $C_{1-4}$-alkyl, Bn or BnO(CO)— and where the following applies:
if D is II, III or XI, then E has the following meaning:

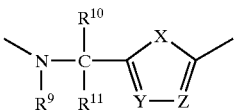

where
a) in the event that X=S, O, NH or $NR^{12}$,
Y is —$CR^{13}$=, —CH= and
Z is —$CR^{14}$=
or
Y is —$CR^{13}$= and
Z is —CH=
or
b) in the event that X=$NR^{12}$,
Y is —CH= and
Z is —CH=
or
c) in the event that X=S, O or NH,
Y is —$CR^{15}$= and
Z is —N=
or
Y is —N= and
Z is —$CR^{15}$=
or
d) in the event that X=—$NR^{12}$—,
Y is —N= and
Z is —$CR^{16}$=, —N=
or
Y is —$CR^{16}$= and
Z is —N=
and
$R^9$ is H— or $C_{1-3}$-alkyl-,
$R^{10}$ is H— or $C_{1-4}$-alkyl-,
$R^{11}$ is H— or $C_{1-4}$-alkyl-,
$R^{12}$ is $CH_3$— or $C_2H_5$—, $R^{13}$ is Cl—, $CF_3$— or $C_{1-4}$alkyl-,
$R^{14}$ is Cl—, $CF_3$— or $C_{1-4}$-alkyl-,
$R^{15}$ is $CF_3$— or $C_{1-4}$-alkyl-,
$R^{16}$ is H—, $CF_3$— or $C_{1-4}$-alkyl- and
$R^{20}$ is as above, or, if D is IV, VI, VII, VIII, IX or X, then E has the following meaning:

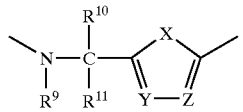

where
X is O, S or —$NR^{17}$—
and
Y is —N= and
Z is —$CR^{16}$= or —N=
or
Y is —$CR^{16}$= and
Z is —N=
or
Y is —$CR^{18}$= and
Z is —$CR^{19}$=
and
$R^9$, $R^{10}$, $R^{11}$, $R^{16}$ and $R^{20}$ are as above,
$R^{17}$ is H, $CH_3$— or $C_2H_5$—,
$R^{18}$ is H—, Cl—, $CF_3$— or $C_{1-4}$-alkyl-,
$R^{19}$ is H—, Cl—, $CF_3$— or $C_{1-4}$-alkyl-,
or
if D is II, III, IV, VI, VII, VIII, IX, X or XI, E has the following meanings:

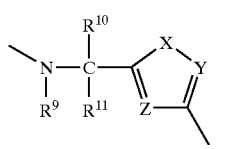 or 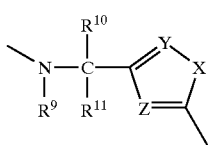

where
a) in the event that X=S,
   Y is —$CR^{18}$= and
   Z is —$CR^{19}$=
   or
   Y is —$CR^{16}$= and
   Z is —N=
   or
b) in the event that X=O or —$NR^{12}$—,
   Y is —N=, —$CR^{16}$= and
   Z is —N=, —$CR^{18}$=
and
$R^9$, $R^{10}$, $R^{11}$, $R^{12}$, $R^{16}$, $R^{18}$, $R^{19}$ and $R^{20}$ have the abovementioned meanings,

F:

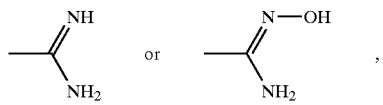

and their salts with physiologically acceptable acids.

The amino acid derivatives represented by B preferably have the (D) configuration; azetidinecarboxylic acid, proline and pipecolic acid in D preferably have the (L) configuration.

Preferred compounds of the formula I are those where A to E have the following meanings:

A:
HOOC—$(CH_2)_t$— (t=1, 2 or 3), (HOOC—$CH_2)_2$—CH—,
HOOC—$CH_2$—CH(COOH)—, HOOC—CH($C_{1-4}$-alkyl)-,
HOOC—C($C_{1-4}$-alkyl)$_2$—,
$C_{1-6}$-alkyl-OOC—$(CH_2)_t$—, B is

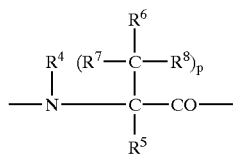

p is 0 or 1,
$R^4$ is H—, $C_{1-4}$-alkyl- or HOOC—$(CH_2)_m$— (m=1, 2 or 3),
$R^5$ is H—, methyl-
$R^6$ is H—, $C_{1-8}$-alkyl-, 2-thienyl-, 3-thienyl-, 3-indolyl-, 4-imidazolyl-, 2-pyridyl-, 3-pyridyl-, 4-pyridyl-, phenyl- which may carry up to three identical or different radicals from the group of $CH_3$—, $CF_3$—, $CH_3$—O—, HO—, BnO—, F— or Cl—, or $C_{3-8}$-cycloalkyl, which may carry up to four methyl radicals, bicyclo[2.2.2]octyl-, bicyclo[2.2.1]heptyl-, adamantyl-, indanyl-, decalinyl-,
$R^7$ is H, $C_{1-8}$-alkyl-, phenyl-, which may carry up to three identical or different radicals from the group of $CH_3$—, $CF_3$—, $CH_3O$—, F— or Cl—, or $C_{3-8}$-cycloalkyl- which may carry up to four methyl radicals,
$R^8$ is H, $C_{1-4}$-alkyl,

D:

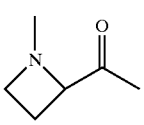

II

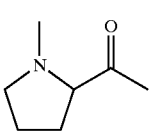

III

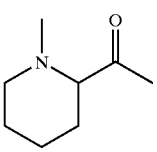

IV

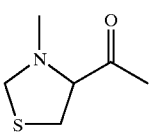

VI

-continued

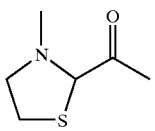

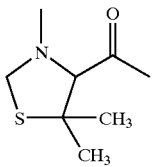

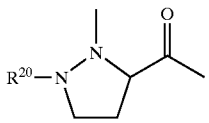

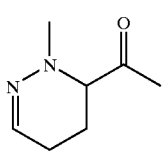

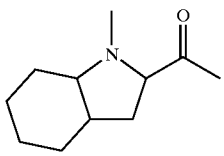

where $R^{20}$ is H, $CH_3$, Bn oder BnO(CO)— and where the following applies:

if D is II, III or XI, then E has the meaning:

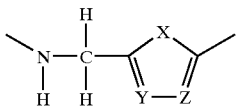

where
a) in the event that X=S, O or $NR^{17}$,
Y is $—CR^{13}=$ or $—CH=$ and
Z is $—CR^{14}=$
or
Y is $—CR^{13}=$ and
Z is $—CH=$
or
b) in the event that X=$NR^{12}$,
Y is $—CH=$ and
Z is $—H=$,
or
c) in the event that X=S, O or NH,
Y is $—CR^{15}=$ and
Z is $—N=$
or
Y is $—N=$ and
Z is $—CR^{15}=$
or
d) in the event that X=$NR^{12}$,
Y is $—N=$ and
Z is $—CR^{16}=$, $—N=$
or Y is $—CR^{16}=$ and
Z is $—N=$
and
$R^{12}$ is $CH_3—$ or $C_2H_5—$,
$R^{13}$ is Cl—, $CF_3—$ or $C_{1-4}$-alkyl-,
$R^{14}$ is Cl—, $CF_3—$ or $C_{1-4}$-alkyl-,
$R^{15}$ is $CF_3—$ or $C_{1-4}$alkyl-,
$R^{16}$ is H—, $CF_3—$ or $C_{1-4}$-alkyl-,
$R^{17}$ is H, $CH_3—$ or $C_2H_5—$
$R^{20}$ is as above, or
if D is IV, VI, VII, VIII, IX or X, then E has the meaning:

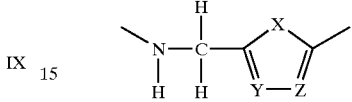

where
X is O, S or $—NR^{17}—$ and where
Y is $—N=$ and
Z is $—CR^{16}=$ or $—N=$
or
Y is $—CR^{16}=$ and
Z is $—N=$
or
Y is $—CR^{18}=$ and
Z is $—CR^{19}=$
and
$R^{16}$, $R^{17}$, $R^{20}$ have the abovementioned meanings,
$R^{18}$ is H—, Cl—, $CF_3—$ or $C_{1-4}$-alkyl- and
$R^{19}$ is H—, Cl—, $CF_3—$ or $C_{1-4}$-alkyl-,
or
if D is II, III, IV, VI, VII, VIII, IX, X or XI, then E has the meanings:

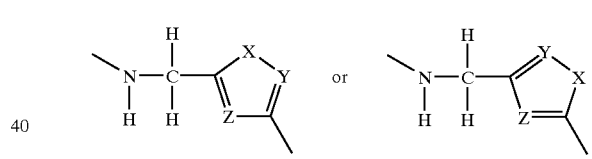

where
a) in the event that X=S,
Y is $—CR^{18}=$ and
Z is $—CR^{19}=$
or
Y is $—CR^{16}=$ and
Z is $—N=$
or
b) in the event that X=O or $—NR^{12}—$,
Y is $—N=$ or $—CR^{16}=$ and
Z is $—N=$ or $—CR^{18}=$
and $R^{12}$, $R^{16}$, $R^{18}$, $R^{19}$ and $R^{20}$ have the abovementioned meanings,
F:

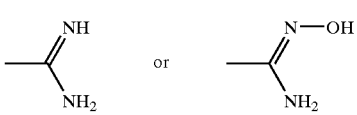

and their salts with physiologically acceptable acids.

The amino acid derivatives represented by B preferably have the (D) configuration; azetidinecarboxylic acid, proline and pipecolic acid in D preferably have the (L) configuration.

Especially preferred compounds of the formula I are those where A, B, D, E and F have the following meanings:

A: HOOC—CH$_2$, HOOC—CH$_2$—CH$_2$, HOOC—CH(CH$_3$), HOOC—CH(C$_2$H$_5$)

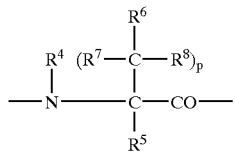

p is 0 or 1,
R$^4$ is H—, CH$_3$—
R$^5$ is H—, CH$_3$—,
R$^6$ is C$_{1-8}$-alkyl-, C$_{5-8}$-cycloalkyl- which may carry up to four methyl radicals, 2-thienyl-, 3-indolyl-, 4-imidazolyl-, 2-pyridyl-, 3-pyridyl-, 4-pyridyl, phenyl- which may carry up to three identical or different radicals from the group of CH$_3$—, CF$_3$—, CH$_3$O—, HO—, BnO—, F— or Cl—, bicyclo[2.2.2]octyl, bicyclo[2.2.1]heptyl, adamantyl, indanyl, decalinyl, with particular emphasis on cyclopentyl, cyclohexyl and cycloheptyl,
R$^7$ is H, CH$_3$—,
R$^8$ is H, CH$_3$—,

D:

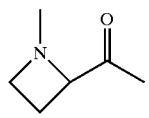 II

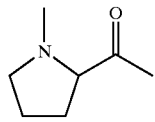 III

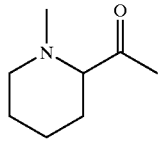 IV

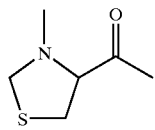 VI

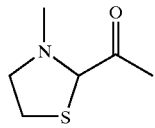 VII

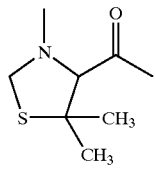 VIII

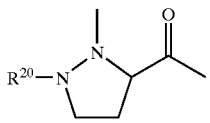 IX

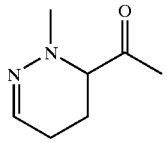 X

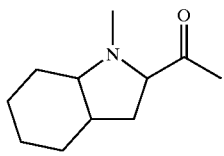 XI where R$^{20}$ is H, BnO(CO)— and
where the following applies:
if D is II, III or XI, then E has the meaning

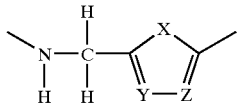

where
X is —S— and where
Y is —CH= and
Z is —CR$^{13}$=
or
Y is —CR$^{13}$= and
Z is —CH=
or
Y is —CR$^{15}$= and
Z is —N=
or
Y is —N= and
Z is —CR$^{15}$=
and
R$^{13}$ is Cl—, CF$_3$— or CH$_3$—
R$^{15}$ is CF$_3$— or CH$_3$— and
R$^{20}$ is as above,
or
if D is IV, VI, VII, VIII, IX or X, then E has the meaning:

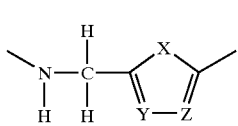

where
X is S and where
Y is —N= and
Z is —CR$^{16}$=
or
Y is —CR$^{16}$= and
Z is —N=
or Y is —CR$^{13}$= and
Z is —CH=
or
Y is —CH= and
Z is —CR$^{13}$=
or
Y is —CH= and
Z is —CH=
and
R$^{13}$, R$^{20}$ have the abovementioned meanings and
R$^{16}$ is H—, CF$_3$— or CH$_3$—
or
if D is II, III, IV, VI, VII, VIII, IX, X or XI, then E has the meanings:

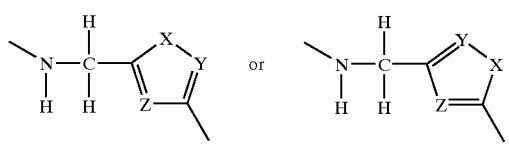

where either
  a) in the event that X=S,
     Y is —CH= and
     Z is —CR$^{18}$=
     or
     Y is —CR$^{16}$= and
     Z is —N=
     or
     Y is —CR$^{18}$= and
     Z is —CH=
     or
  b) in the event that X=O or NCH$_3$
     Y is —CH= and
     Z is —CR$^{16}$=
     or
     Y is —CR$^{16}$= and
     Z is —CH=
     or
  c) in the event that X=—NR$^{12}$—
     Y is —N= and
     Z is —CR$^{18}$=
     and
     R$^{12}$ is CH$_3$— or C$_2$H$_5$— and
     R$^{18}$ is H, Cl—, CF$_3$— or CH$_3$—, and
     R$^{16}$, R$^{20}$ have the abovementioned meanings
F:

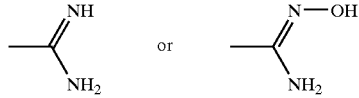

and their salts with physiologically acceptable acids.

The amino acid derivatives represented by B preferably have the (D) configuration; azetidinecarboxylic acid, proline and pipecolic acid in D preferably have the (L) configuration.

Very especially preferred compounds of the formula I are those where A, B, D, E and F have the following meanings:
A: HOOC—CH$_2$, HOOC—CH$_2$—CH$_2$, HOOC—CH(CH$_3$), HOOC—CH(C$_2$H$_5$)
B:

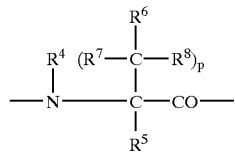

p is 0 or 1,
R$^4$ is H—,
R$^5$ is H—,
R$^6$ is C$_{1-8}$-alkyl-, 2-thienyl-, 3-indolyl-, 4-imidazolyl-, 2-pyridyl-, 3-pyridyl-, 4-pyridyl-, C$_{5-8}$-cycloalkyl- which may carry up to four methyl radicals, phenyl- which may carry up to three identical or different radicals from the group of CH$_3$—, CF$_3$—, CH$_3$O—, HO—, BnO—, F— or Cl—, bicyclo[2.2.2]octyl, bicyclo[2.2.1]heptyl, adamantyl, indanyl, decalinyl, with particular emphasis on cyclopentyl-, cyclohexyl- and cycloheptyl-,
R$^7$ is H,
R$^8$ is H,
D:

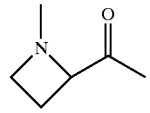

II

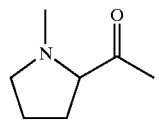

III

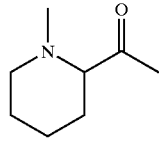

IV

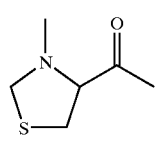

VI

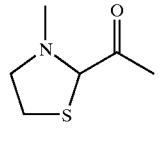

VII

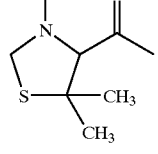

VIII

-continued

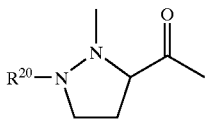

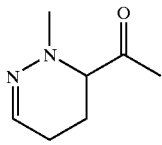

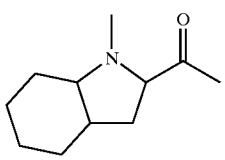

where the following applies:
if D is II, III or XI, then E has the meaning

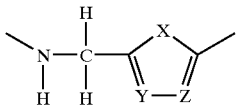

where
X is S and
Y is —CR$^{13}$= and
Z is —CH=
or
Y is —CH= and
Z is —CR$^{13}$=
or
Y is —CR$^{15}$= and
Z is —N=
or
Y is —N= and
Z is —CR$^{15}$=
and
R$^{13}$ is Cl—, CF$_3$— or CH$_3$— and
R$^{15}$ is CF$_3$— or CH$_3$—,
or
if D is IV, VI, VII, VIII, IX or X, then E has the meaning

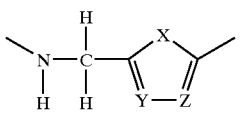

where
X is S and
Y is —N= and
Z is —CR$^{16}$=
or
Y is —CR$^{16}$= and
Z is —N=
or
Y is —CH= and
Z is —CR$^{13}$=
or
Y is —CR$^{13}$= and
Z is —CH=
or
Y is —CH= and
Z is —CH=
and
R$^{13}$ has the abovementioned meaning and
R$^{16}$ is H, CF$_3$— or CH$_3$—, or
if D is II, III, IV, VI, VII, VIII, IX, X or XI, then E has the meanings

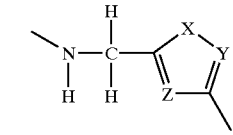 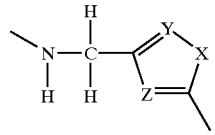

where
a) in the event that X=S,
Y is —CH= and
Z is —CR$^{18}$=
or
Y is —CR$^{18}$= and
Z is —CH=
or
Y is —CR$^{16}$= and
Z is —N=
or
b) in the event that X=O or NCH$_3$
Y is —CH= and
Z is —CR$^{16}$=
or
Y is —CR$^{16}$= and
Z is —CH=
or
c) in the event that X=NCH$_3$
Y is —N= and
Z is —CR$^{16}$=
and
R$^{16}$ has the abovementioned meaning and
R$^{18}$ is H, Cl— CF$_3$— or CH$_3$—,
F:

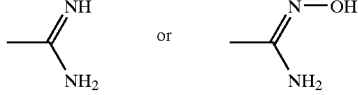

and their salts with physiologically acceptable acids.

The amino acid derivatives represented by B preferably have the (D) configuration; azetidinecarboxylic acid, proline and pipecolic acid in D preferably have the (L) configuration.

With the exception of the compounds mentioned in the Examples, the following substances must be very especially emphasized:

HOOC—CH$_2$-(D)-Cha-Pro-NH—CH$_2$-5-(2-am-3-CF$_3$)-thioph

HOOC—CH$_2$-(D)-Chg-Pro-NH—CH$_2$-5-(2-am-3-CF$_3$)-thioph

HOOC—CH$_2$-(D)-Cha-Pro-NH—CH$_2$-5-(2-am-4-Me)-thioph

HOOC—CH₂-(D)-Cha-Pro-NH—CH₂-5-(2-am-4-Cl)-thioph
HOOC—CH₂-(D)-Cha-Pro-NH—CH₂-5-(2-am-4-CF₃)-thioph
HOOC—CH₂-(D)-Chg-Pro-NH—CH₂-5-(2-am-4-Me)-thioph
HOOC—CH₂-(D)-Chg-Pro-NH—CH₂-5-(2-am-4-Cl)-thioph
HOOC—CH₂-(D)-Chg-Pro-NH—CH₂-5-(2-am-4-CF₃)-thioph
HOOC—CH₂-(D)-Chg-Pro-NH—CH₂-5-(2-am-3,4-Me₂)-thioph
HOOC—CH₂-(D)-Cha-Aze-NH—CH₂-2-(4-am)-thioph
HOOC—CR₂-(D)-Chg-Pic-NH—CH₂-2-(5-am)-thioph
HOOC—CH₂-(D)-Cha-Pic-NH—CH₂-2-(4-am)-thioph
HOOC—CH₂-(D)-Chg-Pic-NH—CH₂-2-(4-am)-thioph
HOOC—CH₂-(D)-Cha-Pic-NH—CH₂-2-(5-am-3-Me)-thioph
HOOC—CH₂-(D)-Chg-Pic-NH—CH₂-2-(5-am-3-Me)-thioph
HOOC—CH₂-(D)-Cha-Pic-NH—CH₂-2-(5-am-3-Cl)-thioph
HOOC—CH₂-(D)-Chg-Pic-NH—CH₂-2-(5-am-3-Cl)-thioph
HOOC—CH₂-(D)-Cha-Pic-NH—CH₂-2-(5-am-4-Me)-thioph
HOOC—CH₂-(D)-Chg-Pic-NH—CH₂-2-(5-am-4-Me)-thioph
HOOC—CH₂-(D)-Cha-Pic-NH—CH₂-2-(5-am-4-Cl)-thioph
HOOC—CH₂-(D)-Chg-Pic-NH—CH₂-2-(5-am-4-Cl)-thioph
HOOC—CH₂-(D)-Chea-Pro-NH—CH₂-2-(4-am)-thioph
HOOC—CH₂-(D)-Cpa-Pro-NH—CH₂-2-(4-am)-thioph
HOOC—CH₂-(D)-Chg-Pro-NH—CH₂-2-(4-am-5-Me)-thioph
HOOC—CH₂-(D)-Chg-Pro-NH—CH₂-2-(4-am-5-Cl)-thioph
HOOC—CH₂-(D)-Chg-Pro-NH—CH₂-2-(4-am-5-CF₃)-thioph
HOOC—CH₂-CH₂-(D)-Chg-Pro-NH—CH₂-2-(4-am)-thioph
HOOC—CH₂-CH₂-(D)-Cha-Pro-NH—CH₂-2-(4-am)-thioph
HOOC—CH₂-(D)-Chea-Pro-NH—CH₂-4-(2-am)-thioph
HOOC—CH₂-(D)-Cpa-Pro-NH—CH₂-4-(2-am)-thioph
HOOC—CH₂-(D)-Chg-Pro-NH—CH₂-4-(2-am)-thioph
HOOC—CH₂-(D)-Cheg-Pro-NH—CH₂-4-(2-am)-thioph
HOOC—CH₂-(D)-Cpg-Pro-NH—CH₂-4-(2-am)-thioph
HOOC—CH₂-(D)-Cha-Pic-NH—CH₂-2-(4-am)-thiaz
HOOC—CH₂-(D)-Chg-Pic-NH—CH₂-2-(4-am)-thiaz
HOOC—CH₂-(D)-Cha-Aze-NH—CH₂-2-(4-am)-thiaz
HOOC—CH₂-(D)-Chg-Aze-NH—CH₂-2-(4-am)-thiaz
MeOOC—CH₂-(D)-Cha-Pro-NH—CH₂-2-(4-am)-thiaz
HOOC—CH₂-(D)-Cpg-Pro-NH—CH₂-2-(4-am)-thiaz
HOOC—CH₂-(D)-Chea-Pro-NH—CH₂-2-(4-am)-thiaz
HOOC—CH₂-(D)-Cheg-Pro-NH—CH₂-2-(4-am)-thiaz
HOOC—CH₂-(D)-Cha-Pic-NH—CH₂-2-(4-am)-thiaz
HOOC—CH₂-(D)-Chg-Pic-NH—CH₂-2-(4-am)-thiaz
HOOC—CH₂-CH₂-(D)-Cha-Pro-NH—CH₂-2-(4-am)-thiaz
HOOC—CH₂-CH₂-(D)-Chg-Pro-NH—CH₂-2-(4-am)-thiaz
HOOC—CH₂-(D)-Cha-Pro-NH—CH₂-2-(4-am-5-Me)-thiaz
HOOC—CH₂-(D)-Chg-Pro-NH—CH₂-2-(4-am-5-Me)-thiaz
HOOC—CH₂-(D)-Cha-Pro-NH—CH₂-2-(4-am-5-CF₃)-thiaz
HOOC—CH₂-(D)-Chg-Pro-NH—CH₂-2-(4-am-5-CF₃)-thiaz
HOOC—CH₂-(D)-Cha-Pro-NH—CH₂-2-(5-am-4-Me)-thiaz
HOOC—CH₂-(D)-Chg-Pro-NH—CH₂-2-(5-am-4-Me)-thiaz
HOOC—CH₂-(D)-Cha-Pro-NH—CH₂-2-(5-am-4-CF₃)-thiaz
HOOC—CH₂-(D)-Chg-Pro-NH—CH₂-2-(5-am-4-CF₃)-thiaz
HOOC—CH₂-(D)-Chg-Pro-NH—CH₂-5-(3-am)-isox
HOOC—CH₂-(D)-Cha-Pro-NH—CH₂-2-(4-am)-oxaz
HOOC—CH₂-(D)-Chg-Pro-NH—CH₂-2-(4-am)-oxaz
HOOC—CH₂-CH₂-(D)-Chg-Pro-NH—CH₂-5-(3-am)-fur
HOOC—CH₂-CH₂-(D)-Cha-Pro-NH—CH₂-5-(3-am)-fur
HOOC—CH₂-(D)-Chea-Pro-NH—CH₂-5-(3-am)-fur
HOOC—CH₂-(D)-Cha-Pic-NH—CH₂-5-(3-am)-fur
HOOC—CH₂-(D)-Chg-Pic-NH—CH₂-5-(3-am)-fur
HOOC—CH₂-CH₂-(D)-Cha-Pic-NH—CH₂-5-(3-am)-fur
HOOC—CH₂-CH₂-(D)-Chg-Pic-NH—CH₂-5-(3-am)-fur
HOOC—CH₂-(D)-Chg-Aze-NH—CH₂-5-(3-am)-fur
HOOC—CH₂-(D)-Cha-Aze-NH—CH₂-5-(3-am)-fur
HOOC—CH₂-(D)-Cha-Aze-NH—CH₂-2-(4-am-1-Me)-pyrr
HOOC—CH₂-(D)-Chg-Aze-NH—CH₂-2-(4-am-1-Me)-pyrr
HOOC—CH₂-(D)-Chg-Pro-NH—CH₂-2-(4-am-1-Me)-pyrr
HOOC—CH₂-(D)-Cha-Pic-NH—CH₂-2-(4-am-1-Me)-pyrr
HOOC—CH₂-(D)-Chg-Pic-NH—CH₂-2-(4-am-1-Me)-pyrr
HOOC—CH₂-(D)-Cha-Aze-NH—CH₂-2-(5-am-1-Me)-pyrr
HOOC—CH₂-(D)-Chg-Aze-NH—CH₂-2-(5-am-1-Me)-pyrr
HOOC—CH₂-(D)-Chg-Pro-NH—CH₂-2-(5-am-1-Me)-pyrr
HOOC—CH₂-(D)-Cha-Pic-NH—CH₂-2-(5-am-1-Me)-pyrr
HOOC—CH₂-(D)-Chg-Pic-NH—CH₂-2-(5-am-1-Me)-pyrr
HOOC—CH₂-(D)-Cha-Aze-NH—CH₂-4-(2-am-1-Me)-pyrr
HOOC—CH₂-(D)-Chg-Aze-NH—CH₂-4-(2-am-1-Me)-pyrr
HOOC—CH₂-(D)-Chg-Pro-NH—CH₂-4-(2-am-1-Me)-pyrr
HOOC—CH₂-(D)-Cha-Pic-NH—CH₂-4-(2-am-1-Me)-pyrr
HOOC—CH₂-(D)-Chg-Pic-NH—CH₂-4-(2-am-1-Me)-pyrr HOOC—CH₂-(D)-Cha-Aze-NH—CH₂-5-(3-am-1-Me)-pyraz
HOOC—CH₂-(D)-Chg-Aze-NH—CH₂-5-(3-am-1-Me)-pyraz
HOOC—CH₂-(D)-Chg-Pro-NH—CH₂-5-(3-am-1-Me)-pyraz
HOOC—CH₂-(D)-Cha-Pic-NH—CH₂-5-(3-am-1-Me)-pyraz
HOOC—CH₂-(D)-Chg-Pic-NH—CH₂-5-(3-am-1-Me)-pyraz
HOOC—CH₂-(D)-Cha-Aze-NH—CH₂-3-(5-am-1-Me)-pyraz
HOOC—CH₂-(D)-Chg-Aze-NH—CH₂-3-(5-am-1-Me)-pyraz
HOOC—CH₂-(D)-Cha-Pro-NH—CH₂-3-(5-am-1-Me)-pyraz
HOOC—CH₂-(D)-Chg-Pro-NH—CH₂-3-(5-am-1-Me)-pyraz
HOOC—CH₂-(D)-Cha-Pic-NH—CH₂-3-(5-am-1-Me)-pyraz
HOOC—CH₂-(D)-Chg-Pic-NH—CH₂-3-(5-am-1-Me)-pyraz
HOOC—CH₂-(D)-Chg-Pro-NH—CH₂-5-(3-am)-oxadiaz
tBuOOC—H₂-N-BOC-(D)-Chg-Pro-NH—CH₂-2-(4-am)-oxaz
HOOC—CH₂-(D)-Chg-Pro-NH—CH₂-5-(3-am-4-Cl)-thioph
EtOOC—CH₂-(D)-Chg-Pro-NH—CH₂-5-(3am-4-Cl)-thioph
HOOC—CH₂-(D)-Chg-Pro-NH-H₂-5-(3-am-4-Me)-thioph
EtOOC—CH₂-(D)-Chg-Pro-NH—CH₂-5-3-am-4-Me)-thioph
tBuOOC—CH₂-(D)-Cha-Pro-NH—CH₂-4-(2-ham)-thioph
tBuOOC—CH₂-(D)-Chg-Pro-NH—CH₂-4-(2-ham)-thioph
tBuOOC—H₂-(D)-Chg-Aze-NH—CH₂-4-(2-ham)-thioph
tBuOOC—CH₂-(D)-Cha-Aze-NH—CH₂-4-(2-ham)-thioph
tBuOOCCH₂-(D)-Cha-Pro-NH—CH₂-4-(2-ham)-thiaz
tBuOOC—CH₂-(D)-Chg-Pro-NH—CH₂-4-(2-ham)-thiaz
tBuOOC—CH₂-(D)-Chg-Aze-NH—CH₂-4-(2-ham)-thiaz
tBuOOC—CH₂-(D)-Cha-Aze-NH—CH₂-4-(2-ham)-thiaz

| List of abbreviations: | |
|---|---|
| Adaala: | adamantylalanine |
| Adagly: | adamantylglycine |
| AIBN: | azobisisobutyronitrile |
| Ac: | acetyl |
| am: | amidino |
| Aze: | azetidinecarboxylic acid |
| Bn: | benzyl |
| bs: | broad singulet |
| Boc: | tert-butyloxycarbonyl |
| Bu: | butyl |
| Cbz: | benzyloxycarbonyl |
| Cha: | cyclohexylalanine |
| Chea: | cycloheptylalanine |
| Cheg: | cycloheptylglycine |
| Chg: | cyclohexylglycine |
| Cog: | cyclooctylglycine |
| Cpa: | cyclopentylalanine |
| Cpg: | cyclopentylglycine |
| d: | doublet |
| TLC: | Thin-layer chromatography |
| DCC: | dicyclohexylcarbodiimide |
| Dch: | dicyclohexylalanine |
| Dcha: | dicyclohexylamine |
| DCM: | dichloromethane |
| Dep: | 4,5-dehydropipecolic acid |
| DMF: | dimethylformamide |
| DIPEA: | diisopropylethylamine |
| Dpa: | diphenylalanine |
| EDC: | N-ethyl-N'-(3-dimethylaminopropyl)carbodiimide-hydrochloride |
| Et: | ethyl |
| Eq: | equivalents |
| Gly: | glycine |
| fur: | furan |
| ham: | hydroxyamidino |
| HOSucc: | hydroxysuccinimide |
| HPLC: | high-performance liquid chromatography |
| imi: | imidazole |
| iPr: | isopropyl |
| isox: | isoxazole |
| Leu: | leucine |
| Lsg: | solution |
| Me: | methyl |
| α-MeCha: | α-methylcyclohexylalanine |
| β, β-Me₂Cha: | 2-amino-3-cyclohexyl-3-methylbutyric acid or β,β-dimethylcyclohexylalanine |
| 4-MeCha: | (4-methylcyclohex-1-yl)alanine |
| γ-MeCha: | (1-methylcyclohex-1-yl)alanine |
| 3,3-Me₂Cha: | (3,3-dimethylcyclohex-1-yl)alanine |
| 4-MeChg: | (4-methylcyhex-1-yl)glycine [sic] |
| 3,3-Me₂Chg: | (3,3-dimethylcyclohex-1-yl)glycine |
| MPLC: | medium-pressure liquid chromatography |
| MTBE: | methyl tert-butyl ether |
| NBS: | N-bromosuccinimide |
| Nog: | norbornylglycine |
| Ohind: | (2)-octahydroindole-2-carboxylic acid |
| Oxadiaz: | 1,2,4-oxadiazole |
| Oxaz: | oxazole |
| Ph: | phenyl |
| Phe: | phenylalanine |
| Pic: | pipecolic acid |
| PPA: | propylphosphonic anhydride |
| Pro: | proline |
| Py: | pyridine |
| pydaz: | (3S)-2,3,4,5-tetrahydropyridazine-3-carboxylic acid |
| Pyr: | 3,4-dehydroproline |
| pyraz: | pyrazole |
| pyrr: | pyrrole |
| pyzo-3: | (3S)pyrazolidine-3-carboxylic acid |
| q: | quartet |
| RT: | room temperature |
| RP-18: | reversed phase C-18 |
| s: | singulet |
| sbr: | singulet, broad |
| t: | triplet |
| t: | tertiary |
| tBu: | tertiary-butyl |
| tert: | tertiary |
| TBAB: | tetrabutylammonium bromide |
| TEA: | trietylamine [sic] |
| TFA: | trifluoroacetic acid |
| TFFA: | trifluoroacetic anhydride |
| thiaz: | thiazole |
| thioph: | thiophene |
| Thz-2: | thiazolodine-2-carboxylic [sic] acid |
| Thz-4: | thiazolidine-4-carboxylic acid |
| 5,5-Me₂Thz-4: | (4S)-5.5-dimethylthiazolidine-4-carboxylic acid |
| TOTU: | O-(cyanoethoxycarbonylmethylene)amino-N,N,N',N'-tetramethyluronium tetrafluoroborate |

-continued

List of abbreviations:

| triaz: | 1,2,4-triazole |
| Z: | benzyloxycarbonyl |

In the description and the claims, the following definitions apply to the individual substituents:

The term "cycloalkyl", on its own or as part of another substituent comprises saturated or cyclic hydrocarbon groups which contain the given number of carbon atoms. $C_{3-8}$-cycloalkyl refers to saturated alicyclic rings having 3 to 8 C atoms such as, for example, cyclopropyl, cyclobutyl, cyclopentyl, cyclohexyl, 4-methylcyclohexyl, cycloheptyl or cyclooctyl.

The term "alkyl" on its own or as part of another substituent denotes a linear or branched alkyl chain radical of the length indicated in each case. Thus, $C_{1-4}$-alkyl is, for example, methyl, ethyl, 1-propyl, 2-propyl, 2-methyl-2-propyl, 2-methyl-1-propyl, 1-butyl, 2-butyl, $C_{1-6}$-alkyl, for example $C_{1-4}$-alkyl, pentyl, 1-pentyl, 2-pentyl, 3-pentyl, 1-hexyl, 2-hexyl, 3-hexyl, 4-methyl-1-pentyl or 3,3-dimethylbutyl. In addition to the radicals given for $C_{1-4}$-alkyl, $C_{1-8}$-alkyl denotes, for example, $C_{1-6}$-alkyl, heptyl or octyl.

The term "alkoxy" on its own or as part of another substituent denotes a linear or branched alkyl chain radical which has the length indicated in each case and which is bonded to the respective basic compound via an oxygen atom. Thus $C_{1-4}$-alkoxy denotes, for example, methoxy, ethoxy, 1-propoxy, 2-propoxy, 2-methyl-2-propoxy, 2-methyl-1-propoxy, 1-butoxy, 2-butoxy.

The invention furthermore relates to compounds which contain the structural element

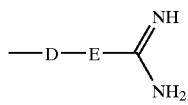

where D and E have the abovementioned meanings and where a hydrogen atom, a protective group, an unsubstituted or substituted natural or unnatural amino acid, an unsubstituted or substituted carboxylic acid or an unsubstituted or substituted alkyl radical is located on the nitrogen atom of building block D. The structural fragment is valuable as a component of serine protease inhibitors and, in particular, of thrombin and kallikrein inhibitors.

The invention also relates to compounds which contain the structural element

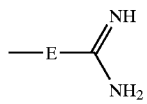

where E has the abovementioned meaning and where a hydrogen atom, a protective group, an unsubstituted or substituted natural or unnatural amino acid, an unsubstituted or substituted carboxylic acid or an unsubstituted or substituted alkyl radical is located on the nitrogen atom of $NR^9$.

Finally, the invention also relates to compounds which have one of the following structural elements:

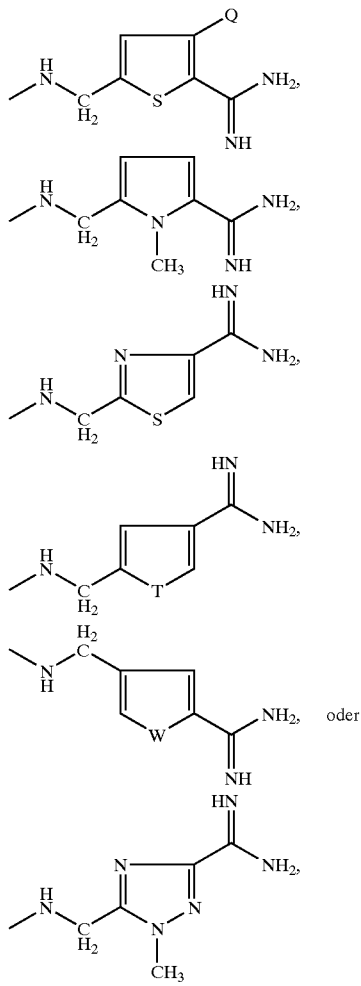

where Q is $CH_3$ or Cl; T is $NCH_3$, O or S; and W is $NCH_3$ or S.

The invention furthermore relates to the intermediates of the formulae Va and Vb

| A—B—D—E—CN | Va, |
| A—B—D—E—CSNH$_2$ | Vb, | where A, B, D and E have the abovementioned meanings.

The novel intermediates are used to prepare the compounds I and are valuable building blocks for synthesizing serine protease inhibitors.

The compounds of the formula I can exist as such or in the form of their salts with physiologically acceptable acids. Examples of such acids are: hydrochloric acid, citric acid, tartaric acid, lactic acid, phosphoric acid, methanesulfonic acid, acetic acid, formic acid, maleic acid, fumaric acid, succinic acid, hydroxysuccinic acid, sulfuric acid, glutaric acid, aspartic acid, pyruvic acid, benzoic acid, glucuronic acid, oxalic acid, ascorbic acid and acetylglycine.

If, in the compounds of the formula I, $R^1$ equals $C_{1-6}$-alkyl-OOC, aryl-$C_{0-4}$-alkyl-OOC and/or F equals hydroxyamidine, these compounds may act in vivo as prodrugs from which the corresponding carboxylic acids $R^1$=HOOC— or the corresponding amidines F=—C(=NH)-NH$_2$ are formed enzymatically.

Prodrugs of the compounds of the formula I are to be understood as meaning those compounds which are metabolized in vivo to give the pharmacologically active compounds of the formula I. This can be effected, for example, by the first-pass metabolism in the liver.

The novel compounds of the formula I are competitive inhibitors of trypsin-like serine proteases, especially of thrombin, and also of kininogenases such as kallikrein. They can be employed for the following indications:

diseases whose pathogenetic mechanism derives directly or indirectly from the proteolytic effect of thrombin, diseases whose pathogenetic mechanism derives from thrombin-dependent activation of receptors and signal transductions, diseases associated with stimulation [eg. by PAI-1, PDGF (platelet derived growth factor), P-selectin, ICAM-1, tissue factor] or inhibition (eg. NO synthesis in smooth muscle cells) of the expression of genes in body cells, diseases deriving from the mitogenic effect of thrombin, diseases deriving from a thrombin-dependent change in the contractility and permeability of epithelial cells (eg. vascular endothelial cells), thrombin-dependent thromboembolic events such as deep vein thrombosis, pulmonary embolism, myocardial or cerebral infarct, atrial fibrillation, bypass occlusion, disseminated intravascular coagulation (DIC), reocclusion and for reducing the reperfusion time on comedication with thrombolytics such as streptokinase, urokinase, prourokinase, t-PA, APSAC, plasminogen activators from the salivary glands of animals, and the recombinant and mutated forms of all these substances, the occurrence of early reocclusion and late restenosis after PTCA, the thrombin-dependent proliferation of smooth muscle cells, the accumulation of active thrombin in the CNS (eg. in Alzheimer's disease), tumor growth and to prevent adhesion and metastasis of tumor cells.

The novel compounds can be used in particular for the therapy and prophylaxis of thrombin-dependent thromboembolic events such as deep vein thromboses, pulmonary embolisms, myocardial or cerebral infarcts and unstable angina, also for the therapy of disseminated intravascular coagulation (DIC). They are furthermore suitable for combination therapy with thrombolytics such as streptokinase, urokinase, prourokinase, t-PA, APSAC and other plasminogen activators to shorten the reperfusion time and extend the reocclusion time.

Further preferred areas of use are to prevent thrombin-dependent early reocclusion and late restenosis after percutaneous transluminal coronary angioplasty, to prevent thrombin-induced proliferation of smooth muscle cells, to prevent accumulation of active thrombin in the CNS (eg. in Alzheimer's disease), to control tumors and to prevent mechanisms which lead to adhesion and metastasis of tumor cells.

The novel compounds can also be used for coating artificial surfaces such as hemodialysis membranes and the tubing systems and lines necessary therefor, and for coating oxygenators in extravascular circulation, stents and heart valves.

The novel compounds can furthermore be employed for diseases whose pathogenetic mechanism derives directly or indirectly from the proteolytic effect of kininogenases, especially kallikrein, eg. in inflammatory diseases such as asthma, pancreatitis, rhinitis, arthritis, urticaria and other internal inflammatory diseases.

The compounds according to the invention can be administered in a conventional way orally or parenterally (subcutaneously, intravenously, intramuscularly, interperitoneally, rectally). Administration can also take place with vapors or sprays through the nasopharyngeal space.

The dosage depends on the age, condition and weight of the patient and on the mode of administration. As a rule, the daily dose of active substance per person is about 10–2000 mg on oral administration and about 1–200 mg on parenteral administration. This dose can be given in 2 to 4 single doses or once a day as depot form.

The novel compounds can be used in conventional solid or liquid pharmaceutical forms, eg. as uncoated or (film-) coated tablets, capsules, powders, granules, sugar-coated tablets, suppositories, solutions, ointments, creams or sprays. These are produced in a conventional manner. The active substances can for this purpose be mixed with conventional pharmaceutical auxiliaries such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1978). The administration forms obtained in this way normally contain from 0.1 to 99% by weight of active substance.

EXPERIMENTAL PART

The compounds of the formula I can be prepared as shown in Schemes I–III.

Building blocks A, B, D and E are preferably assembled separately beforehand and employed in suitably protected form (see Scheme I–III).

Scheme I

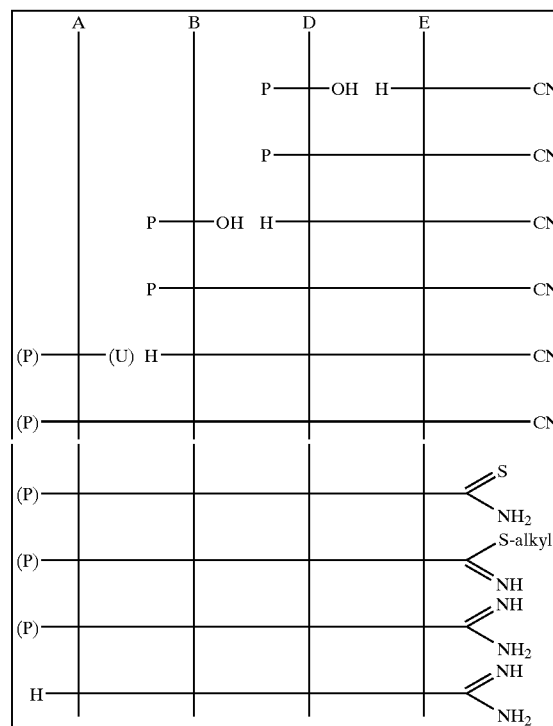

(P = protective group, (P) = protective group or H)

Scheme I describes the linear assemblage of the molecule I by coupling the amine H—E—CN to the N-protected amino acid P—D—OH to give P—D—E—CN, eliminating the N-terminal protective group to give H—D—E—CN, coupling to the N-protected amino acid P—B—OH to give P—B—D—E—CN, eliminating the protective group P to give H—B—D—E—CN, subsequently alkylating with the unprotected or protected (P)—A—U building block (U=leaving group) or reductively alkylating with (P)—A'—U (U=aldehyde, ketone) or Michael addition with a suitable (P)—A"—C═C— derivative to give (P)—A—B—D—E—CN. Conversion of the nitrile functionality into the amidine group takes place either by the classical Pinner synthesis (R. Boder, D. G. Neilson, Chem. Rev. 61 (1962) 179) or by a modified Pinner synthesis which proceeds via imino thioester salts as intermediate (H. Vieweg et al., Pharmazie 39 (1984) 226) or directly by the method of A. Eschenmoser Helv. Chimica Acta 69 (1986) 1224. Subsequently the protective groups still present in the molecule are eliminated, preferably by acid hydrolysis.

If building block E is incorporated as H—E—CONH$_2$ into the synthesis, dehydration of the amide to the nitrile functionality or conversion to the thioamide functionality takes place on one of the protected intermediates. As an alternative, the building block E may be employed in the synthesis in the form of H—E—CSNH$_2$.

Scheme II

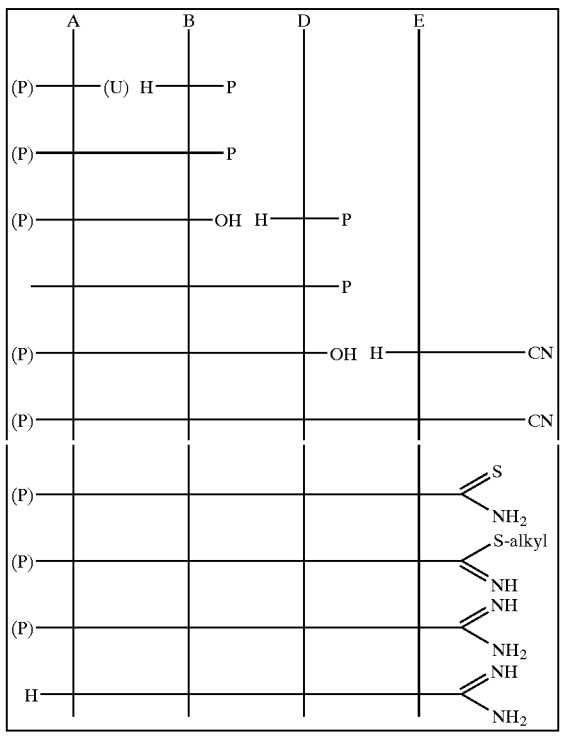

Scheme II describes the linear assemblage of the molecule I by alkylation, reductive amination or Michael addition of H—B—P onto appropriately suitable unprotected or protected A building blocks to give (P)—A—B—P, elimination of the C-terminal protective group to give (P)—A—B—OH, coupling to H—D—P to give (P)—A—B—D—P, elimination of the C-terminal protective group to give (P)—A—B—D—OH, coupling to H—E—CN to give (P)—A—B—D—E—CN and reaction of this intermediate to give the final product as in Scheme I.

Where compounds (P)—A—B—P still have a free NH functionality on B, this must be provided with a suitable protective group before elimination of the C-terminal protective group. The protective groups used in each case must be orthogonal to one another.

As an alternative to the H—E—CN building block, it is also possible to employ H—E—CONH$_2$, H—E—CSNH$_2$, H—E—C(NH)NH$_2$, H—E—C(NP)NH$_2$, H—E—C(NP)NHP, with the coupled intermediate (P)—A—B—D—E—CONH$_2$ in the first case being dehydrated to (P)—A—B—D—E—CN or being converted directly into (P)—A—B—D—E—CSNH$_2$, for example by means of Lawesson's reagent.

Scheme III

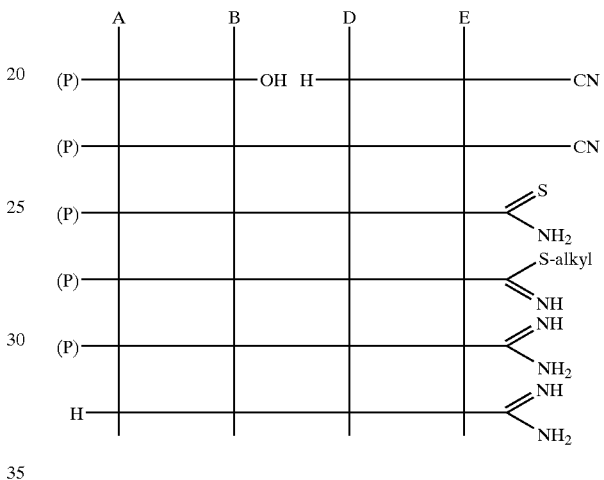

Scheme III describes a very efficient way for preparing compounds I by a convergent synthesis. The appropriately protected building blocks (P)—A—B—OH and H—D—E—CN are coupled together and the resulting intermediate (P)—A—B—D—E—CN is reacted to give the final product as in Scheme I.

It is also possible to employ H—D—E—CONH$_2$ or H—D—E—CSNH$_2$ as an alternative to H—D—E—CN, with the coupled intermediate (P)—A—B—D—E—CONH$_2$ in the first case being dehydrated to (P)—A—B—D—E—CN or being converted into (P)—A—B—D—E—CSNH$_2$.

The N-terminal protective groups employed are Boc, Cbz or Fmoc, preferably Boc, and the C-terminal protective groups are methyl, tert-butyl and benzyl. If a plurality of protective groups is present in the molecule, they must be orthogonal to one another if they are not to be eliminated simultaneously.

The required coupling reactions and the other reactions for introducing and eliminating protective groups are carried out under standard conditions of peptide chemistry (see M. Bodanszky, A. Bodanszky "The Practice of Peptide Synthesis", 2nd edition, Springer Verlag Heidelberg, 1994).

Boc protective groups are eliminated using dioxane/HCl or TFA/DCM, and Cbz protective groups are eliminated by hydrogenolysis or with HF. Hydrolysis of ester functionalities takes place with LiOH in an alcoholic solvent or in dioxane/water. TFA or HCl are used to cleave t-butyl esters.

The reactions were checked by TLC, normally using the following mobile phases:

| A. | DCM/MeOH | 95:5 |
| --- | --- | --- |
| B. | DCM/MeOH | 9:1 |
| C. | DCM/MeOH | 8:2 |
| D. | DCM/MeOH/50% HOAc | 40:10:5 |
| E. | DCM/MeOH/50% HOAc | 35:15:5 |

Where separations by column chromatography are mentioned, these were separations on silica gel using the abovementioned mobile phases.

Reversed phase HPLC separations were carried out with aceto-nitrile/water and HOAc buffer.

All reactions were routinely carried out under a nitrogen atmosphere.

The starting compounds can be prepared by the following methods:

Examples of building blocks A employed for the alkylation are tert-butyl α-bromoacetate, tert-butyl β-bromopropionate, tert-butyl α-bromopropionate, tert-butyl γ-bromobutyrate, tert-butyl α-bromobutyrate, THP-protected bromoethanol, THP-protected γ-bromopropanol, α-bromo-γ-butyrolactone, for the reductive amination are dihydroxyacetone, di-tert-butyl acetonedicarboxylate, and for the Michael addition are tert-butyl acrylate, tert-butyl methacrylate, di-tert-butyl fumarate. Those of said tert-butyl esters which cannot be purchased are prepared by methods similar to G. Uray, W. Lindner, Tetrahedron, 44 1988 357–4362.

B building blocks:

A wide variety of possibilities is available in the literature for the general and specific synthesis of amino acids. A review thereof is provided by, inter alia, Houben-Weyl, Volume E16d/Part 1, pages 406 et seq.

Precursors which were frequently employed were benzophenone imine acetic acid ethyl ester, diethyl-acetamidomalonate and ethyl isonitrileacetate.

Various racemic glycine and alanine derivatives were prepared, for example, starting from ethyl isonitrileacetate and an appropriate ketone or aldehyde (see H.-J. Prätorius, J. Flossdorf, M.-R. Kula Chem. Ber. 108 (1975) 3079).

The syntheses of cyclooctylglycine, cycloheptylglycine, 2-norbonylglycine [sic], adamantylalanine, γ-methylcyclohexylalanine, 4-isopropyl-1-cyclohexylalanine, 4-methyl-1-cyclohexylalanine, 4-methyl-1-cyclohexylglycine, cycloheptylalanine and cyclopentyl-alanine were carried out via the corresponding ethyl 2-formylaminoacrylates (U. Schöllkopf and R. Meyer, Liebigs Ann. Chem. 1977, 1174 and H.-J. Prätorius, J. Flossdorf, M.-R. Kula Chem. Ber. 108 (1985) 3079) starting from ethyl isocyanoacetate with the relevant carbonyl compounds cyclooctanone, cyclo-heptanone, 2-norbornanone, 1-formyladamantane, 1-formyl-1-methylcyclohexane, 1-formyl-4-isopropylcyclohexane, 1-formyl-4-methylcyclohexane and 4-methyl-cyclohexanone, formyl-cyclohexane and formylcyclopentane by the following general methods:

General Method for Synthesizing Ethyl 2-Formylaminoacrylates

A solution of 100 m [sic] of ethyl isocyanoacetate in 50 ml of THF was added dropwise to 100 m [sic] of potassium tert-butoxide in 150 ml of THF at 0 to −10° C. After 15 min at the same temperature 100 mmol of the appropriate carbonyl compound in 50 ml of THF were added, the reaction mixture was allowed to rise slowly to RT, and the solvent was stripped off in a rotary evaporator. The residue was mixed with 50 ml of water, 100 ml of acetic acid and 100 ml of DCM, and the product was extracted with DCM. The DCM phase was dried over $Na_2SO_4$, and the solvent is stripped off in a rotary evaporator. The resulting products were almost pure but could, if necessary, be purified further by column chromatography on silica gel (mobile phases: ether/petroleum ether mixtures).

General Method for Amino Acid Hydrochlorides Starting From the Ethyl 2-Formylaminoacrylates 100 m [sic] of the ethyl 2-formylaminoacrylates were hydrogenated with Pd/C (10%) and hydrogen in 200 ml of glacial acetic acid until the reaction was complete. The catalyst was then filtered off, the acetic acid was stripped off as far as possible in a rotary evaporator, and the residue was refluxed in 200 ml of 50% concentrated hydrochloric acid for 5 h. The hydrochloric acid was stripped off in a rotary evaporator, and the product was dried at 50° C. under reduced pressure and then washed several times with ether. The hydrochlorides resulted as pale colored crystals.

25.0 g of cyclooctylglycine hydrochloride were obtained starting from 18.9 g (150 mmol) of cyclooctanone. 36.2 g of cycloheptylglycine hydrochloride were obtained starting from 22.4 g (200 mmol) of cycloheptanone. 26.6 g of 2-norbonylglycine [sic] hydrochloride were obtained starting from 16.5 g (150 mmol) of 2-norbornanone. 26.0 g of adamantylalanine hydrochloride were obtained starting from 19.7 g (120 mmol) of 1-formyladamantane. 16.6 g of y-methylcyclohexylalanine hydrochloride were obtained starting from 12.6 g (100 mmol) of 1-formyl-1-methylcyclohexane. 25.9 g of 4-methylcyclohexylglycine hydrochloride were obtained starting from 16.8 g (150 mmol) of 4-methylcyclohexanone. 18 g of trans-4-methyl-1-cyclohexylalanine hydrochloride were obtained starting from 15 g of trans-1-formyl-4-methylcyclohexane. 10 g of 3,3-dimethyl-1-cyclohexylalanine hydrochloride were obtained starting from 9 g of 3,3-dimethyl-1-formylcyclohexane.

The aldehyde 1-formyl-3,3-dimethylcyclohexane required for the synthesis was prepared by a method based on that of Moskal and Lensen (Rec. Trav. Chim. Pays-Bas 106 (1987) 137–141).

A solution of n-butyllithium in n-hexane (72 ml, 115 mmol) was added dropwise over the course of 10 min to a stirred solution of diethyl isocyanomethylphosphonate (17 ml, 105 mmol) in 280 ml of anhydrous diethy [sic] ether at −60° C. The resulting suspension was then stirred at −60° C. for 15 min and, over the course of 10 min, a solution of 3,3-dimethylcyclohexanone (13 g, 105 mmol) in 100 ml of anhydrous diethyl ether was added, keeping the temperature below −45° C. The reaction mixture was allowed to reach 0° C. and, after stirring at this temperature for 90 min, 150–200 ml of 38% strength aqueous hydrochloric acid were cautiously added. The mixture was vigorously stirred at room temperature for 15 h to complete the hydrolysis. The organic phase was separated off and washed with 200 ml each of water, saturated sodium bicarbonate solution and saturated sodium chloride solution. It was dried over magnesium sulfate, filtered and concentrated in a rotary evaporator in order to remove the solvent. The resulting residue was employed without further purification as starting material for synthesizing the amino acid.

Cyclopentylglycine was prepared by hydrolysing N-acetyl-(D,L)-cyclopentylglycine with 6N hydrochloric acid, the former having been prepared as described in the literature by J. T. Hill and F. W. Dunn, J. Org. chem. 30(1965), 1321.

Boc-(D)-α-Methylcyclohexylalanine 3.4 g (12.2 mmol) of Boc-(D)-α-methyl-Phe-OH were hydrogenated in 100 ml of MeOH in the presence of 250 mg of 5% Rh on $Al_2O_3$ under 10 bar with hydrogen at 50° C. for 24 h. Filtration and stripping off the solvent resulted in 2.8 g of Boc-(D)-α-methyl-Cha-OH.

$^1$H NMR (DMSO-$d_6$, δ in ppm): 12 (very broad signal, COOH); 1.7–0.8 (25H; 1.35 (s, Boc), 1.30 (s, Me)).

Boc-(3-Ph)-Pro-OH was synthesized by a method similar to that of J. Y. L. Chung et al. (J. Y. L. Chung et al., J.Org.Chem. 55 (1990) 270).

Preparation of Boc-1-Tetralinylglycine

Boc-1-Tetralinylglycine was prepared starting from 1,2-dihydronaphthalene. 1,2-Dihydronaphthalene was initially converted into 1-tetralyl bromide with HBr (similar to J. Med. Chem. 37 (1994) 1586). The bromide was subsequently reacted with diethyl acetamidomalonate and, after hydrolytic cleavage, the resulting α-amino acid was converted into the Boc-protected form under standard conditions. Another possible preparation is described by E. Reimann and D. Voss (E. Reimann, D. Voss, Arch. Pharm. 310 (1977) 102).

Preparation of Boc-(D,L)Dch-OH

Boc-(D,L)-Dpa-OH (1 mmol) was hydrogenated in 12 ml of MeOH together with catalytic amounts of 5% Rh/$Al_2O_3$ under 5 bar. Filtration and removal of the solvent under reduced pressure resulted in the product in quantitative yield. Preparation of H-D,L-Chea-OH 4.0 g of cycloheptylmethyl methanesulfonate (19.39 mmol), prepared from cycloheptylmethanol and methanesulfonyl chloride, were refluxed together with 4.9 g of benzophenone imine glycine ethyl ester (18.47 mmol), 8.9 g of dry, finely powdered potassium carbonate (64.65 mmol) and 1 g of tetrabutylammonium bromide (3 mmol) in 50 ml of dry acetonitrile under an inert gas atmosphere for 10 h. The potassium carbonate was then filtered off, the filtrate was evaporated to dryness, and the crude product was hydrolyzed directly with 20 ml of 2N hydrochloric acid in 40 ml of ethanol, stirring at RT for 1.5 h. The reaction solution was diluted and then benzophenone was extracted with ethyl acetate in the acidic range, and subsequently H-D,L-Chea-OEt was extracted with DCM in the alkaline range (pH=9), and the solution was dried over magnesium sulfate and concentrated in a rotary evaporator. Yield 3.7 g=95% of theory.

Boc-(D,L)-(3,4,5-(MeO)$_3$)Phe-OH was prepared by alkylation of benzophenone imine glycine ethyl ester with trimethoxybenzyl chloride, subsequent introduction of the Boc protective group and ester hydrolysis.

H-(D,L)-P,P-Me$_2$Cha-OH was prepared by the method of U. Schöllkopf, R. Meyer, L. Ann. Chem. (1977) 1174–82.

Said amino acids were converted with di-tert-butyl dicarbonate in water/dioxane by conventional methods into the Boc-protected form in each case and subsequently recrystallized from ethyl acetate/hexane mixtures or purified by column chromatography on silica gel (mobile phases: ethyl acetate/petroleum ether mixtures).

The Boc-protected amino acids were employed as B building blocks as shown in Scheme I.

Said amino acids as B building blocks were also in some cases converted into the corresponding benzyl esters and linked to the appropriately protected A building blocks. In the case of compounds with an N—H functionality which was still free, this was subsequently protected with a Boc group, the benzyl ester group was removed by hydrogenation, and the building block A—B—OH was purified by crystallization, salt precipitation or column chromatography. This route is described by way of example for tBuOOC—CH$_2$—(Boc)(D)Cha-OH below.

Synthesis of (D)-Cyclohexylalanine Benzyl Ester

A suspension of 100 g (481 mmol) of (D)-cyclohexylalanine hydrochloride, 104 g (962 mmol) of benzyl alcohol and 109.7 g (577 mmol) of p-toluenesulfonic acid monohydrate in 2200 ml of toluene was slowly heated to reflux with a water separator. Evolution of hydrogen chloride and dissolving of the suspension to give a clear solution were observed in the temperature range 80–90° C. When no further water separated out (about 4 h), 500 ml of toluene were distilled out, the reaction mixture was allowed to cool overnight, and the resulting residue was filtered off and washed twice with 1000 ml of hexane each time. The resulting residue (195 g) was then suspended in 2000 ml of dichloromethane and, after addition of 1000 ml of water, adjusted to pH 9–9.5 by gradual addition of 50% strength sodium hydroxide solution while stirring. The organic phase was separated off, washed twice with 500 ml of water each time, dried over sodium sulfate and filtered to remove desiccant, and concentration of the filtrate resulted in 115 g (94%) of the title product as pale oil.

N-(tert-Butyloxycarbonylmethylene)-(D)-cyclohexylalanine Benzyl Ester 115 g (440 mmol) of (D)-cyclohexylalanine benzyl ester were dissolved in 2000 ml of acetonitrile and, at room temperature, 607.5 g (4.40 mol) of potassium carbonate and 94.3 g (484 mmol) of tert-butyl bromoacetate were added, and the mixture was stirred at this temperature for 3 days. Carbonate was filtered off, washed with acetonitrile, the mother liquor was concentrated (30° C., 20 mbar), the residue was taken up in 1000 ml of methyl tert-butyl ether, and the organic phase was extracted with 5% strength citric acid and saturated sodium bicarbonate solution. The organic phase was dried over sodium sulfate, filtered to remove desiccant and concentrated, and the resulting oil (168 g) was employed directly in the next reaction.

N-Boc-N-(tert-Butyloxycarbonylmethylene)-(D)-cyclohexylalanine Benzyl Ester

The oil (168 g, 447 mmol) obtained in the previous synthesis was dissolved in 1400 ml of acetonitrile and, after addition of 618 g (4.47 mmol) of potassium carbonate powder and 107.3 g (492 mmol) of di-tert-butyl dicarbonate, stirred at room temperature for 6 days. The potassium carbonate was filtered off with suction, washed with about 1000 ml of acetonitrile, and the filtrate was concentrated. 230 g of the required product were obtained.

N-Boc-N-(tert-Butyloxycarbonylmethylene)-(D)-cyclohexylalanine Cyclohexylammonium Salt 115 g of N-Boc-N-(tert-butyloxycarbonylmethylene)-(D)-cyclohexylalaine [sic] benzyl ester were dissolved in 1000 ml of pure ethanol and hydrogenated in the presence of 9 g of 10% Pd on active carbon with hydrogen under atmospheric pressure at 25–30° C. for 2 h. Filtration and removal of the solvent in a rotary evaporator resulted in 100 g (260 mmol) of a yellow oil which was taken up in 1600 ml of acetone and heated to reflux. The heating bath was removed, and a solution of 27 g (273 mmol) of cyclohexylamine in acetone was quickly added through a dropping funnel. The required salt crystallized out on cooling the reaction mixture to room temperature. The solid was filtered off, washed with 200 ml of acetone and, for final purification, recrystallized once more from acetone. Drying of the residue in a vacuum oven at about 30° C. resulted in 70.2 g of the required salt as white powder.

N-Boc-N-(tert-Butyloxycarbonylmethylene)-(D)-cyclohexylglycine cyclohexylammonium salt was prepared analogously from cyclohexylglycine as precursor. The N-Boc-N-(tert-butyloxycarbonylmethylene)-(D)-cycloheptylglycine and N-Boc-N-(tert-butyloxycarbonylmethylene)-(D)-cyclopentylglycine derivatives were prepared from the corresponding cycloheptyl- and cyclopentylglycine compounds.

N-Boc-N-(tert-Butyloxycarbonylethylene)-(D)-cyclohexylalanine Cyclohexylammonium Salt a) tert-Butyl 3-Bromopropionate In a countercurrent of nitrogen, 16.64 g (109 mmol) of bromopropionic acid, 150 ml of condensed 2-methylpropene and 2 ml of concentrated sulfuric acid were added at –30° C. into an autoclavable glass vessel, the autoclave was sealed tightly and the mixture was stirred for 72 hours at room temperature. For working up, the reaction vessel was again cooled to –30° C. and the reaction solution was poured carefully into 200 ml of an ice-cold saturated sodium hydrogen carbonate solution. Excess 2-methylpropene was evaporated with stirring, the residue was extracted three times with in each case 50 ml of dichloromethane, and the combined organic phases were dried over sodium sulfate, filtered to remove desiccant and concentrated under a water pump vacuum. The oily residue was purified by column chromatography (mobile phase n-hexane, later n-hexan/diethyl ether 9:1). This resulted in 18.9 g of the title compound.

b) N-(tert-Butyloxycarbonylethylene)-(D)-cyclohexylalanine Benzyl Ester 49.4 g (189 mmol) of (D)-cyclohexylalanine benzyl ester were dissolved in 250 ml of acetonitrile, the solution was treated with 31.6 g (151 mmol) of tert-butyl bromopropionate at room temperature and the mixture was refluxed for 5 days. The mixture was filtered to remove the precipitate formed and this was washed repeatedly with acetonitrile, the filtrate was concentrated under a water pump vacuum, the residue was taken up in 350 ml of dichloromethane, and the organic phase was extracted with 5% strength citric acid and saturated sodium hydrogen carbonate solution. The organic phase was dried over sodium sulfate, filtered to remove desiccant and concentrated. The oily residue was purified by column chromatography (mobile phase dichloromethane, later dichloromethane/methanol 95:5). This resulted in a slightly impure oil which was employed directly in the next reaction.

c) N-Boc-N-(tert-Butyloxycarbonylethylene)-(D)-cyclohexylalanine Benzyl Ester

The oil obtained in the synthesis above (30 g, max. 70 mmol) was dissolved in 150 ml of acetonitrile, and the solution was treated with 28 ml (160 mmol) of diisopropylethylamine and 19.2 g (88 mmol) of di-tert-butyl dicarbonate and stirred for 3 days at room temperature. The reaction mixture was concentrated under a water pump vacuum in a rotary evaporator, the residue was taken up in n-hexane, the mixture was washed 5 times using in each case 3 ml of a 5% strength citric acid solution, the combined organic phases were dried over sodium sulfate, filtered to remove desiccant and concentrated, and the residue was subjected to separation by column chromatography (mobile phase hexane/ethyl acetate 95:5). The results were 32.66 g (64 mmol) of the required product.

d) N-Boc-N-(tert-Butyloxycarbonylethylene)-(D)-cyclohexylalanine Cyclohexylammonium Salt 32.66 g (64 mmol) of N-Boc-N-(tert-butyloxycarbonylethylene)-(D)-cyclohexylalanine benzyl ester were dissolved in 325 ml of pure ethanol and hydrogenated with hydrogen for 14 hours under atmospheric pressure at 25–30° C. in the presence of 3 g of 10% pure Pd on active charcoal. Filtration of the solution through Celite®, washing of the latter with ethanol and removal of the solvent in a rotary evaporator resulted in 26.7 g of a yellow oil which was taken up in acetone and heated to reflux. The heating bath was removed, and a solution of 7 g (70 mmol) of cyclohexylamine in acetone was quickly added through a dropping funnel. The required salt crystallized out on cooling the reaction mixture to room temperature. The solid was filtered off, washed with 25 ml of acetone and, for final purification, recrystallized once more from acetone. Drying of the residue in a vacuum oven at 30° C. resulted in 26.6 g (54 mmol) of the required salt as white powder.

N-Boc-N-(tert-butyloxycarbonylmethylene)-(D)-cyclohexylalanyl-3,4-dehydroproline:

a) N-Boc-Pyr-OH (5 g, 23.45 mmol) was dissolved in MeOH (50 ml), and HCl in dioxane (4N, 30 ml) was added. The mixture was subsequently heated under reflux for 12 hours. Removal of the solvent in a rotary evaporator resulted in H-Pyr-OMe-hydrochloride as product. Yield: 3.84 g (100%).

b) N-(t-BuO2C—CH$_2$)-N-Boc-(D)-Cha-OH (8 g, 20.75 mmol) was dissolved in dichloromethane (75 ml), and ethyldiisopropylamine (15.5 ml, 89.24 mmol) were added at –10° C. After the mixture had been stirred for 5 minutes at this temperature, a solution of H-Pyr-OMe hydrochloride (3.4 g, 20.75 mmol) in dichloromethane (25 ml) was added dropwise. A solution of propanephosphonic anhydride in ethyl acetate (50% strength, 20 ml, 26.96 mmol) was subsequently added dropwise and stirred for 2 h at –10 to 0° C. The batch was diluted with dichloromethane and washed with saturated sodium hydrogen carbonate solution (2×80 ml), 5% strength citric acid solution (2×15 ml) and saturated sodium chloride solution (1×20 ml). The organic phase was dried over sodium sulfate and the solvent was removed in a rotary evaporator. The crude product was purified by means of flash chromatography (silica gel, dichloromethane/methanol 95/5). Yield: 6.2 g (60%).

c) N-(t-BuO$_2$C—CH$_2$)-N-Boc-(D)-Cha-Pyr-OMe (5.5 g, 11.12 mmol) was dissolved in dioxane (40 ml), aqueous sodium hydroxide solution (IN, 22.2 ml, 22.24 mmol) was added, and the mixture was stirred for 2 hours at room temperature. The dioxane was removed in a rotary evaporator, and the aqueous phase was washed with ethyl acetate and acidified to pH 1–2 with potassium hydrogen sulfate solution (20% strength). The aqueous phase was extracted with dichloromethane and the combined organic phases were dried over sodium sulfate. Yield: 5 g (94%), colorless foam. Recrystallization of n-hexane saturated with water resulted in the corresponding carboxylic acid as colorless crystals (m.p.=158–160° C.).

N-Boc-N-(tert-butyloxycarbonylmethylene)-(D)-cyclohexylglycyl-3,4-dehydroproline:

This compound was synthesized analogously from N-Boc-N-(tert-butyloxycarbonylmethylene)-(D)-cyclohexylglycine and 3,4-dehydroproline methyl ester.

N-Boc-N-(tert-butyloxycarbonylmethylene)-(D)-cyclohexylalanylproline:

a) N-(t-BuO$_2$C—CH$_2$)-N-Boc-(D)-Cha-OH (20 g, 51.88 mmol) was dissolved in dry methylene chloride (100 ml). After cooling to –5° C., N-ethyldiisopropylamine (90 ml, 518.88 mmol) was added dropwise and stirring was continued for 5 minutes.

H-Pro-OBn×HCl (12.54 g, 51.88 mmol) was subsequently added at –5° C. and, after the mixture had been stirred for 5 minutes, 50% strength propanephosphonic anhydride solution in ethyl acetate (45.1 ml, 62.26 mmol), diluted with methylene chloride (45 ml), was added dropwise in the course of 30 minutes. After the mixture had been stirred for 1 hour at 0–5° C., it was slowly brought to RT and stirred for 12 hours at RT. The batch was diluted with methylene chloride and washed in succession with saturated sodium hydrogen carbonate solution, 5% strength citric acid solution and saturated sodium chloride solution. After drying over sodium sulfate, the solvent was distilled off in vacuo. Yield: 28.9 g (pale yellow oil, 97%).

b) The product obtained as described in a) (28.5 g, 49.76 mmol) was dissolved in methanol (650 ml), 10% pure Pd on charcoal (1.8 g) was added, and the mixture was hydrogenated at RT and under 1 atmosphere of hydrogen. The catalyst was subsequently removed by filtration through Celite® and the filtrate was concentrated in vacuo. Yield: 22.2 g (colorless foam, 92%).

N-Boc-N-(tert-butyloxycarbonylmethylene)-(D)-cyclohexylglycylproline:

This compound was prepared analogously from N-Boc-N-(tert-butyloxycarbonylmethylene)-(D)-cyclohexylglycine and proline methyl ester.

D building blocks:

The compounds employed as D building blocks, (L)-proline, (L)-pipecolic acid and (L)-azetidinecarboxylic acid, are commercially available, either as free amino acids, as Boc- protected compounds or as the corresponding methyl esters. If (L)-3,4-dehydroproline or (D,L)-4,5-dehydropipecolic acid, or a corresponding, protected derivative, were employed as D building blocks, the compounds prepared were generally hydrogenated in the last step to give the corresponding proline derivatives. (L)-3,4-Dehydroproline (H-Pyr-OH) is commercially available, (D,L) 4,5-dehydropipecolic acid (H-(D,L)-Dep-OH) can be prepared by the methods of A. Burgstahler, C. E. Aiman J. Org. Chem. 25 (1960), 489 or C. Herdeis, W. Engel Arch. pharm 326 (1993), 297.

The E building blocks were synthesized as follows:

5-Aminomethyl-2-cyanothiophene:

This building block was synthesized as described in WO 95/23609.

4-Aminomethyl-2-cyanothiophene a) 2-Bromo-4-formylthiophene 36 g (320 mmol) of 3-formylthiophene were dissolved in 600 ml of methylene chloride, the solution was cooled to 5° C., 100 g (750 mmol) of aluminum trichloride were added, a little at a time, and the reaction mixture was subsequently refluxed. A solution of 59 g (19 ml, 360 mmol) of bromine in 40 ml of methylene chloride was added dropwise over the course of 45 minutes and the mixture was allowed to after-react under reflux for 4 hours. After cooling, the reaction solution was poured onto 600 g of ice-water and extracted with methylene chloride, and the organic phase was washed with saturated sodium hydrogen carbonate solution, dried over magnesium sulfate and concentrated in a rotary evaporator in vacuo. 64.5 g of crude product resulted, which was purified by means of column chromatography (silica gel, methylene chloride/petroleum ether). A total of 56.5 g of slightly impure product were obtained.

b) 2-Cyano-4-formylthiophene 7.6 g (85 mmol) of copper(I) cyanide were added to a solution of 13.53 g (70.82 mmol) of 2-bromo-4-formylthiophene in 25 ml of DMF and the reaction mixture was refluxed for 3.5 hours, during which process the suspension, which originally was pale green in color, turned into a black solution. After addition of water, the reaction mixture was extracted repeatedly with ethyl acetate, and the organic phases were combined, washed with saturated sodium chloride solution, dried over sodium sulfate and concentrated under slightly reduced pressure. Treatment of the residue (7 g) with ether resulted in 1.6 g of pure product. The mother liquor together with the crude products from other batches was purified by chromatography. (Silica. gel, methylene chloride/petroleum ether 1:1). In total, 56.5 g of 2-bromo-4-formylthiophene were reacted to give 2-cyano-4-formylthiophene, resulting in 12.6 g of pure product (yield 31%).

c) 2-Cyano-4-hydroxymethylthiophene 3.47 g (91.8 mmol) of sodium borohydride were added, a little at a time, to a suspension of 12.6 g (91.8 mmol) of 2-cyano-4-formylthiophene in 200 ml of ethanol and stirred at room temperature for 2 hours, during which process the reaction mixture slowly formed a clear solution. After concentration in vacuo, the residue was taken up in ethyl acetate, washed in succession with saturated sodium chloride solution, 5% strength citric acid and saturated sodium chloride solution, and the organic phase was dried using sodium sulfate and concentrated in vacuo. 11.7 g of almost pure product resulted (yield 91.5%).

d) 4-Bromomethyl-2-cyanothiophene 11.7 g (84.07 mmol) of 2-cyano-4-hydroxymethylthiophene together with 24.1 g (91.87 mmol) of triphenylphosphine were dissolved in 100 ml of-THF at room temperature, and 30.47 g (91.87 mmol) of tetrabromomethane were added, a little at a time, with cooling (ice bath). After stirring for 3 hours at room temperature, the mixture was concentrated in vacuo and purified by chromatography over silica gel (methylene chloride/petroleum ether). 18.8 g of crystalline pale yellow product which still contained petroleum ether resulted.

e) 4-N,N-bis(tert-Butoxycarbonyl)aminomethyl-2-cyanothiophene 18.81 g of 4-bromomethyl-2-cyanothiophene (crude product, maximum 84.07 mmol) were dissolved in 160 ml of THF, the solution was cooled to 5° C., and 3.07 g (102.4 mmol) of 80% sodium hydride suspension were added, a little at a time. 22.25 g (102.4 mmol) of di-tert-butyl iminodicarboxylate, dissolved in 160 ml of THF, were subsequently added dropwise at 5° C. and the mixture was then stirred overnight at room temperature. Since TLC revealed that the reaction was incomplete, the batch was heated for 4.5 hours at 30–35° C.

After cooling to 0–5° C., 33 ml of saturated ammonium chloride solution were slowly added dropwise, THF was distilled off in vacuo, the residue was extracted repeatedly with ethyl acetate, and the ethyl acetate phases were washed with saturated sodium chloride solution, dried over sodium sulfate and evaporated in a rotary evaporator. The red viscous residue (34.61 g) was employed in the subsequent reaction as crude product.

f) 4-Aminomethyl-2-cyanothiophene hydrochloride 34.61 g of 4-N,N-bis(tert-butoxycarbonyl)aminomethyl-2-cyano-thiophene (crude product, maximum 84.07 mmol) were dissolved in 600 ml of ethyl acetate, and the solution was cooled to 0–5° C., saturated with HCl gas and warmed to room temperature. After 3 hours, the resulting suspension was evaporated in a rotary evaporator, the product was codistilled repeatedly with methylene chloride, and the residue was extracted by stirring with ether and dried in vacuo. 13.85 g of product resulted as a pale powder. Yield over two steps: 94.3%.

2-Aminomethyl-4-cyanothiophene a) 4-Cyanothiophene-2-carbaldehyde 49.3 g (258.05 mmol) of 4-bromothiophene-2-carbaldehyde and 27.8 g (310.41 mmol) of copper(I) cyanide were suspended in 130 ml of absolute DMF and the suspension was refluxed for 8 hours. The solvent was evaporated in vacuo in a rotary evaporator at 400C, the residue was suspended in ethyl acetate and the suspension was transferred into a Soxleth apparatus. The residue was extracted overnight, the yellow solution was dried over sodium sulfate and evaporated in vacuo in a rotary evaporator, and the resulting yellow solid was recrystallized frome ether. 25.3 g of product resulted (80% of theory).

b) 4-Cyanothiophene-2-carbaldehyde oxime 11.6 g (84.6 mmol) of 4-cyanothiophene-2-carbaldehyde were dissolved in 140 ml of methanol and 12.3 g (116.1 mmol) of sodium carbonate were added. 6.5 [lacuna] (93.5 mmol) of hydroxylamine hydrochloride were subsequently added at 15° C. with cooling, a little at a time, and the mixture was stirred for 2 hours at 10° C. After 80 ml of water had been added, the reaction mixture was extracted five times using in each case 50 ml of diethyl ether, the organic phase was dried over sodium sulfate and the solvent was removed in vacuo. 12.5 g of the required product resulted as a yellow crystal powder (96% of theory).

c) 2-Aminomethyl-4-cyanothiophene Hydrochloride 11.22 g (171.64 mmol) of fine zinc dust were carefully added, in several small portions, to a solution of 4.65 g (30.60 mmol) of 4-cyanothiophene-2-carbaldehyde oxime in 50 ml of trifluoroacetic acid, cooled to 0–5° C., in such a way that the temperature did not climb above 15° C. After stirring for 3 hours at room temperature, excess zinc was decanted off, most of the trifluoroacetic acid was removed in vacuo (oil pump), the remaining oil was cooled to 0° C., and a mixture of 150 ml of 3N aqueous sodium hydroxide solution and 2l of methylene chloride, pre-cooled to 0° C., was added, a little at a time. After insolubles were removed by filtration, the organic phase was separated off, the aqueous phase was extracted eight times using 20 ml of methylene chloride, the collected organic phases were dried over sodium sulfate, and 20 ml of 6M methanolic hydrochloric acid were subsequently added, with ice-cooling. During this process, the product precipitated in the form of the hydrochloride as a white solid, the suspension being cooled overnight to 4° C. to bring crystallization to completion. 2.2 g of product resulted as colorless needles (50% of theory).

5-Aminomethyl-3,4-dimethylthiophene-2-carboxamide Hydrochloride 19 g (105.42 mmol) of 5-cyano-3,4-dimethylthiophene-2-carboxamide were suspended in 760 ml of methanol and 110 ml of 2N hydrochloric acid solution, 9.5 g of Pd on charcoal (10%) were added, and the mixture was hydrogenated at room temperature. After 4.7l of hydrogen had been taken up (4 h), methanol was distilled out in vacuo, and the aqueous phase was extracted three times with ethyl acetate and subsequently freeze-dried. 16.3 g of the required product resulted as a white solid (70.4% of theory).

5-Aminomethylisoxazole-3-carboxamide a) Ethyl 5-Chloromethylisoxazole-3-carboxylate 21.2 g (210 mmol) of triethylamine were added dropwise with stirring to a mixture, cooled to 10–15° C., of 30 g (198 mmol) of ethyl 2-chloro-2-hydroxyiminoacetate and 150 ml of propargyl chloride, stirring was continued for 1 hour at room temperature, water was subsequently added, the mixture was extracted with ether, and the organic phase was dried over magnesium sulfate and evaporated in vacuo in a rotary evaporator. The residue was distilled in vacuo at 0.5 torr, the product distilling over at 116–122° C.

b) 5-Chloromethylisoxazole-3-carboxylic Acid 14 g (250 mmol) of potassium hydroxide were added to 47.3 g (250 mmol) of ethyl 5-chloromethylisoxazole-3-carboxylate in 150 ml of ethanol, and the reaction mixture was stirred for 6 hours at 60–70° C. After cooling, the mixture was concentrated in vacuo, the residue was taken up in water and extracted with ether, the aqueous phase was acidified with hydrochloric acid and subsequently extracted repeatedly with ether, and the ether phase was dried over sodium sulfate and concentrated in vacuo (oil pump, 50° C.). 31 g of the required product resulted (77% of theory)

c) 5-Chloromethylisoxazole-3-carboxylic Acid Chloride 120 g (743 mmol) of 5-chloromethylisoxazole-3-carboxylic acid together with 500 ml of thionyl chloride and 2 drops of pyridine were refluxed for 10 hours, subsequently concentrated in vacuo and then distilled at 20 torr. The product distilled at 125–133 0C. 78 g resulted (58% of theory)

d) 5-Chloromethylisoxazole-3-carboxamide

Ammonia was passed for 1 hour at 10–15° C. into a solution of 10 g (55.56 mmol) of 5-chloromethylisoxazole-3-carboxylic acid chloride in 100 ml of methylene chloride and stirring was subsequently continued at room temperature for 1 hour. After the solution had cooled to 0° C., the precipitate was filtered off with suction and washed with a little cold methylene chloride, and the residue was extracted twice by stirring with water to remove the ammonium salts. Drying in vacuo resulted in 6.58 g of pure product as a pale powder (74% of theory)

e) 5-Aminomethylisoxazole-3-carboxamide Hydrochloride 2.44 g (15.2 mmol) of 5-chloromethylisoxazole-3-carboxamide were added to a mixture of 100 ml of concentrated ammonia solution and 72 ml of methanol, and the reaction solution was warmed to 40° C. and constantly saturated with ammonia gas during this process. After 6 hours, the precursor was reacted. The methanol was removed in vacuo, and the aqueous phase was extracted twice using methylene chloride and subsequently evaporated to dryness in vacuo under mild conditions in a rotary evaporator. The white solid residue was employed in the coupling reactions in the form of the crude product.

2-Aminomethyloxazole-4-thiocarboxamide and 2-aminomethylthiazole-4-thiocarboxamide were prepared by the method of G. Videnov, D. Kaier, C. Kempter and G. Jung Angew. Chemie (1996) 108, 1604, where the N-Boc-protected compounds described therein were deprotected using etheric hydrochloric acid in methylene chloride.

4-Aminomethylthiazole-2-thiocarboxamide a) Monothiooxalic Diamide

Monothiooxalic diamide was prepared starting from ethyl thiooxamidate by the method of W. Walter, K.-D. Bode Liebigs Ann. Chem. 660 (1962), 74–84.

b) 2-Carbamoyl-4-chloromethylthiazole 10 g (96 mmol) of ethyl thiooxamidate were introduced into 170 ml of n-butanol, 26 g (204 mmol) of 1,3-dichloroacetone were added, and the mixture was heated for 90 minutes at 112° C. under nitrogen. The reaction mixture was then concentrated in vacuo and the residue was extracted by stirring with n hexane [sic] (120 ml). 10 g of pure product resulted.

c) 4-Boc-Aminomethyl-2-carbamoylthiazole 10 g (56.6 mmol) of 2-carbamoyl-4-chloromethylthiazole were introduced into an ammonia-saturated solution of 350 ml of methanol and 80 ml of 25% strength aqueous ammonia solution. The reaction mixture was warmed for 6 hours at 40–42° C. while continuously saturating with ammonia, then concentrated in vacuo and codistilled with methanol, and the residue was subsequently extracted by stirring first with ether and then with acetone. 7.6 g of crude product which still contained a small amount of ammonium chloride were isolated. To remove this secondary product, the crude product was reacted with $(Boc)_2O$ in aqueous dioxane solution, and the protected compound was purified by means of column chromatography. This resulted in 4.95 g of pure product.

d) 4-Boc-Aminomethyl-2-cyanothiazole 4.95 g (19.24 mmol) of 4-Boc-aminomethyl-2-carbamoylthiazole were introduced into 90 ml of methylene chloride and 16.7 ml (97.44 mmol) of diisopropylethylamine, the mixture was cooled to 0° C., a solution of 6.35 ml of trifluoroacetic anhydride in 10 ml of methylene chloride was added dropwise at 0 to 5° C., and the mixture was subsequently warmed to room temperature (TLC check). Then, 25 ml of water were added, the mixture was stirred for 30 minutes at room temperature and brought to pH 2.5 with 10% strength citric acid solution, and the organic phase was washed repeatedly, dried using magnesium sulfate and concentrated in vacuo. 5.4 g of viscous, pale brown crude product resulted, which were employed in the next step without further purification.

e) 4-Boc-Aminomethyl-2-thiocarbambylthiazole

The crude product resulting from d) (max 19.24 mmol) was dissolved in 65 ml of pyridine and 5 ml of triethylamine, saturated with hydrogen sulfide and left to stand at room temperature over the weekend. The reaction mixture was then evaporated in vacuo in a rotary evaporator, the residue was taken up in a mixture of ether and ethyl acetate, and the mixture was washed with 10% strength citric acid solution and water, dried over magnesium sulfate and evaporated in vacuo in a rotary evaporator. 6.0 g resulted as a pale yellow solid foam.

f) 4-Aminomethyl-2-thiocarbamoylthiazole Hydrochloride

The product resulting from the above experiment was taken up in 100 ml of methylene chloride, 30 ml of approx. 5-molar etheric hydrochloric acid solution were added, and the mixture was stirred overnight at room temperature. The reaction mixture was then evaporated to dryness in vacuo in a rotary evaporator, codistilled repeatedly with ether and subsequently extracted by stirring with methylene chloride. 4.15 g of the required product resulted as a pale yellow amorphous substance.

4-Amidino-2-(N-Boc-aminomethyl)-5-methylthiazole×HOAc a) α-Acetylglycine Methyl Ester Hydrochloride Potassium tert-butylate (17.8 g, 157.9 mmol) was introduced into THF (120 ml), and a solution of N-diphenylmethylideneglycine methyl ester (40 g, 157.9 mmol) in THF (60 ml) was added at −70° C. After the yellowish solution had been stirred for 30 minutes at this temperature, it was added dropwise at −70° C. to a solution of acetyl chloride (12.4 g, 157.9 mmol) in THF (70 ml). After the mixture had been stirred at this temperature for 1.75 hours, 3N HCl (160 ml) was added, and the yellowish suspension was stirred for a further 10 minutes at room temperature. The THF was removed at room temperature on a rotary evaporator, and the remaining aqueous phase was washed 3× with diethyl ether. The aqueous phase was freeze-dried and the residue was extracted by stirring with methanol. The methanolic solution of the product was concentrated on a rotary evaporator at 35° C. Yield: 26.4 g (157.9 mmol, quant., yellowish solid).

b) BOC-Gly-(α-Acetyl-Gly)-OMe [sic]

BOC-Gly-OH [sic] (24.05 g, 137.27 mmol) were [sic] introduced into THF (400 ml), and triethylamine (13.87 g, 137.19 mmol) was added. The colorless solution was cooled to −20° C., and a solution of isobutyl chloroformate (18.75 g, 137.28 mmol) in THF (20 ml) was added dropwise at this temperature. The colorless suspension was stirred for a further 30 minutes at −20° C., and a-acetylglycine methyl ester hydrochloride (23.0 g, 137.3 mmol) was then added portionwise. After the mixture had been stirred for 30 minutes at −20° C., a solution of triethylamine (13.87 g, 137.19 mmol) in THF (20 ml) was added dropwise in the course of 45 minutes. After the mixture had been stirred for 4 hours at −20° C., stirring was continued for another 12 hours at RT. The residue was filtered off with suction and-washed with THF, and the combined THF phases were concentrated on a rotary evaporator.

Yield: 44.1 g (pale brown oil). $^1$H NMR (270 MHz, $CDCl_3$) δ=1.45 (s, 9H), 2.40 (s, 3H), 3.85 (s, 3H), 3.90 (d, J=6.5 Hz, 2H), 5.25 (d, J=6.5 Hz, 1H), 7.30 (sbr, 1H).

c) Methyl 2-(N-Boc-Aminomethyl)-5-methylthiazole-4-carboxylate

BOC-Gly-(a-acetyl-Gly)-OMe [sic] (39.8 g, 138.2 mmol) was introduced into THF (400 ml), and Lawesson's reagent (96.6 g, 238.8 mmol) was added portionwise at room temperature. The yellowish solution was then refluxed for 1.5 hours. The THF was removed on a rotary evaporator. The residue (reddish-brown oil) was extracted by stirring with diethyl ether (600 ml). The ether phase was decanted off from the undissolved brownish oil .and washed in succession with 5% strength citric acid (2×), saturated $NaHCO_3$ solution (9×) and water (2×). After drying ($MgSO_4$) the solvent was removed on a rotary evaporator. Yield: 22.0 g (77 mmol, 56%, brownish solid).

$^1$H NMR (270 MHz, $CDCl_3$) δ=1.50 (s, 9H), 2.75 (s, 3H), 3.95 (s, 3H), 4.55 (d, J=6.5 Hz, 2H), 5.45 (t, J=6.5 Hz, 1H). (Main rotamer relative to the Boc group).

d) 2-(N-Boc-Aminomethyl)-5-methylthiazole-4-carboxylic Acid

Methyl 2-(N-Boc-aminomethyl)-5-methylthiazole-4-carboxylate (22.0 g, 77 mmol) was dissolved in ethanol (100 ml), and a solution of LiOH (2.2 g, 92 mmol) in water (50 ml) was added. After the mixture had been stirred for 30 minutes at room temperature, the ethanol was removed on a rotary evaporator and the solution which remained was diluted with water (70 ml). The aqueous phase was washed with ethyl acetate (3×) and brought to pH 2 with 20% strength NaHSO$_4$ solution, during which process a pale brown oil separated out. The aqueous phase was extracted with dichloromethane and the combined organic extracts were dried (MgSO$_4$) and concentrated in vacuo. The pale brown residue was extracted by stirring in diisopropyl ether. The colorless precipitate which remained was filtered off with suction and washed with diisopropyl ether. Yield: 6.9 g (25.4 mmol, 33%, colorless solid).

$^1$H NMR (270 MHz, DMSO-d$_6$) δ=1.40 (s, 9H), 2.65 (s, 3H), 4.30 (d, J=6.5 Hz, 2H), 7.80 (t, J=6.5 Hz, 1H).

e) 2-(N-Boc-Aminomethyl)-5-methylthiazole-4-carboxamide 2-(N-Boc-Aminomethyl)-5-methylthiazole-4-carboxylic acid (6.8 g, 25 mmol) was dissolved in THF (100 ml), and triethylamine (2.53 g, 25 mmol) was added. After the mixture had been cooled to −20° C., a solution of isobutyl chloroformate (3.41 g, 25 mmol) in THF (10 ml) was added dropwise. After the mixture had been stirred for 30 minutes at −20° C., ammonia gas was passed into the pale brown suspension for 45 minutes. The mixture was then warmed to room temperature. The residue was filtered off with suction and extracted with THF, and the filtrates were concentrated.

Yield: 6.9 g (25 mmol, quant.). $^1$H NMR (270 MHz, DMSO-d$_6$) δ=1.40 (s, 9H), 2.65 (s, 3H), 4.30 (m, 2H), 7.40 (sbr, 1H), 7.50 (sbr, 1H), 7.80 (t, J=6.5 Hz, 1H).

f) 4-Cyano-2-(N-Boc-aminomethyl)-5-methylthiazole 2-(N-Boc-Aminomethyl)-5-methylthiazole-4-carboxamide (6.8 g, 25 mmol) was introduced into dichloromethane (120 ml). After the mixture had cooled to 0° C. diisopropylethylamine (15.84 g, 122.8 mmol) was added dropwise. Then, a solution of trifluoroacetic anhydride (8.25 g, 39.3 mmol) in dichloromethane (20 ml) was added dropwise at −5° C. in the course of 30 minutes. After the mixture had been stirred for 30 minutes at 0° C., it was warmed to room temperature, and stirring was continued for another 12 hours. The mixture was diluted with dichloromethane (100 ml) and washed with 20% strength citric acid, saturated NaHCO3 [sic] solution and saturated NaCl solution. The organic phase was dried (MgSO$_4$) and concentrated in vacuo. Yield: 6.3 g (25 mmol, quant.).

g) 4-Amidino-2-(N-Boc-aminomethyl)-5-methylthiazole× CH$_3$COOH

4-Cyano-2-(N-Boc-aminomethyl)-5-methylthiazole (5.5 g, 21.74 mmol) was dissolved in methanol (15-ml), and N-acetylcysteine (4.1 g, 25.12 mmol) was added. The mixture was then warmed to 60° C., and ammonia was passed in for 22 hours. The batch was diluted with methanol and passed over an acetate ion exchanger. The methanol was removed on a rotary evaporator and the residue extracted by stirring with acetone. The colorless residue was filtered off with suction and dried in vacuo. Yield: 4.75 g (14.4 mmol, 66%, colorless solid).

$^1$H NMR (400 MHz, DMSO-d$_6$)δ=1.40 (s, 9H), 1.80 (s, 3H), 2.60 (s, 3H), 4.35 (d, J=6.5 Hz, 2H), 7.90 (t, J=6.5 Hz, 1H).

2-Aminomethyl-5-amidino-4-methylthiazole×2 HCl a) N-BOC-Glycine [sic] Thioamide

N-BOC-Glycinonitrile [sic] (12.0 g, 76.8 mmol) and diethylamine (0.16 ml, 2.1 mmol) were dissolved in toluene (100 ml). The solution was cooled to −10° C., saturated with hydrogen sulfide and subsequently stirred overnight at room temperature. The precipitate formed was filtered off with suction and washed with toluene. The product was dried in vacuo at 45° C. Yield: 13.2 g (69.4 mmol, 90.3%, yellowish solid).

$^1$H NMR (270 MHz, DMSO-d$_6$) δ=1.40 (s, 9H), 3.80 (d, J=7 Hz, 2H), 7.05 (t, J=7 Hz, 1H), 9.0 (sbr, 1H), 9.65 (sbr, 1H).

b) Methyl 2-(N-BOC-Aminomethyl)-4-methylthiazole-5-carboxylate [sic]

N-BOC-Glycine [sic] thioamide (10.0 g, 52.6 mmol) was introduced into methanol (70 ml), and methyl 2-chloroacetoacetate (7.9 g, 52.6 mmol) was added. The mixture was warmed for 2 hours at 60° C. and subsequently stirred for 48 hours at room temperature. The methanol was removed on a rotary evaporator and the residue was extracted by stirring with acetone/diethyl ether. The precipitate which remained was filtered off with suction and the filtrate was concentrated. The solid obtained from the filtrate constituted the product (pure after TLC and HPLC). Yield: 8.7 g (30.4 mmol, 57.8%). ESI-MS: 287 (M+H$^+$).

2-(N-BOC-Aminomethyl)-4-methylthiazole-5-carboxylic [sic] Acid

Methyl 2-(N-BOC-aminomethyl)-4-methylthiazole-5-carboxylate [sic] (2.8 g, 9.74 mmol) was dissolved in 1,4-dioxane (30 ml), and 1N sodium hydroxide solution (19 ml) was added. After the mixture had been stirred for 4 hours at room temperature, the 1,4-dioxane was removed on a rotary evaporator. It was diluted with water and washed with ethyl acetate. The aqueous phase was acidified with 20% strength potassium hydrogen sulfate solution, and the precipitate obtained during this process was filtered off with suction and washed with water. The product thus obtained was dried in a vacuum drying oven at 40° C. Yield: 2.5 g.

d) 2-(N-BOC-Aminomethyl)-4-methylthiazole-5-carboxamide [sic]

2-(N-BOC-Aminomethyl)-4-methylthiazole-5-carboxylic [sic] acid (12.6 g, 46.27 mmol) was dissolved in dichloromethane (460 ml) and dimethylformamide (0.4 ml). After the mixture had cooled to 0° C., a solution of oxalyl chloride (6.46 g, 50.90 mmol) in dichloromethane (40 ml) was added dropwise in the course of 30 minutes. After the mixture had been stirred for 2 hours at 0° C., it was cooled to −20° C., and ammonia was passed in at this temperature until the reaction was complete. The mixture was subsequently warmed to room temperature and washed with water. The precipitate formed during this process was filtered off with suction. The organic phase was washed with 5% strength citric acid solution, dried (MgSO$_4$) and concentrated on a rotary evaporator. The resulting solid was combined with the precipitate which had previously been filtered off and dried at 50° C. in a vacuum drying oven. Yield: 9.8 g (36.12 mmol, 78%).

e) 2-(N-BOC-Aminomethyl)-5-cyano-4-methylthiazole [sic]

2-(N-BOC-Aminomethyl)-4-methylthiazole-5-carboxamide [sic] (11.13 g, 41.02 mmol) was suspended in dichloromethane (75 ml) and cooled to 0° C. At this temperature, ethyldiisopropylamine (17.86 ml, 102.55 mmol) was first added, and then, slowly, a solution of trifluoroacetic anhydride (6.56 ml, 47.17 mmol) in dichloromethane (20 ml). After stirring for 1 hour, the mixture was diluted with dichloromethane and washed with 5% strength citric acid solution. After drying (MgSO$_4$), the solvent was removed on a rotary evaporator and the crude product was purified by flash chromatography.

Yield: 6.5 g (25.66 mmol, 63%).

f) 2(N-BOC-Aminomethyl)-4-methylthiazole-5-thioamide [sic]

2-(N-BOC-Aminomethyl)-5-cyano-4-methylthiazole [sic] (7.5 g, 29.61 mmol) was dissolved in pyridine (30 ml), and triethylamine (27 ml) was added. The solution was saturated with hydrogen sulfide at 0° C. and then left to stand for 48 hours at room temperature. The solvent was subsequently removed on a rotary evaporator, and the residue was taken up in ethyl acetate, washed with 20% strength potassium hydrogen sulfate solution and dried over magnesium sulfate. The solvent was removed on a rotary evaporator, and the crude product was dissolved in dichloromethane and precipitated with petroleum ether. The product which had precipitated was filtered off with suction and dried in a vacuum drying oven [lacuna] 40° C. Yield: 7.1 g (24.7 mmol, 83%).

g) 5-Amidino-2-(N-BOC-aminomethyl)-4-methylthiazole [sic]×HOAc 2-(N-BOC-Aminomethyl)-4-methylthiazole-5-thioamide [sic] (7.1 g, 24.70 mmol) was dissolved in dichloromethane (40 ml), and iodomethane (17.5 g, 123.52 mmol) was added. After the mixture had been stirred for 56 hours at room temperature, the solvent was removed on a rotary evaporator. The residue was dissolved in 10% strength methanolic ammonium acetate solution (29 ml) and stirred at 40° C. until the reaction was complete. The solvent was removed on a rotary evaporator, the residue was extracted by stirring with dichloromethane, and the resulting solid was filtered off with suction and washed with dichloromethane. The residue was dissolved in methanol and converted into the corresponding acetate by means of an acetate-loaded ion exchanger. The solvent was removed on a rotary evaporator and the resulting reddish-brown oil was extracted by stirring with dichloromethane. During this process, the product was obtained as colorless solid which was dried in vacuo at 400C. Yield: 5.3 g (16.04 mmol, 65%).

h) 5-Amidino-2-aminomethyl-4-methylthiazole×2 HCl

5-Amidino-2-(N-BOC-aminomethyl)-4-methylthiazole [sic]×HOAC (1.6 g, 4.84 mmol) was suspended in dichloromethane (20 ml), and 4M hydrochloric acid in 1,4-dioxane (4.84 ml, 19.37 mmol) was added at room temperature and the mixture was stirred for 3 hours at this temperature. The product was filtered off, washed with dichloromethane and dried in vacuo at 40° C.

Yield: 0.73 g (3.00 mmol, 62%).

2-Aminomethyl-5-amidino-4-trifluoromethylthiazole×2 HCl a) Ethyl 2-(N-BOC-Aminomethyl)-4-trifluoromethylthiazole-5-carboxylate [sic]

N-BOC-Glycine [sic] thioamide (5.0 g, 26.28 mmol) was dissolved in acetonitrile (60 ml), and a solution of ethyl 2-chloro-4,4,4-trifluoroacetoacetate (6.38 g, 26.28 mmol) was added dropwise at 5–10° C. Then, the mixture was stirred for a further 30 minutes at 5° C. and for 12 hours at room temperature. The batch was then cooled to 0° C., and triethylamine (12 ml, 86.77 mmol) was added dropwise. After the mixture had been stirred for 20 minutes at 0° C., the yellow suspension had changed into a clear reddish-brown solution. Then, thionyl chloride (2.1 ml, 28.89 mmol) was slowly added dropwise at 0° C. After the mixture had been stirred for 20 minutes at 0° C., it was warmed to room temperature for a further hour. The solvent was removed on a rotary evaporator, and the residue was taken up in water (100 ml) and extracted repeatedly with ethyl acetate. The combined organic phases were dried ($Na_2AO_4$) and concentrated. The crude product was purified by chromatography (silica gel MeOH:DCM=2:98). Yield: 2.2 g (6.4 mmol, 24.5%).

$^1$H NMR (270 MHz, DMSO-$d_6$) δ=1.30 (t, J=6.5 Hz, 3H), 1.45 (s, 9H), 4.35 (q, J=6.5 Hz, 2H), 4.45 (d, J=6.5 Hz, 2H), 7.95 (t, J=6.5 Hz, 1H).

b) 2-(N-BOC-Aminomethyl)-4-tri-fluoromethylthiazole-5-carboxamide [sic]

Ethyl 2-(N-BOC-aminomethyl)-4-trifluoromethylthiazole-5-carboxylate [sic] (15 g, 42.33 mol) was dissolved in methanol. Ammonia was passed into the solution at room temperature until all of the ester had been converted into the carboxamide. The solvent was removed on a rotary evaporator and the crude product was purified by flash chromatography. Yield: 4.6 g (14.14 mmol, 33%).

c) 2-(N-BOC-Aminomethyl)-5-cyano-4-trifluoromethylthiazole [sic]

2-(N-BOC-Aminomethyl)-4-trifluoromethylthiazole-5-carboxamide [sic] (4.6 g, 14.14 mmol) was dissolved in dichloromethane (30 ml) and cooled to −5° C. Ethyldiisopropylamine (4.6 g, 35.35 mmol) and a solution of trifluoroacetic anhydride (3.4 g, 16.26 mmol) in dichloromethane (10 ml) were added at this temperature. Then, the mixture was stirred for a further 2 hours at 0° C. It was washed in succession with saturated sodium hydrogen carbonate solution and 5% strength citric acid solution. After drying (MgSO$_4$), the solvent was removed on a rotary evaporator. The crude product was extracted by stirring with diethyl ether/petroleum ether. The supernatant was separated from the oil and concentrated on a rotary evaporator. Yield: 1.9 g (6.18 mmol, 44%).

d) 2-(N-BOC-Aminomethyl)-4-trifluoromethylthiazole-5-thioamide [sic]

2-(N-BOC-Aminomethyl)-5-cyano-4-trifluoromethylthiazole [sic] (4.6 g, 14.97 mmol) was dissolved in pyridine (20 ml), triethylamine (24 ml) was added, and the solution was saturated with hydrogen sulfide. After two days at room temperature, the solvent was removed on a rotary evaporator. The crude product was taken up in ethyl acetate and washed in succession with 20% strength sodium hydrogen sulfate solution and water. After drying (MgSO$_4$), the solvent was removed on a rotary evaporator. The crude product was purified by flash chromatography. Yield: 2.5 g (7.32 mmol, 49%).

e) 5-Amidino-2-(N-BOC-aminomethyl)-4-trifluoromethylthiazole [sic]

2-(N-BOC-Aminomethyl)-4-trifluoromethylthiazole-5-thioamide [sic] (2.5 g, 7.32 mmol) was dissolved in dichloromethane (10 ml), and iodomethane (10.4 g, 73.24 mmol) was added. Then, the mixture was stirred for 48 hours at room temperature. After the solvent had been removed on a rotary evaporator, the residue was taken up in methanol (5 ml), and 10% strength methanolic ammonium acetate solution (8.5 ml, 10.98 mmol) was added. After the mixture had been stirred for 4 days at room temperature, the solution of the crude product was passed over an acetate-loaded ion exchanger and the solvent was removed on a rotary evaporator. The crude product was purified by flash chromatography. Yield: 0.8 g (2.08 mmol, 28%).

f) 5-Amidino-2-aminomethyl-4-trifluoromethylthiazole×2 HCl

5-Amidino-2-(N-BOC-aminomethyl)-4-trifluoromethylthiazole [sic] (0.8 g, 2.08 mmol) was dissolved in dichloromethane, and a 4M solution of hydrochloric acid in 1,4-dioxane (2.1 ml, 4.2 mmol) was added. After the mixture had been stirred for 1 hour at room temperature, the solvent was removed on a rotary evaporator. The crude product obtained in this way was employed in the following reactions without further purification. Yield: 0.6 g (2.0 mmol, 97%). ESI-MS: 225 (M+H$^+$).

5-Aminomethyl-3-methylthiophene-2-carbonitrile a) 5-Formyl-3-methylthiophene-2-carbonitrile 112 ml (179 mmol) of a 1.6-molar solution of n-butyllithium in n-hexane were added in the course of 20 minutes to a solution of 25.1 ml (179 mmol) of diisopropylamine in 400 ml of tetrahydrofuran cooled to −78° C. The solution was allowed to come to −35° C., then cooled again to −78° C., and a solution of 20.0 g (162 mmol) of 2-cyano-3-methylthiophene in 80 ml of tetrahydrofuran was slowly added dropwise at this temperature. During this process, the color of the solution changed to dark red. Stirring was continued for 45 minutes, 63 ml (811 mmol) of dimethylformamide were slowly added dropwise, and the mixture was stirred for another 30 minutes. For work-up, a solution of 27 g of citric acid in 160 ml of water was added at −70° C. The mixture was concentrated on a rotary evaporator, 540 ml of saturated sodium chloride solution were added, and the batch was extracted three times using in each case 250 ml of diethyl ether. The combined organic extracts were dried over magnesium sulfate. After the desiccant had been filtered off, the solvent was distilled off under a water pump vacuum and the residue was purified by column chromatography (eluant hexane/ethyl acetate 4/1). This gave 23 g (94%) of the title compound. $^1$H NMR (270 MHz, DMSO-$d_6$): δ=2.4 (s, 3H), 8.0 (s, 1H), 9.8 (s, 1H).

b) 5-Hydroxymethyl-3-methylthiophene-2-carbonitrile 5.75 g (152 mmol) of sodium borohydride were added portionwise at room temperature to a solution of 23 g (152 mmol) of 5-formyl-3-methylthiophene-2-carbonitrile in 300 ml of absolute ethanol. The reaction mixture was stirred for 5 minutes, concentrated under a water pump vacuum, taken up in ethyl acetate and extracted with 5% strength citric acid solution and with saturated sodium chloride solution, the organic phase was dried over magnesium sulfate, the desiccant was filtered off, and the solvent was distilled off at room temperature and under a water pump vacuum. This gave 24 g of the title compound as a dark red oil which still contained solvent and which was employed in the following reactions without further purification. $^1$H NMR (270 MHz, DMSO-$d_6$): δ=2.4 (s, 3H), 4.7 (m, 2H), 5.9 (m, 1H), 7.0 (s, 1H).

c) 5-Bromomethyl-3-methylthiophene-2-carbonitrile 44 g (167 mmol) of triphenylphosphine were added to a solution of 24 g (152 mmol) of 5-hydroxymethyl-3-methylthiophene-2-carbonitrile in 180 ml of tetrahydrofuran. Then, a solution of 55 g (167 mmol) of tetrabromomethane in 100 ml of tetrahydrofuran was added. The mixture was stirred for 90 minutes at room temperature. The reaction mixture was concentrated on a rotary evaporator under a water pump vacuum, and the residue was purified by column chromatography (eluant hexane:ethyl acetate 8:2). This gave 34 g of the title compound which still contained a small amount of solvent. $^1$H NMR (270 MHz, DMSO-$d_6$): δ=2.4 (s, 3H), 5.0 (s, 2H), 7.3 (s, 1H).

d) 5-N,N-bis(tert-Butoxycarbonyl)aminomethyl-3-methylthiophene-2-carbonitrile 5.0 g (167 mmol) of sodium hydride (80% suspension in mineral oil) was added portionwise to a solution of 33.8 g (152 mmol) of 5-bromomethyl-3-methylthiophene-2-carbonitrile in 255 ml of tetrahydrofuran, cooled to 0° C. Then, a solution of 36.4 g (167 mmol) of di-tert-butyl iminodicarboxylate in 255 ml of tetrahydrofuran was added dropwise, during this process the temperature did not rise above 5° C. The mixture was allowed to come to room temperature and was stirred overnight. To complete the reaction, the mixture was warmed for a further 3 hours at 35° C. and was then left to cool to room temperature, and 510 ml of a saturated ammonium chloride solution was added slowly. The solvent was distilled off under a water pump vacuum, the residue was extracted repeatedly with ethyl acetate, and the combined organic phases were washed with saturated sodium chloride solution, dried over magnesium sulfate and concentrated on a rotary evaporator. This gave 57.6 g of an oily residue which still contained di-tert-butyl iminodicarboxylate and which was employed in the following reaction as a crude product. $^1$H NMR (270 MHz, DMSO-$d_6$): δ=1.45 (s, 18H), 2.35 (s, 3H), 4.85 (s, 2H), 7.05 (s, 1H).

e) 5-Aminomethyl-3-methylthiophene-2-carbonitrile Hydrochloride 52.6 g of 5-N,N-bis(tert-butoxycarbonyl)aminomethyl-3-methylthiophene-2-carbonitrile (crude product of d), not more than 139 mmol) were dissolved in 950 ml of ethyl acetate and the solution was cooled to 0° C. It was saturated with hydrogen chloride gas, during which process a white precipitate separated out after 10 minutes. The mixture was stirred for two hours at room temperature and for one hour at 30° C., the resulting suspension was subsequently concentrated on a rotary evaporator, the residue was extracted by stirring with diethyl ether, the solvent was filtered off, and the solid residue was dried at room temperature in vacuo. This gave 24.7 g (94%) of the title compound as white powder.

$^1$H NMR (270 MHz, DMSO-$d_6$): δ=2.4 (s, 3H), 4.25 (s, 2H), 7.3 (s, 1H), 8.8–9.0 (bs, 3H). $^{13}$CNMR (DMSO-$d_6$): 15.0 (CH3), 36.4 (CH$_2$), 104.8 (C-2), 113.8 (CN), 131.5 (C-4), 142.8 (C-5), 149.6 (C-3).

5-Aminomethyl-3-chlorothiophene-2-carbonitrile Hydrochloride

This compound was synthesized as described for 5-aminomethyl-3-methylthiophene-2-carbonitrile, the 3-chloro-2-cyanothiophene employed having been prepared by dehydrating 3-chlorothiophene-2-carboxamide with trifluoroacetic anhydride.

5-Aminomethyl-4-methylthiophene-3-thiocarboxamide a) Ethyl 2-Amino-3-cyano-4-methylthiophene-5-carboxylate Ethyl 2-amino-3-cyano-4-methylthiophene-5-carboxylate was synthesized as described in "Organikum" [Organic Chemistry], 19th Edition, Dt. Verlag der Wissenschaften, Leipzig, Heidelberg, Berlin, 1993, Chapter 6, pp.374–375, starting from 130 g (1.0 mol) of ethyl acetoacetate, 66 g (1.0 mol) of malononitrile, 32 g (1.0 mol) of sulfur and 80 g (0.92 mol) of morpholin. $^1$H NMR (270 MHz, DMSO-$d_6$): δ=1.25 (t, 3H), 2.3 (s, 3H), 4.2 (q, 2H), 7.9 (bs, 2H).

b) Ethyl 4-Cyano-3-methylthiophene-2-carboxylate

A solution of 20.5 g (97.5 mmol) of ethyl 2-amino-3-cyano-4-methylthiophene-5-carboxylate in 600 ml of a 1:1 mixture of acetonitrile and dimethylformamide was cooled to 5° C., and 15.7 g (146 mmol) of tert-butyl nitrite were added dropwise, during which process the temperature of the reaction mixture rose and gas was evolved vigorously. The mixture was stirred for seven hours at room temperature and concentrated on a rotary evaporator under a high vacuum, the residue was purified by column chromatography (eluant dichloromethane), and 9.1 g (48%) of the desired compound were obtained as yellow oil. $^1$H NMR (270 MHz, DMSO-$d_6$): δ=1.3 (t, 3H), 2.55 (s, 3H), 4.3 (q, 2H), 8.8 (s, 1H).

c) 5-Hydroxymethyl-4-methylthiophene-3-carbonitrile 2.44 g (64 mmol) of lithium aluminum hydride were added portionwise at 0° C. to a solution of 25.1 g (129 mmol) of ethyl 3-cyano-4-methylthiophene-5-carboxylate in 400 ml of tetrahydrofuran. The mixture was stirred for 5 hours at room temperature, excess reducing agent was destroyed by adding 0.5 N hydrochloric acid, and the reaction mixture was concentrated under a water pump vacuum, diluted with water and extracted three times with ethyl acetate. The combined organic phases were then washed in each case once with 0.5 N hydrochloric acid and saturated sodium chloride solution. The organic phase was dried over magnesium sulfate, the desiccant was filtered off, and the solvent was distilled off under a water pump vacuum at room temperature. The residue was purified by column chromatography (eluant dichloromethane/methanol 95:5), and 16.1 g (83%) of the desired compound were obtained as a slightly yellow oil.

$^1$H NMR (270 MHz, DMSO-$d_6$): δ=2.2 (s, 3H), 4.6 (d, 2H), 5.7 (m, 1H), 8.35 (s, 1H).

d) 5-Bromomethyl-4-methylthiophene-3-carbonitrile 30 g (115 mmol) of triphenylphosphine were added at 5° C. to a solution of 16 g (104 mmol) of 5-hydroxymethyl-4-methylthiophene-3-carbonitrile in 300 ml of tetrahydrofuran. Then, a solution of 38 g (115 mmol) of tetrabromomethane in 100 ml of tetrahydrofuran was added. The mixture was stirred overnight at room temperature. The reaction mixture was concentrated on a rotary evaporator under a water pump vacuum and the residue was purified by column chromatography (eluant petroleum ether:dichloromethane 1:1). This gave 17 g (76%) of the title compound as yellow oil. $^1$H NMR (270 MHz, DMSO-$d_6$): δ=2.25 (s, 3H), 5.0 (s, 2H), 8.5 (s, 1H).

e) 5-N,N-bis(tert-Butoxycarbonyl)aminomethyl-4-methylthiophene-3-carbonitrile 3.5 g (103 mmol) of sodium hydride (oil-free) was added portionwise to a solution of 17.2 g (79.5 mmol) of 5-bromomethyl-4-methylthiophene-3-carbonitrile in 250 ml of tetrahydrofuran, cooled to 0° C. Then, a solution of 22.5 g (103 mmol) of di-tert-butyl iminodicarboxylate in 100 ml of tetrahydrofuran was added dropwise, during which process the temperature did not rise above 5° C. The mixture was allowed to warm to room temperature and was stirred for 2 hours. 400 ml of a saturated ammonium chloride solution was added slowly. The solvent was distilled off under a water pump vacuum, and the residue was diluted with a little water and extracted three times with ethyl acetate. The combined organic phases were washed with saturated ammonium chloride solution and with saturated sodium chloride solution, dried over magnesium sulfate and concentrated on a rotary evaporator. This gave 28 g of an oil which still contained di-tert-butyl iminodicarboxylate and was employed in the following reaction as crude product. $^1$H NMR (270 MHz, DMSO-$d_6$): δ=1.4 (s, 9H), 1.45 (s, 9H), 2.3 (s, 3H), 4.8 (s, 2H), 8.4 (s, 1H).

f) 5-N,N-bis(tert-Butoxycarbonyl)aminomethyl-4-methylthiophene-3-thiocarboxamide The crude product obtained in e) (not more than 79 mmol) was dissolved in 280 ml of pyridine and 140 ml of triethylamine and the solution was saturated with hydrogen sulfide at room temperature. The color of the solution, which was yellow at the beginning, changed to green. The mixture was stirred overnight at room temperature. To complete the reaction, hydrogen sulfide was passed in for a further 15 minutes and stirring was continued for two hours at room temperature. Excess hydrogen sulfide was expelled with the aid of a nitrogen stream using a washing tower. Then, the reaction mixture was concentrated on a rotary evaporator, and the concentrate was taken up in ethyl acetate, washed repeatedly with 20% strength sodium hydrogen sulfate solution, dried over magnesium sulfate and concentrated on a rotary evaporator. This gave 27 g of a pale yellow solid foam which was employed in the following reaction without further purification. $^1$H NMR (270 MHz, DMSO-$d_6$): δ=1.4 (s, 18H), 2.15 (s, 3H), 4.8 (s, 2H), 7.5 (s, 1H), 9.3 (bs, 1H), 9.75 (bs, 1H).

g) 5-Aminomethyl-4-methylthiophene-3-thiocarboxamide Hydrochloride 27 g of 5-N,N-bis(tert-butoxycarbonyl)-aminomethyl-4-methylthiophene-3-thiocarboxamide (crude product of f), not more than 70 mmol) were dissolved in 400 ml of ethyl acetate and the solution was cooled to 0° C. It was saturated with is hydrogen chloride gas, during which process a white precipitate separated out after 10 minutes. The mixture was stirred for two hours at room temperature, the precipitate was filtered off and washed with ethyl acetate, and the solid residue was dried in vacuo at room temperature. This gave 13.6 g (87%) of the title compound as white powder. EI-MS: $M^+$=186.

5-Aminomethyl-4-chlorothiophene-3-thiocarboxamide a) 5-Formyl-4-chlorothiophene-3-carbonitrile 35 g (325 mmol) of tert-butyl nitrite were added dropwise at room temperature to a solution of 53.0 g (250 mmol) of 2-amino-4-chloro-5-formylthiophene-3-carbonitrile (the synthesis of this compound is described in Patent DB 3738910) in 600 ml of a 1:1 mixture of acetonitrile and dimethylformamide, during which process the temperature of the reaction mixture rose from 20° C. to 37° C. and vigorous evolution of gas began. The mixture was cooled to 25° C. and stirred for 7 hours at room temperature, the black solution was concentrated on a rotary evaporator under a high vacuum, the residue was purified by column chromatography (eluant dichloromethane), and 29 g (68%) of the desired compound were obtained as yellow oil. $^1$H NMR (270 MHz, DMSO-$d_6$): δ=9.1 (s, 1H), 10.0 (s, 1H).

b) 5-Hydroxymethyl-4-chlorothiophene-3-carbonitrile 6.3 g (166 mmol) of sodium borohydride were added portionwise at 5° C. to a solution of 28.5 g (166 mmol) of 5-formyl-4-chlorothiophene-3-carbonitrile in 400 ml of rose slightly and the color changed to dark red. A vigorous evolution of gas was observed. After 10 minutes, the reaction mixture was concentrated under a water pump vacuum, taken up in 200 ml of ethyl acetate, extracted with 200 ml of 1 M hydrochloric acid and washed twice with in each case 250 ml of water and with saturated sodium chloride solution, the organic phase was dried over magnesium sulfate, the desiccant was filtered off, and the solvent was distilled off under a water pump vacuum at room temperature. This gave 22 g (76%) of the title compound as dark red oil which was employed in the following reactions without further purification. $^1$H NMR (270 MHz, DMSO-$d_6$): δ=4.65 (bs, 1H), 5.95 (t, 2H), 8.6 (s, 1H).

c) 5-Bromomethyl-4-chlorothiophene-3-carbonitrile 36.1 g (137 mmol) of triphenylphosphine were added at 5° C. to a solution of 21.7 g (125 mmol) of 5-hydroxymethyl-4-chlorothiophene-3-carbonitrile in 250 ml of tetrahydrofuran. Then, a solution of 45.6 g (137 mmol) of tetrabromomethane in 100 ml of tetrahydrofuran was added. The mixture was stirred overnight at room temperature. The precipitate was filtered off, the filtrate was concentrated on a rotary evaporator under a water pump vacuum, and the residue was purified by column chromatography (eluant petroleum ether:dichloromethane 1:1). This gave 26.0 g (88%) of the title compound as an oil.

$^1$H NMR (270 MHz, DMSO-d$_6$): δ=4.95 (s, 2H), 8.8 (s, 1H).

d) 5-N,N-bis(tert-Butoxycarbonyl)aminomethyl-4-chlorothiophene-3-carbonitrile 6.9 g (159 mmol) of sodium hydride (oil-free) was added portionwise to a solution of 25.0 g (106 mmol) of 5-bromomethyl-4-chlorothiophene-3-carbonitrile in 300 ml of tetrahydrofuran, cooled to 0° C. Then, a solution of 34.4 g (159 mmol) of di-tert-butyl-iminodicarboxylate in 100 ml of tetrahydrofuran was added dropwise, during which process the temperature did not rise above 5° C. The mixture was allowed to warm to room temperature and was stirred for two hours. 300 ml of a saturated ammonium chloride solution were added slowly. The solvent was distilled off under a water pump vacuum, and the residue was diluted with a little water and extracted three times with ethyl acetate. The combined organic phases were washed with saturated ammonium chloride solution and with saturated sodium chloride solution, dried over magnesium sulfate and concentrated on a rotary evaporator. This gave 51.3 g of an oil which still contained di-tert-butyl iminodicarboxylate and solvent residues and which was employed in the following reaction as crude product. $^1$H NMR (270 MHz, DMSO-d$_6$): δ=1.4 (s, 9H), 1.45 (s, 9H), 4.8 (s, 2H), 8.65 (s, 1H).

e) 5-N,N-bis(tert-Butoxycarbonyl)aminomethyl-4-methylthiophene-3-thiocarboxamide Some of the crude product obtained in d) (39.4 g, not more than 106 mmol) was dissolved in 400 ml of pyridine and 40 ml of triethylamine and the solution was saturated with hydrogen sulfide at room temperature. The color of the solution, which was yellow at the beginning, changed to green. The mixture was stirred overnight at room temperature. Excess hydrogen sulfide was expelled with the aid of a stream of nitrogen using a washing tower. The reaction mixture was then poured into ice-cooled 20% strength sodium hydrogen sulfate solution and extracted three times with ethyl acetate. The organic phase was then washed repeatedly with 20% strength sodium hydrogen sulfate solution, dried over magnesium sulfate and concentrated on a rotary evaporator. This gave 49.0 g of a solvent-containing residue which was employed in the following reaction without further purification. $^1$H NMR (270 MHz, DMSO-d$_6$): δ=1.4, 1.45 (s, 18H), 4.8 (s, 2H), 7.75 (s, 1H), 9.4 (bs, 1H), 10.0 (bs, 1H).

f) 5-Aminomethyl-4-chlorothiophene-3-thiocarboxamide Hydrochloride 38.0 g of the crude product of e), not more than 93 mmol, were dissolved in 400 ml of ethyl acetate and cooled to 0° C. The solution was saturated with hydrogen chloride gas, during which process a white precipitate separated out after 10 minutes. Since the reaction was still incomplete, 200 ml of ethyl acetate were added, and the mixture was saturated again with hydrogen chloride gas and stirred overnight at room temperature. The precipitate was filtered off, washed with petroleum ether and dried in vacuo at room temperature. This gave 21.1 g of the title compound as white powder which contained ammonium chloride as contamination. EI-MS: M$^+$=206.

5-Aminomethyl-1-methyl-1H-[1,2,4]-triazole-3-carboxamide a) Ethyl Aminothiooxoacetate Hydrogen sulfide was passed to saturation at 0° C. in a solution of 29.1 g (294 mmol) of ethyl cyanoformate and 0.4 g (0.57 ml, 5.1 mmol) of diethylamine in 20 ml of benzene, during which process the solution turned orange. The mixture was stirred over the weekend at room temperature, the reaction mixture was cooled to 0° C., and the precipitate formed (29.1 g) was filtered off and washed with cold benzene. The mother liquor was concentrated and again cooled to 0° C. The mixture was filtered off, the residue was washed with petroleum ether, and a further 5.7 g of the title compound were obtained as pale yellowish solid (Rf=0.7, dichloromethane/methanol 9:1). Overall yield: 89%. $^1$H NMR (270 MHz, DMSO-d6): δ=1.25 (t, J=7 Hz, 3H), 4.2 (q, J=7 Hz, 2H) 9.9 (bs, 1H, NH), 10.4 (bs, 1H, NH).

b) Ethyl Methyloxamidrazonecarboxylate

A solution of 11.93 g (13.6 ml, 259 mmol) of methylhydrazine in 100 ml of ethanol was added at room temperature dropwise to a solution of 34.5 g (259 mmol) of ethyl aminothiooxoacetate in 400 ml of ethanol, during which process the temperature of the reaction mixture rose slightly. The mixture was stirred for three hours at room temperature and concentrated, and the residue was employed in reaction c) without further purification.

c) Ethyl Amino[(2-tert-butoxycarbonylaminoacetyl)methyl]-hydrazonoacetate

Activation of Boc-Gly-OH and reaction with b):

37.7 g (51.7 ml, 373 mmol) of triethylamine were added at room temperature to a solution of 54.46 g (311 mmol) of Boc-glycine in 400 ml of tetrahydrofuran. The mixture was cooled to −5° C., and a solution of 40.47 g (35.5 ml, 311 mmol) of ethyl chloroformate in 100 ml of tetrahydrofuran was slowly added dropwise in the course of 40 minutes. The mixture was stirred for 30 minutes at −5° C., the resulting precipitate was filtered off and washed with a small amount of tetrahydrofuran, and the filtrate was directly reacted further by slowly adding dropwise at room temperature a solution of the residue from b) (259 mmol) in 300 ml of tetrahydrofuran. The mixture was stirred overnight and concentrated to dryness on a rotary evaporator under reduced pressure, and the residue was purified by column chromatography (silica gel, dichloromethane/methanol 95:5, Rf=0.26). This gave 15.7 g of an oil, which was taken up in diethyl ether, and the precipitate was filtered off (8.5 g, 11%). $^1$H NMR (270 MHz, DMSO-d6): δ=1.25 (t, J=7 Hz, 3H), 1.35 (s, 9H), 2.9 (s, 3H), 3.6 (d, J=5 Hz, 2H), 4.3 (q, J=7 Hz, 2H) 6.6 (t, J=5 Hz 1H), 7.3 (bs, 2H).

d) Ethyl 5-Aminomethyl-1-methyl-1H-[1,2,4]-triazole-3-carboxylate 7.0 g (23.2 mmol) of ethyl amino[(2-tert-butoxycarbonylaminoacetyl)methyl]hydrazonoacetate were suspended in 30 ml of xylene and the suspension was immersed for 10 minutes in a silicone oil bath which had been preheated to 180° C. Then, the solvent was distilled off directly from the reaction mixture and the residue was stirred for a further 10 minutes at 180° C. Solvent residues were removed at 50° C. under a high vacuum, and 6.8 g (>95%) of a dark oil were obtained which oil was employed in the following reaction without further purification. A sample was filtered through silica gel and examined by NMR spectroscopy. $^1$H NMR (270 MHz, DMSO-d6): δ=1.25 (t, J=7 Hz, 3H), 1.35 (s, 9H), 3.9 (s, 3H), 4.2–4.4 (m, 4H), 7.5 (t, J=5 Hz, 1H).

e) 5-Aminomethyl-1-methyl-1H-[1,2,4]-triazole-3-carboxamide

Ammonia gas was passed for 20 minutes at −10° C. into a solution of 6.8 g (not more than 23.2 mmol) of ethyl 5-aminomethyl-1-methyl-1H-[1,2,4]-triazole-3-carboxylate in 200 ml of ethanol. Stirring was continued for one hour at 0° C. and overnight at room temperature. Since the reaction was incomplete, the procedure of passing in gas was repeated twice more (as described above) and the mixture was stirred overnight at 0° C. The mixture was concentrated on a rotary evaporator and the residue was purified by column chromatography (dichloromethane +5–10% methanol, Rf=0.3 in dichloromethane/methanol 9:1). This gave 4.71 g as colorless oil. $^1$H NMR (270 MHz, DMSO-d6): δ=1.4 (s, 9H), 3.85 (s, 3H), 4.3 (d, J=5 Hz, 3H), 7.4 (bs, 1H), 7.6 (bs, 1H), 7.65 (bs, J=5 Hz, 1H).

f) 5-Aminomethyl-1-methyl-1H-[1,2,4]-triazole-3-carboxamide Hydrochloride

Hydrogen chloride was passed to saturation at 5° C. to a solution of 4.7 g (not more than 18.4 mmol) of 5-aminomethyl-1-methyl-1H-[1,2,4]-triazole-3-carboxamide in 600 ml of ethyl acetate, during which process a white precipitate formed. The mixture was stirred overnight at room temperature and concentrated on a rotary evaporator, diethyl ether was added, the mixture was concentrated and again taken up in diethyl ether, and the precipitate was filtered off and dried. This gave 3.7 g of a white solid which still contained ammonium chloride. $^1$H NMR (270 MHz, DMSO-d6): δ=3.95 (s, 3H), 4.3 (bs, 2H), 7.6 (bs, 1H), 7.75 (bs, 1H), 8.7–8.9 (m, 2H).

5-Aminomethyl-3-cyanofuran Hydrochloride a) 5-N,N-bis(tert-Butoxycarbonyl)aminomethyl-3-cyanofuran A solution, cooled to 0° C., of 20.5 g (0.11 mol) of 5-bromomethyl-3-cyanofuran (L. M. Pevzner, V. M. Ignat'ev, B. I. Ionin, Russ. J. of Gen. Chem. 1994, 64, 2, 125–128) in 50 ml of tetrahydrofuran was added with stirring in the course of 30 minutes at 0° C. to a suspension of 4.8 g (0.12 mol) of sodium hydride (60% dispersion in mineral oil) in 30 ml of tetrahydrofuran. A solution of 26.2 g (121 mmol) of di-tert-butyl iminodicarboxylate in 50 ml of tetrahydrofuran was subsequently added dropwise, during which process the temperature did not climb above 5° C. The mixture was stirred for three hours at 5–10° C., allowed to warm to room temperature and stirred overnight. 150 ml of a saturated ammonium chloride solution were slowly added. The solvent was distilled out under a water pump vacuum, the residue was extracted four times using in each case 60 ml of ethyl acetate, and the combined organic phases were washed twice using saturated sodium chloride solution, dried over magnesium sulfate and concentrated in a rotary evaporator. After drying for three hours at room temperature in vacuo (1 mm Hg), 33.2 g of a dark syrup which still contained di-tert-butyliminodicarboxylate resulted, and this was employed as crude product in the reaction below. $^1$H NMR (250 MHz, d$_6$-DMSO): δ=1.40, 1.45 (s, 18H), 4.70 (s, 2H), 6.70 (s, 1H), 8.6 (s, 1H).

b) 5-Aminomethyl-3-cyanofuran Hydrochloride 12.89 g of 5-N,N-bis(tert-butoxycarbonyl)aminomethyl-3-cyanofuran (crude product from a) were dissolved in 80 ml of ethyl acetate and cooled to −10° C. The mixture was saturated with hydrogen chloride gas, a white precipitate separating out after 15 minutes. The mixture was allowed to come to room temperature and was stirred for two hours, the resulting suspension was subsequently concentrated in a rotary evaporator, the residue (7 g) was extracted by stirring with diethyl ether, solvent was removed by filtration, and the solid residue was dried in vacuo at room temperature. 5 g (79%) of the title compound resulted as a pale ochre powder. $^1$H NMR (250 MHz, d$_6$-DMSO): δ=4.15 (bs, 2H), 7.0 (s, 1H), 8.6–8.9 (m, 4H).

5-Aminomethyl-1-methylpyrrole-2-carbonitrile a) 5-Cyano-1-methylpyrrole-2-carbaldehyde 1-Methylpyrrole was converted into 2-cyano-1-methylpyrrole by reaction with chlorosulfonyl isocyanate and dimethylformamide in acetonitrile (see, for example, C. E. Loader et al. Can. J. Chem. (1981), 59, 2673–6).

Diisopropylamine (17.5 ml, 124.38 mmol) was introduced into THF (100 ml) under nitrogen. N-Butyllithium solution in hexane (15% strength, 75.9 ml, 124.38 mmol) was added dropwise at −78° C. The mixture was subsequently stirred for 45 minutes at −20° C. and then cooled again to −78° C. At this temperature, a solution of 1-methylpyrrole-2-carbonitrile (12 g, 113.07 mmol) in THF (50 ml) was added dropwise. After stirring for 45 minutes at −78° C., DMF (43.9 ml, 546.46 mmol) was added dropwise, and the mixture was stirred at this temperature for a further 2 hours. After addition of citric acid monohydrate (20.56 g), the mixture was warmed to room temperature, and water (112 ml) was added. The THF was removed in a rotary evaporator, and the aqueous phase was saturated with sodium chloride and extracted with diethyl ether (3×200 ml). The combined organic phases were washed with saturated sodium chloride solution and dried over sodium sulfate. The solvent was removed in a rotary evaporator and the crude product was purified by means of flash chromatography (silica gel, dichloromethane). Yield: 8.25 g (54%).

1H [sic] NMR (CDCl$_3$) δ=4.1 (s, 3H), 6.8 (d, 1H), 6.9 (d, 1H), 9.7 (s, 1H).

b) 5-Hydroxymethyl-1-methylpyrrole-2-carbonitrile

The product obtained in accordance with a) (8.2 g, 61.1 mmol) was dissolved in ethanol (200 ml), and sodium borohydride (2.31 g, 61.13 mmol) was added at −10° C. After stirring for 1.5 hours at 0–5° C., the solvent was removed in a rotary evaporator, and ice-water and 20% strength sodium hydrogen sulfate solution were added to the residue. The aqueous phase was extracted with ethyl acetate. The combined organic phases were washed to neutrality with saturated sodium hydrogen carbonate solution and water and dried over sodium sulfate. The solvent was removed in a rotary evaporator and the crude product was purified by means of flash chromatography (silica gel, dichloromethane/methanol=97.5/2.5). Yield: 7.6 g (91%). 1H [sic] NMR (CDCl$_3$) δ=1.9 (t, 1H), 3.75 (s, 3H), 4.6 (d, 2H), 6.1 (d, 1H), 6.7 (d, 1H).

c) 5-Azidomethyl-1-methylpyrrole-2-carbonitrile

The product obtained in accordance with b) (7.5 g, 55.08 mmol) was dissolved in DMF (220 ml), and triphenylphosphine (43.34 g, 165.25 mmol) was added at 0° C. After stirring for 5 minutes at this temperature, tetrabromomethane (54.8 g, 165.25 mmol) was added. The mixture was subsequently stirred for 30 minutes at 0° C. and for 1.5 hours at room temperature. After cooling to 0° C., sodium azide (4.37 g, 67.21 mmol) was added. The mixture was subsequently stirred for 4.5 hours at room temperature. Saturated sodium chloride solution was added dropwise at 0° C., and the batch was diluted with ethyl acetate. The organic phase was separated off, and the aqueous phase was extracted with diethyl ether. The combined organic phases were washed with water and dried over sodium sulfate. The solvent was removed in a rotary evaporator and the crude product was purified by means of flash chromatography (silica gel, ethyl acetate/hexane=1/20).

Yield: 5.6 g (63%). 1H [sic] NMR (CDCl$_3$) δ=3.75 (s, 3H), 4.35 (s, 2H), 6.2 (d, 1H), 6.7 (d, 1H).

d) 5-Aminomethyl-1-methylpyrrole-2-carbonitrile

The product obtained in accordance with c) (4.71 g, 29.25 mmol) was dissolved in methanol (100 ml), and palladium on charcoal (10%, 1 g) was added. The mixture was subsequently hydrogenated with hydrogen under 1 atmosphere for 4 hours. The catalyst was removed by filtration through Celitee and the filtrate was evaporated in a rotary evaporator. The residue was extracted by stirring with dichloromethane/diethyl ether=1/1. The product was filtered off with suction and dried at 35° C. in a vacuum drying oven.

Yield: 2.7 g (68%). 1H [sic] NMR (CDCl$_3$) δ=3.75 (s, 3H), 3.85 (s, 2H), 6.05 (d, 1H), 6.7 (d, 1H).

Aminomethyl-1-methylpyrrole-2-carbonitrile
a) 5-Cyano-1-methylpyrrole-3-carbaldehyde Aluminum trichloride (24.24 g, 180.86 mmol) was dissolved in nitromethane/dichloromethane (1/1, 320 ml), the solution was cooled to −20° C., and 1-methylpyrrole-2-carbonitrile (8 g, 75.36 mmol) was added. α,α-Dichlorodimethyl ether (10.4 g, 90.43 mmol), dissolved in dichloromethane (42 ml), was subsequently added dropwise. After stirring for 4 h at 0° C., the batch was poured onto ice (200 g). The aqueous phase was extracted with diethyl ether. The combined organic phases were washed until neutral with saturated sodium hydrogen carbonate solution, water and saturated sodium chloride solution. After drying over sodium sulfate, the solvent was removed in a rotary evaporator. The crude product was employed in the reactions below without further purification.

Yield: 9.2 g (91%). 1H [sic] NMR (CDCl$_3$) δ=3.8 (s, 3H); 7.2 (s, 1H); 7.4 (s, 1H); 9.85 (s, 1H).

b) Starting from 5-Cyano-1-methylpyrrole-3-carbaldehyde; 4-aminomethyl-1-methylpyrrole-2-carbonitrile was synthesized analogously to the synthesis of 5-aminomethyl-1-methylpyrrole-2-carbonitrile. However, the 4-azidomethyl-1-methylpyrrole-2-carbonitrile was advantageously reduced in a Staudinger reaction (see S. Nagarajan et al. J. Org. Chem. 1987, 52, 5044–6).

1H [sic] NMR (DMSO-d$_6$) δ=3.77 (s, 3H), 3.84 (sbr, 2H), 7.00 (sbr, 1H), 7.26 (s, 1H), 8.05 (sbr, 2H).

5-Aminomethyl-1-methylpyrrole-3-carbonitrile
a) 4-Cyano-1-methylpyrrole-2-carbaldehyde 1-Methylpyrrole-2-carbaldehyde (10 g, 91.6 mmol) was dissolved in acetonitrile (100 ml) and cooled to −45° C. Chlorosulfonyl isocyanate (38.9 g, 274.9 mmol) in acetonitrile (40 ml) was added dropwise in the course of 40 minutes. The mixture was subsequently stirred for 12 hours at room temperature. After dropwise addition of dimethylformamide (35 ml), the mixture was warmed to 50° C. for 1 hour. After cooling to room temperature, the reaction mixture was poured onto ice (200 ml) and 2N sodium hydroxide solution (286 ml). The precipitate formed was filtered off with suction. The filtrate was extracted with diethyl ether. The combined ether phases were washed until neutral with dilute sodium hydrogen carbonate solution and water and dried over sodium sulfate. The solvent was distilled out in a water pump vacuum and the residue was combined with the precipitate previously obtained. Recrystallization from petroleum ether gave 4-cyano-1-methylpyrrole-2-carbaldehyde (4.3 g) (see, for example, C. E. Loader et al. Can. J. Chem. (1981), 59, 2673–6) 1-H [sic] NMR (CDCl$_3$) δ=4.0 (s, 3H); 7.2 (s, 1H); 7.3 (s, 1H); 9.6 (s, 1H).

13-C [sic] NMR (CDCl$_3$) δ=37.4; 94.1; 114.7; 125.8; 132.2; 135.8; 179.7.

b) Starting From 4-Cyano-1-methylpyrrole-2-carbaldehyde, 5-Aminomethyl-1-methylpyrrole-3-carbonitrile was Prepared Analogously to the Synthesis of 5-Aminomethyl-1-methylpyrrole-2-carbonitrile.

1H [sic] NMR (DMSO-d$_6$) δ=3.6 (s, 3H), 3.8. (s, 2H), 4.2 (sbr, 2H), 6.4 (s, 1H), 7.6 (s, 1H).

5-Aminomethyl-3-cyano-1,2,4-oxadiazole hydrochloride
a) N-Boc-5-Aminomethyl-3-cyano-1,2,4-oxadiazole Ethyl N-Boc-5-aminomethyl-1,2,4-oxadiazole-2-carboxylate (S. Borg et al. J. Org. Chem. 1995, 60, 3112–20) was dissolved in methanol (50 ml). Ammonia was passed into this solution at −10° C. to RT until the reaction was complete. The solvent was removed in a rotary evaporator. The resulting crude product was dissolved in dichloromethane (70 ml), and diisopropylethylamine (2.9 ml, 16.55 mmol) was added at −5° C. Trifluoroacetic anhydride (1.06 ml, 7.61 mmol), dissolved in dichloromethane (10 ml), was subsequently added dropwise. After stirring for 1.5 hours at 0° C., the batch was diluted with dichloromethane, washed 2× with saturated sodium hydrogen carbonate solution, 2× with 5% strength citric acid solution and 1× with saturated sodium chloride solution and then dried over sodium sulfate. The solvent was removed in a rotary evaporator and the crude product was purified by chromatography (silica gel, dichloromethane:methanol=97.5:2.5). Yield: 1.2 g (80%).

b) 5-Aminomethyl-3-cyano-1,2,4-oxadiazole Hydrochloride

The product obtained in accordance with a) (0.9 g, 4.0 mmol) was dissolved in dichloromethane (45 ml), and 4M hydrochloric acid in dioxane (3.9 ml, 15.61 mmol) was added at RT. After stirring for 16 hours at RT, the solvent was removed in a rotary evaporator. Yield: 645 mg (100%).

1-H [sic] NMR (DMSO-d$_6$) δ=4.6 (s, 2H), 9.2 (s, 3H).

1-Methyl-5-aminomethylpyrazole-3-carboxamide
a) Methyl 1-Methyl-5-amidopyrazole-3-carboxylate 1-Methyl-3-methoxycarbonylpyrazole-5-carboxylic acid chloride (prepared from 3.7 g, 20.09 mmol, of 1-methyl-3-methoxycarbonyl-3-carboxylic acid, J. Org. Chem. 1989, 54, 428) was dissolved in toluene and the solution was cooled to −10° C. Ammonia was subsequently passed in at −10° C. to 0° C. until the reaction was complete. The solvent was removed in a rotary evaporator. The residue was taken up in ethanol. After stirring for 15 minutes, the ethanol was removed in a rotary evaporator, and the residue was dissolved in warm water and precipitated by cooling the solution to 0° C. The precipitate was filtered off with suction, washed with acetone and dried in vacuo at 45° C. Yield: 1.5 g (41%).

b) Methyl 1-Methyl-5-cyanopyrazole-3-carboxylate

The product obtained in accordance with a) (1.5 g, 8.19 mmol) were [sic] taken up in dichloromethane (20 ml). Diisopropylethyl- amine (3.85 ml, 22.11 mmol) was added at −10° C., and a solution of trifluoroacetic anhydride (1.3 ml, 9.44 mmol) in dichloromethane (5 ml) was added dropwise at this temperature in the course of 45 minutes. Stirring was subsequently continued for 1 hour at 0° C. The batch was diluted with dichloromethane and washed 2× with saturated sodium hydrogen carbonate solution, 2× with 5% strength citric acid solution and 1× with saturated sodium chloride solution. After drying over sodium sulfate, the solvent was removed in a rotary evaporator. Yield: 1.35 g (100%).

c) 1-Methyl-5-cyanopyrazole-3-carboxamide

The product obtained in accordance with b) (1.35 g, 8.19 mmol) was introduced into methanol (50 ml) and cooled to −10° C. Ammonia was subsequently passed in in the course of 8 hours. After stirring for 12 hours at room temperature, reaction of the precursor had ended. The product which had precipitated was filtered off with suction, washed with cold methanol and dried in vacuo. Yield: 1.22 g (100%).

1-H [sic] NMR (DMSO-d$_6$) δ=4.0 (s, 3H), 7.4 (s, 1H), 7.5 (s, 1H), 7.8 (s, 1H).

d) 1-Methyl-5-aminomethylpyrazole-3-carboxamide

The product obtained in accordance with c) (0.4 g, 2.66 mmol) was dissolved in acetic acid (30 ml) and 10% palladium on charcoal (78 mg) was added. The mixture was subsequently hydrogenated at room temperature under atmospheric pressure until the reaction was complete. The catalyst was removed by filtration through Celite® and the solvent was removed in a rotary evaporator. Yield: 0.4 g (100%), FAB-MS (M+H$^+$): 155.

1-Methyl-3-aminomethyl-pyrazole-5-carboxamide
a) Methyl 1-Methyl-3-amidopyrazole-5-carboxylate 1-Methyl-5-methoxycarbonylpyrazole-3-carbonyl chloride (synthesized from 4.17 g, 22.6 mmol, of 1-methyl-5-methoxycarbonyl-3-carboxylic acid, J. Org. Chem. 1989, 54, 428) was dissolved in toluene and the solution was cooled to −10° C. Then, ammonia was passed in at −10° C. to 0° C. until the reaction was complete. The solvent was removed in a rotary evaporator. The residue was taken up in ethanol. After the mixture had been stirred for 15 minutes, the ethanol was removed in a rotary evaporator, and the residue was dissolved in warm water and precipitated by cooling to 0° C. The precipitate was filtered off with suction, washed with acetone and dried in vacuo at 45° C. Yield: 3.36 g (18.4 mmol, 81%).

$^1$H NMR (270 MHz, DMSO-d$_6$) δ=3.85 (s, 3H), 4.15 (s, 3H), 7.20 (s, 1H), 7.4 (sbr, 1H), 7.7 (sbr, 1H).

b) Methyl 1-Methyl-3-cyanopyrazole-5-carboxylate

The product obtained in a) (3.36 g, 18.4 mmol) was reacted similarly to the method described above for the synthesis of methyl 1-methyl-cyanopyrazole-3-carboxylate. Yield: 2.59 g (15.7 mmol, 85%).

$^1$H NMR (250 MHz, DMSO-d$_6$) δ=3.90 (s, 3H), 4.15 (s, 3H), 7.60 (s, 1H).

c) 1-Methyl-3-cyanopyrazole-5-carboxamide

The product obtained in b) (2.56 g, 15.5 mmol) was reacted similarly to the method described above for the synthesis of 1-methyl-5-cyanopyrazole-3-carboxamide. Yield: 2.3 g (15.3 mmol, 99%).

$^1$H NMR (250 MHz, DMSO-d$_6$) δ=4.15 (s, 3H), 7.45 (s, 1H), 7.70 (sbr, 1H), 8.15 (sbr, 1H).

d) 1-Methyl-3-aminomethylpyrazole-5-carboxamide×HCl

The product obtained in c) (1.0 g, 6.7 mmol) was reacted similarly to the method described above for the synthesis of 1-methyl-5-aminomethylpyrazole-3-carboxamide. Yield: 1.5 g (5.6 mmol, 83%).

$^1$H NMR (270 MHz, DMSO-d$_6$) δ=4.00 (q, J=6.5 Hz, 2H), 4.10 (s, 3H), 6.90 (s, 1H), 7.60 (sbr, 1H), 8.05 (sbr, 1H), 8.25 (sbr, 3H).

The product can be converted into the corresponding hydrochloride by repeatedly treating it with HCl in 1,4-dioxane and subsequently concentrating the mixture.

EXAMPLE 1

N-(Hydroxycarbonylmethylene)-(D)-cyclohexylalanylprolyl-[2-(4-amidino)thiazolylmethyl]amide Hydrochloride a) N-(t-BuO$_2$C—CH$_2$)-N-Boc-(D)-Cha-Pro-NH—CH$_2$-2-(4-CSNH$_2$)-thiaz N-(t-BuO$_2$C—CH$_2$)-N-Boc-(D)-Cha-Pro-OH (2.0 g, 4.14 mmol), 2-H$_2$N—CH$_2$-thiaz-4-CSNH$_2$ (1.0 g, 4.56 mmol) and diisopropylethylamine (5.5 ml, 32.53 mmol) were dissolved in 25 ml of methylene chloride, the solution was cooled to 0° C., and 4.8 ml (6.21 mmol) of a 50% strength solution of propanephosphonic anhydride in ethyl acetate was added dropwise. The reaction mixture was stirred for 1 hour at 0° C. and for 1 hour at room temperature and subsequently concentrated in vacuo, the residue was taken up in water, the mixture was extracted repeatedly with ether, and the organic phase was dried over magnesium sulfate and concentrated in vacuo. Because of slight impurities, the product was purified by chromatography over silica gel. The pure fractions were crystallized from ether. This resulted in a total of 1.9 g of the required product.

b) N-(t-BuO$_2$C—CH$_2$)-N-Boc-(D)-Cha-Pro-NH—CH$_2$-2-(4-C(SCH$_3$)NH)-Thiaz Hydroiodide N-(t-BuO$_2$C—CH$_2$)-N-Boc-(D)-Cha-Pro-NH—CH$_2$-2-(4-CSNH$_2$)-thiaz (1.7 g, 2.67 mmol) together with 3.7 ml of methyl iodide in 30 ml of methylene chloride were [sic] stirred overnight at room temperature, subsequently concentrated in vacuo under mild conditions and employed in the subsequent reaction in the form of the crude product (2.08 g, max 2.67 mmmol [sic]).

c) N-(t-BuO$_2$C—H$_2$)-N-Boc-(D)-Cha-Pro-NH—CH$_2$-2-(4-C(NH$_2$)NH)-Thiaz Hydroacetate N-(t-BuO$_2$C—CH$_2$)-N-Boc-(D)-Cha-Pro-NH-H$_2$-2-(4-C(SCH$_3$)NH)-thiaz hydroiodide (2.08 g, max 2.67 mmol) were [sic] dissolved in 20 ml of acetonitrile, 0.6 g (8.01 mmol) of ammonium acetate was added, and the mixture was stirred for 1.5 hours at 40–50° C. After the solvent had been evaporated in vacuo in a rotary evaporator, the residue was taken up in methylene chloride, insoluble excess ammonium acetate was removed by filtration, the methylene chloride solution was concentrated, the residue was taken up in ether, and the required product was precipitated with n-hexane as an amorphous solid substance. The crude product (2.1 g) was dissolved in 20 ml of methanol and converted into the corresponding acetate by means of acetate ion exchanger (3.7 g, Fluka, Product No. 00402).

d) HOOC—CH$_2$-(D)-Cha-Pro-NH—CH$_2$-2-(4-am)-Thiaz Dihydrochloride

N-(t-BUO$_2$C_CH$_2$)-N-Boc-(D)-Cha-Pro-NH—CH$_2$-2-(4-C(NH$_2$)NH)-thiaz×CH$_3$COOH (2.0 g, max 2.67 mmol) were [sic] heated for 4 hours at 40–50° C. in a mixture of 10 ml of dioxane and 20 ml of 5N aqueous hydrochloric acid solution, the mixture was subsequently extracted repeatedly with methylene chloride, and the aqueous phase was slightly concentrated in vacuo and subsequently freeze-dried. 1.4 g of HOOC—CH$_2$-(D)-Cha-Pro-NH—CH$_2$-2-(4-am)-thiaz dihydrochloride were obtained as a white amorphous solid substance, FAB-MS (M+H$^+$): 465.

EXAMPLE 2

N-(Hydroxycarbonylmethylene)-(D)-cyclohexylalanylprolyl-[4-(2-amidino)thienylmethyl]amide Hydroacetate a) N-(t-BuO$_2$C—CH$_2$)-N-Boc-(D)-Cha-Pro-NH—CH$_2$-4-(2-CN)-Thioph Starting from N-(t-BuO$_2$C—CH$_2$)-N-Boc-(D)-Cha-Pro-OH (6.35 g, 13.17 mmol) and 4-H$_2$N—CH$_2$-thioph-2-CN (2.3 g, 13.17 mmol), coupling was effected analogously to Example 1 to give N-(t-BuO$_2$C—CH$_2$)-N-Boc-(D)-Cha-Pro-NH—CH$_2$-4-(2-CN)-thioph, 6.95 g of the required product resulting after purification by chromatography.

b) N-(t-BuO$_2$C—CH$_2$)-N-Boc-(D)-Cha-Pro-NH—CH$_2$-4-(2-CSNH$_2$)-Thioph

N-(t-BuO$_2$C—CH$_2$)-N-Boc-(D)-Cha-Pro-NH—CH$_2$-4-(2-CN)-thioph (6.95 g, 11.53 mmol) were [sic] dissolved in 40 ml of pyridine and 7 ml of triethylamine, the solution was saturated with hydrogen sulfide at 0–5° C. (green solution) and left to stand at room temperature over the weekend. After concentration in vacuo at 35° C./35 mbar, the yellow oily residue was taken up in 200 ml of ether and washed four times with in each case 20 ml of 20% strength sodium hydrogen sulfate solution, twice with in each case 20 ml of saturated sodium hydrogen carbonate solution and with 20 ml of water, and the organic phase was dried over soduim sulfate and concentrated in vacuo. 6.74 g resulted as a yellow solid foam.

c) N-(t-BUO$_2$C—CH$_2$)-N-Boc-(D)-Cha-Pro-NH—CH$_2$-4-(2-C(SCH$_3$)NH)-Thioph Hydroiodide The crude product of N-(t-BuO$_2$C—CH$_2$)-N-Boc-(D)-Cha-Pro-NH—CH$_2$-4-(2-CSNH$_2$)-thioph (6.74 g, 10.58 mmol) was introduced into 65 ml of methylene chloride, 9.01 g (4.0 ml, 63.5 mmol) of methyl iodide were added, and the mixture was left to stand overnight at room temperature. It was then concentrated in vacuo under mild conditions, 8.36 g resulting as a yellow solid foam.

d) N-(t-BuO$_2$C—CH$_2$)-N-Boc-(D)-Cha-Pro-NH—CH$_2$-4-(2-C(NH$_2$)NH)-Thioph Hydroiodide The crude product of N-(t-BU02C—CH$_2$)-N-Boc-(D)-Cha-Pro-NH-CH$_2$-4-(2-C(SCH$_3$)NH)-thioph hydroiodide (8.36 g, max 10.58 mmol) together with 16.3 g (21.16 mmol) of a 10% strength ammonium acetate solution in methanol was stirred overnight at room temperature. Since the precursor had not reacted completely, another 1.63g of the 10% strength ammonium acetate solution were added and the mixture was again stirred overnight. After evaporation of the solvent in vacuo in a rotary evaporator, the residue was taken up in methylene chloride, insoluble excess ammonium acetate was removed by filtration, and the liquid was again concentrated in vacuo, 7.12 g of the required product resulting as:a yellow solid foam.

e) HOOC—CH$_2$-(D)-Cha-Pro-NH—CH$_2$-4-(2-am)-Thioph Hydroacetate

The crude product of N-(t-BuO$_2$C—CH$_2$)-Boc-(D)-Cha-Pro-NH—CH$_2$-4-(2-C(NH$_2$)NH)-thioph hydroiodide, which resulted from the above experiment, was dissolved in 100 ml of methylene chloride, 24.5 ml of etheric hydrochloric acid solution (approx. 5 N) were added, and the mixture was stirred overnight at room temperature. The resulting suspension was concentrated in vacuo and codistilled twice with methylene chloride, and the residue was converted into the acetate salt by means of acetate ion exchanger (Fluka, Product No. 00402), with 4.92 g being obtained. 2.5 g of this were purified by means of MPLC (RP-18, acetonitrile/water) and the fractions were freeze-dried. 1.23 g of the target product were obtained as amorphous white solid.

FAB-MS (M+H$^+$): 464.

EXAMPLE 3

N-(Hydroxycarbonylmethylene)-(D)-cyclohexylalanyl-pipecolic Acid [5-(2-Amidino) thienylmethyl]amide Hydroacetate a) H-Pic-NH—CH$_2$-5-(2-CN)-Thioph Boc-Pic-OH (10.1 g, 44.05 mmol) and 5-H$_2$N—CH$_2$-thioph-2-CN hydrochloride (8.54 g, 48.88 mmol) were dissolved in dichloromethane (150 ml), and ethyl diisopropylamine (53.2 ml, 311.08 mmol) and a 50% strength solution of propanephosphonic anhydride in ethyl acetate (46 ml, 217 mmol) were added at 0° C. After the reaction mixture had been stirred for 1 hour at 0° C. and for 1 hour at room temperature, it was diluted with dichloromethane and washed with 20% strength sodium hydrogen sulfate solution (4×), sodium hydrogen carbonate solution (3×) and saturated sodium chloride solution (1×). After drying over sodium sulfate and removal of the desiccant by filtration, the solvent was distilled out under water pump vacuum. To eliminate the Boc group, the residue (18.41 g) was treated with 200 ml of isopropanol and 50 ml of 6.8N isopropanolic hydrochloric acid solution and stirred overnight at room temperature. The mixture was then evaporated to dryness and codistilled twice with dichloromethane, and the residue was extracted by stirring with ether. 12.7 g of the required product resulted as a pale brown powder.

b) HOOC-H$_2$-(D)-Cha-Pic-NH—CH$_2$-5-(2-am)-Thioph Hydroacetate

This compound was prepared by coupling the two building blocks N-(t-BuO$_2$C—CH$_2$)-N-Boc-(D)-Cha-OH and H-Pic-NH—CH$_2$-5-(2-CN)-thioph analogously to Example 2a). The reaction to give the end product HOOC—CH$_2$-(D)-Cha-Pic-NH—CH$_2$-5-(2-m)-thioph hydroacetate was carried out analogously to Example 2b) to d), FAB-MS (M+H$^+$): 478.

EXAMPLE 4

N-(Hydroxycarbonylmethylene)-(D)-cyclohexylglycylprolyl-[2-(4-amidino) thienylmethyl]amide Hydrochloride a) HOOC—CH$_2$-(D)-Chg-Pyr-NH—CH$_2$-4-(2-am)-Thioph Dihydrochloride This compound was prepared over several steps analogously to Examples 2 and 3 starting from Boc-Pyr-OH, 4-H$_2$N—CH$_2$-thioph-2-N×HCl and N-(t-BuO$_2$-CH$_2$)-Boc-(D)-Chg-OH.

b) HOOC—CH$_2$-(D)-Chg-Pro-NH—CH$_2$-4-(2am)-Thioph Dihydrochloride 1.1 g (2.11 mmol) of HOOC—CH$_2$-(D)-Chg-Pyr-NH—CH$_2$-4-(2-am)-thioph dihydrochloride were dissolved in a mixture of 30 ml of water and 10 ml of glacial acetic acid, 0.5 g of 10% palladium on active charcoal was added, and the mixture was hydrogenated for 8 hours at room temperature under slightly elevated pressure. After the catalyst had been exchanged, hydrogenation continued for 8 hours, the catalyst was filtered off with suction, the mixture was filtered through Celite® and the aqueous-organic phase was subsequently freeze-dried. 0.86 g of the required product was obtained as a white amorphous solid.

FAB-MS (M+H$^+$): 450.

As an alternative to the procedure described here, Boc-proline may be employed directly instead of Boc-(L)-3,4-dehydroproline, which means that the hydrogenation step can be dispensed with.

EXAMPLE 5

N-(Hydroxycarbonylmethylene)-(D)-cyclohexylglycylprolyl-[2-(4-amidino) thiazolylmethyl]amide This compound can be prepared analogously to Example 1 starting from N-(t-BuO$_2$C—CH$_2$)-N-Boc-(D)-Chg-Pro-OH and 2-H$_2$N—CH$_2$-thiaz-4-CSNH$_2$.

EXAMPLE 6

N-(Hydroxycarbonylmethylene)-(D)-cyclohexylalanylprolyl-[4-(2-amidino) thienylmethyl]amide This compound can be prepared analogously to Example 2 starting from N-(t-BuO$_2$C—H$_2$)-N-Boc-(D)-Cha-Pro-OH and 4-H$_2$N—CH$_2$-thioph-2-CN or analogously to Example 4 by hydrogenating HOOC-CH$_2$-(D)-cha-Pyr-NH—CH$_2$-4-(2-am)-thioph.

EXAMPLE 7

N-(Hydroxycarbonylmethylene)-(D)-cyclohexylalanylprolyl-[5-(2-amidino-3,4-dimethyl) thienylmethyl]amide Starting from 5-H$_2$N—CH$_2$-(3,4-Me$_2$)-thioph-2-CONH$_2$ and N-(t-BuO$_2$C—CH$_2$)-N-Boc-(D)-Cha-Pro-OH, this compound can be converted into N-(t-BuO$_2$C—H$_2$)-N-Boc-(D)-Cha-Pro-NH—CH$_2$-5-(2-CONH$_2$-3,4-Me$_2$)-thioph analogously to Example 2a). After dehydration of the amide with trifluoroacetic anhydride and diisopropylethylamine in methylene chloride to give the nitrile functionality, the amidine functionality can be constructed analogously to Example 2 and the protective groups can subsequently be eliminated.

EXAMPLE 8a

N-(Hydroxycarbonylmethylene)-(D)-cycloheptylglycylprolyl-[4-(2-amidino) thienylmethyl]amide Hydroacetate

EXAMPLE 8b

N-(Hydroxycarbonylmethylene)-(L)-cycloheptylglycylprolyl-[4-(2-amidino) thienylmethyl]amide Hydroacetate Starting from 4-H$_2$N—CH$_2$-thioph-2-CN, Boc-Pyr-OH and N-(t-BuO$_2$C—CH$_2$)-N-Boc-(D,L)-Cheg-OH, these compounds can be prepared analogously to Example 3, hydrogenated in a final step analogously to Example 4 and subsequently separated by means of MPLC (RP 18, acetonitrile/water). If Boc-Pro-OH is employed in the synthesis instead of Boc-Pyr-OH, the hydrogenation step can be dispensed with.

EXAMPLE 9a

N-(Hydroxycarbonylmethylene)-(D)-cyclopentylglycylprolyl-[4-(2-amidino) thienylmethyl amide Hydroacetate

EXAMPLE 9b

N-(Hydroxycarbbnylmethylene)-(L)-cyclopentylglycylprolyl-[4-(2-amidino) thienylmethyl]amide Hydroacetate Starting from 4-H$_2$N—CH$_2$-thioph-2-CN, Boc-Pyr-OH and N-(t-BuO$_2$C—CH$_2$)-N-Boc-(D,L)-Cpg-OH, these compounds can be prepared analogously to Example 3, hydrogenated in a final step analogously to Example 4 and subsequently separated by means of MPLC (RP 18, acetonitrile/water). If Boc-Pro-OH is employed in the synthesis instead of Boc-Pyr-OH, the hydrogenation step can be dispensed with.

EXAMPLE 10

N-(Hydroxycarbonylmethylene)-(D)-cyclohexylalanylprolyl-[4-(2-amidino) thiazolylmethyl]amide This compound can be prepared analogously to Example 1 starting 5 from N-(t-BuO$_2$C—H$_2$)-Boc-(D)-Cha-Pro-OH and 4-H$_2$N—CH$_2$-thiaz-2-CSNH$_2$.

EXAMPLE 11

N-(Hydroxycarbonylmethylene)-(D)-cyclohexylglycylprolyl-[4-(2-amidino) thiazolylmethyl]amide This compound can be prepared analogously to Example 1 starting from N-(t-BuO$_2$C—H$_2$)-N-Boc-(D)-Chg-Pro-OH and 4-H$_2$N—CH$_2$-thiaz-2-CSNH$_2$.

EXAMPLE 12

N-(Hydroxycarbonylmethylene)-(D)-cyclohexylalanylprolyl 5-(3-Amidino) isoxazolylmethyl]amide Starting from N-(t-BuO$_2$C—H$_2$)-N-Boc-(D)-Cha-Pro-OH and 5-H$_2$N—CH$_2$-isox-3-CONH$_2$, this compound can be converted analogously to Example 2a) into N-(t-BuO$_2$C—CH$_2$)-N-Boc-(D)-Cha-Pro-NH—CH$_2$-5-(3-CONH$_2$)-isox. After dehydration of the amide to give the nitrile functionality using trifluoroacetic anhydride and diisopropylethylamine in methylene chloride, the amidine functionalities can be constructed analogously to Example 20 by reaction with ammonia and acetylcysteine and the protective groups can subsequently be eliminated.

EXAMPLE 13

N-[5-(3-Amidino)thienylmethyl]-1-[N-(hydroxycarbonylmethylene)-(D)-cyclohexylglycyl] azetidine-2-caboxamide [sic]

a) N-[5-(3-Cyano)thienylmethyl]-1-[N-t-butoxycarbonyl)-(D)-cyclohexylglycyl]azetidine-2-carboxamide 5.9 g (45.8 mmol) of diisopropylethylamine and subsequently 11.5 ml (14.9 mmol) of 50% strength propanephosphonic anhydride-solution in ethyl acetate were added dropwise at −5° C. to a solution of 3.9 g (11.5 mmol) of 1-[N-(t-butoxycarbonyl)-(D)-cyclohexylglycyl]azetidine-2-carboxylic acid (WO 9429336) and 2 g (11.5 mmol) of 5-aminomethyl-3-cyanothiophene hydrochloride in 40 ml of-methylene chloride. Stirring was continued for 2 hours, during which process the temperature climbed to 10° C. The organic phase was washed with water, 5% strength sodium bicarbonate solution and 5% strength citric acid solution, dried over sodium sulfate and evaporated to dryness. Purification of the residue by column chromatography (silica gel, eluent: ethyl acetate) afforded 4.5 g (85% of theory) of white, amorphous powder, FAB-MS: 461 (M+H$^+$).

b) N-[5-(3-Cyano)thienylmethyl]-1-[N-(t-butoxycarbonylmethylene)-(D)-cyclohexylglycyl]azetidine-2-carboxamide 4.5 g (3.8 mmol) of the above compound were dissolved in 70 ml of isopropanol, 12.3 ml of 4N hydrochloric acid in dioxane were added, and the mixture was left to stand overnight at room temperature. After the solvent had been distilled out, the residue was dissolved in methylene chloride and the mixture was extracted 3× with water. The combined aqueous extracts were rendered alkaline with 1N sodium hydroxide solution, the oily base [sic] which separated out was extracted 3× with methylene chloride, and the solvent was subsequently distilled out. 2.9 g (8 mmol) of oil remained. This was dissolved in 50 ml of methylene chloride and 10 ml of acetonitrile and, after addition of 2.1 g (16 mmol) of diisopropylethylamine and 1.5 g (7.6 mmol) of t-butyl bromo- acetate, left to stand for 24 hours at room temperature.

The organic phase was washed in each case 2× with 5% strength citric acid solution, 5% strength sodium hydrogen carbonate solution and water and dried over sodium sulfate and the solvent was distilled out. 3.3 g (92% of theory) of pale yellowish oil remained. FAB-MS: 475 (M+H$^+$).

c) N-[5-(3-Amidino)thienylmethyl]-1-[N-(hydroxycarbonylmethylene)-(D)-cyclohexylglycyl] azetidine-2-carboxamide The above product was coverted into the amidine analogously to Example 2. The resulting crude amidine contained substantial amounts of a secondary product and had to be purified by column chromatography (silica gel, eluent:

methylene chloride:methanol:acetic acid=24:6:1.5). 0.9 g of white, amorphous powder was isolated. The Boc protective group and the t-butyl ester group were eliminated by leaving the powder to stand for 12 hours in 3N hydrochloric acid. After finally removing the hydrochloric acid by distillation with addition of toluene, the hydrochloric residue was converted into the betaine by chromatography over a silica gel column with a methanol/25% ammonia eluent (50/2.5). 0.45 g of white, amorphous powder resulted, FAB-MS: 463 (M+H$^+$).

EXAMPLE 14

N-(Hydroxycarbonylmethylene)-(D)-yclohexylalanylprolyl-[5-(3-amidino)furylmethyl] amide Hydroacetate a) Prolyl-[5-(3-cyano)furylmethyl]amide Hydrochloride 3.05 g (14 mmol) of Boc-Pro-OH and 6.11 g (47.3 mmol) of ethyldiisopropylamine were added at room temperature to a suspension of 2.5 g (15.8 mmol) of 5 minomethyl-3-cyanofuran hydrochloride in 50 ml of dichloromethane. 15.8 ml (74.5 mmol) of a 50% strength solution of propanephosphonic anhydride in ethyl acetate were added dropwise at 5° C., with gentle cooling. After stirring for 30 minutes at room temperature, the mixture was diluted with ethyl acetate and washed three times with 5% strength citric acid solution, three times with saturated sodium hydrogen carbonate solution and once with saturated sodium chloride solution. After drying over sodium sulfate and removal of the desiccant by filtration, the solvent was distilled out under water pump vacuum. 4.3 g (86%) of a pale yellow oil resulted, and this was directly reacted further.

The oil obtained in accordance with a) (4.3 g, 13.5 mmol) was dissolved in 40 ml of ethyl acetate to eliminate the Boc group, and saturated with hydrogen chloride at 0° C. The reaction mixture was stirred overnight and evaporated to dryness in a rotary evaporator. 3.4 g (99%) of the title compound resulted.

b) N-(tert-Butoxycarbonylmethylene)-(N-Boc)-(D)-cyclohexylalanylprolyl-[5-(3-cyano)furylmethyl]amide 2.58 g (6.7 mmol) of t-BuO$_2$C—H$_2$-Boc-(D)-Cha-OH and 1.7 g (6.7 mmol) of prolyl-[5-(3-cyano)furylmethyl] amide hydrochloride were suspended in 20 ml of dichloromethane and 3.45 g (26.8 mmol) of ethyldiisopropylamine were added. The reaction mixture was cooled to approx. 5° C., and 6.7 ml of a 50% strength solution of propanephosphonic anhydride in ethyl acetate was added dropwise, during which process the solution turned clear. After stirring overnight at room temperature, the mixture was diluted with ethyl acetate and then washed in each case three times with 20% strength sodium hydrogen sulfate solution, saturated sodium hydrogen carbonate solution and once with saturated sodium chloride solution. After drying over sodium sulfate, the desiccant was removed and the solvent was then distilled out under water pump vacuum. 3.7 g of the required product resulted as an oil.

c) N-(tert-Butoxycarbonylmethylene)-(N-Boc)-(D)-cyclohexylalanylprolyl-[5-(3-midothiocarbonyl) furylmethyl]amide The product obtained in accordance with b) was dissolved in pyridine (30 ml) and triethylamine (15 ml). The reaction mixture was saturated with hydrogen sulfide at room temperature and stirred overnight at room temperature. The excess hydrogen sulfide was displaced by nitrogen and the reaction mixture was poured into 300 ml of ice-cold 5% strength sodium hydrogen sulfate solution. The mixture was extracted three times with ethyl acetate and the combined organic phases were washed once more with 5% strength sodium hydrogen sulfate solution. After drying over sodium sulfate, the solvent was distilled out under water pump vacuum. The resulting crude product (3.3 g) was employed in the next step without further purification.

d) N-(tert-Butoxycarbonylmethylene)-(N-Boc)-(D)-cyclohexylalanylprolyl-[5-(3-S-methyliminothiocarbonyl) furylmethyl]-amide Hydroiodide The crude product obtained in accordance with c) was dissolved in 50 ml of acetone, and 8.3 g (58.7 mmol) of methyl iodide were added. After stirring overnight at room temperature, the solvent was distilled out under water pump vacuum. The residue was dissolved in a little ethyl acetate and the solution was added dropwise to diisopropyl ether, during which process a precipitate formed which was filtered off with suction and washed with diisopropyl ether. Drying at room temperature in vacuo resulted in 3.3 g of a solid foam.

e) N-(tert-Butoxycarbonylmethylene)-(N-Boc)-(D)-cyclohexylalanylprolyl-[5-(3-amidino)furylmethyl]amide Hydroacetate The crude product obtained in accordance with d) (3.3 g, 4.3 mmol) was dissolved in 40 ml of acetonitrile, 0.99 g (12.9 mmol) of ammonium acetate were added, and the mixture was stirred for two hours at 40° C. The solvent was then distilled out under water pump vacuum, the residue was taken up in diethyl ether, the salts were filtered off with suction and the filtrate was concentrated. The crude product was purified by means of reversed phase HPLC (acetonitrile/water and acetic acid buffer), which resulted in 991 mg of a yellow solid foam.

f) N-(Hydroxycarbonylmethylene)-(D)-cyclohexylalanylprolyl-[5-(3-amidino)furylmethyl]amide Hydroacetate 20 ml of a 1N aqueous hydrochloric acid solution were added to the product obtained in accordance with e) (991 mg, 1.68 mmol). After stirring for three hours at 45° C., the mixture was diluted with water and the resulting mixture was freeze-dried. The resulting crude product was dissolved in methanol and converted into the acetate salt over an ion exchanger (Fluka, Product No. 00402). 484 mg of the required product resulted.

FAB-MS (M+H$^+$): 446.

EXAMPLE 15

N-(Hydroxycarbonylmethylene)-(D)-cyclohexylglycylprolyl-(5-(3-amidino)furylmethyl] amide Hydroacetate

FAB-MS (M+H$^+$): 434.

This can be prepared analogously to Example 14, N-(tert-butoxycarbonylmethylene)-(N-Boc)-(D)-cyclohexylglycine being employed instead of N-(tert-butoxycarbonylmethylene)-(N-Boc)-(D)-cyclohexylalanine in b).

EXAMPLE 16

N-(Hydroxycarbonylmethylene)-(D)-cyclohexylalanylprolyl-[5-(2-amidino-1-methyl) pyrrolylmethyl]amide a) N-Boc-N-(tert-Butyloxycarbonylmethylene)-(D)-cyclohexylalanylproline (2.5 g, 5.18 mmol) was dissolved in dry methylene chloride (30 ml), cooled to −10° C., and N-ethyldiisopropylamine (3.9 ml, 22.27 mmol) was added at this temperature. After stirring for 5 minutes, a solution of 5-aminomethyl-1-methylpyrrole-2-carbonitrile (0.7 g, 5.18 mmol) in methylene chloride (15 ml) was added. A 50% strength propanephosphonic anhydride solution in ethyl acetate (4.6 ml, 6.21 mmol) was subsequently added dropwise in the course of 20 minutes. After stirring for 90 minutes at −10° C. to 0° C., the mixture was diluted with methylene chloride and washed 2× with saturated sodium hydrogen carbonate solution (in each case 15 ml), 2× with 5% strength citric acid solution (in each case 15 ml) and 1× with saturated sodium chloride solution (15 ml). After drying over sodium sulfate, the mixture was concentrated in vacuo and the crude product was purified by chromatography (silica gel, methylene chloride:methanol=95:5). Yield: 2.3 g (74%).

b) The product obtained in accordance with a) (2.3 g, 3.83 mmol) was dissolved in a mixture of dry methylene chloride and methanol (1:1, 50 ml), hydroxylamine hydrochloride (664 mg, 9.56 mmol) and N-ethyldiisopropylamine (4 ml, 23.0 mmol) were added, and the mixture was stirred for 7 hours at 40° C. and subsequently for 48 hours at room temperature. The solvent was distilled out in vacuo, water was added to the residue, and the mixture was acidified to pH 5 with acetic acid. The aqueous solution was extracted with methylene chloride (2×) and ethyl acetate (1×). The combined organic phases were dried over sodium sulfate and the solvent was distilled out in vacuo. The crude product was purified by chromatography (silica gel, methylene chloride:methanol=95:5). Yield: 1.6 g (white foam, 66%), FAB-MS (M+H$^+$): 633.

c) The product obtained in accordance with b) (1.6 g, 2.53 mmol) was dissolved in dry methanol (35 ml), acetic acid (0.3 ml, 5.06 mmol) and Raney nickel (84 mg) were added, and the mixture was hydrogenated at 50° C. under 1 atmosphere of hydrogen (2.5 hours). After cooling, the catalyst was removed by filtration through Celite® and the filtrate was concentrated in vacuo. Yield: 1.7 g (white foam, 99%), FAB-MS (M+H$^+$): 617.

d) The product obtained in accordance with c) (1.7 g, 2.50 mmol) was dissolved in dry methylene chloride (50 ml). The solution was cooled to 0° C. and saturated with dry HCl gas. After stirring for 2 hours, the solvent was distilled out in vacuo and the crude product was purified by chromatography (RP18, acetonitrile:water=1:9 with addition of 0.1% acetic acid).

Yield: 760 mg (57%), melting point: 184–185° C., FAB-MS (M+H$^+$): 461.

EXAMPLE 17

N-(Hydroxycarbonylmethylene)-(D)-cyclohexylalanylprolyl-[2-(4-amidino-1-methyl)pyrrolemethyl]amide was prepared analogously to Example 16, FAB-MS (M+H$^+$): 461.

EXAMPLE 18

N-(Hydroxycarbonylmethylene)-(D)-cyclohexylalanylprolyl-[4-(2-amidino-1-methyl)pyrrolylmethyl]amide can be Prepared Analogously to Example 16.

EXAMPLE 19

N-(tert-Butoxycarbonylmethylene)-(N-Boc)-(D)-cyclohexylalanylprolyl-[2-(4-amido)oxazolylmethyl]amide Hydrochloride can be Prepared Analogously to Example 1 Starting From N-(t-BuO$_2$C—CH$_2$-N-Boc-(D)-Cha-Pro-OH and 2-Aminomethyl-4-thiocarboxamidoxazole

EXAMPLE 20

N-(Hydroxycarbonylmethylene)-(D)-cyclohexylalanylprolyl-[5-(3-amidino-1-methyl)pyrazolylmethyl]amide Hydrochloride a) N-(tert-Butoxycarbonylmethylene)-(N-Boc)-(D)-cyclohexylalanylprolyl-[5-(3-amido-1-methyl)pyrazolylmethyl]amide N-(t-BuO$_2$C—CH$_2$)-N-Boc-(D)-Cha-Pro-OH (1.25 g, 2.59 mmol) was introduced into dichloromethane (30 ml). Diisopropylethylamine (1.95 ml, 11.16 mmol) was added dropwise at −10° C. A solution of 1-methyl-5-aminomethylpyrazole-3-carboxamide (0.4 g, 2.59 mmol) in tetrahydrofuran (20 ml) was subsequently added. After stirring for 5 minutes, a 50% strength solution of propanephosphonic anhydride ethyl acetate solution [sic] (2.36 ml, 3.11 mmol), as well as dichloromethane (5 ml), were added dropwise in the course of 5 minutes. After stirring for 45 minutes at 0° C., the mixture was warmed at RT for 12 hours. The solvent was removed in a rotary evaporator, the residue was taken up in dichloromethane and the mixture was washed 2× with saturated sodium hydrogen carbonate solution, 2× with 5% strength citric acid solution and 1× with saturated sodium chloride solution. After drying over sodium sulfate, the solvent was removed in a rotary evaporator. The crude product was purified by chromatography (RP-18, acetonitrile, water).

Yield: 220 mg (14%). FAB-MS (M+H$^+$): 619.

b) N-(tert-Butoxycarbonylmethylene)-(N-Boc)-(D)-cyclohexylalanylprolyl-[5-(3-cyano-1-methyl)pyrazolylmethyl]amide The product obtained in accordance with a) (220 mg, 0.36 mmol) was dissolved in dichloromethane (15 ml), and diisopropylethylamine (0.17 ml, 0.96 mmol) was added at −10° C. After stirring for 5 minutes, a solution of trifluoroacetic anhydride (0.057 ml, 0.41 mmol) in dichloromethane (1 ml) was added dropwise. After 1 hour at 0° C., the mixture was diluted with dichloromethane and washed 2× with saturated sodium hydrogen carbonate solution, 2× with 5% strength citric acid solution and 1× with saturated sodium chloride solution. After drying over sodium sulfate, the solvent was removed in a rotary evaporator. Yield: 180 mg (84%).

c) N-(tert-Butoxycarbonylmethylene)-(N-Boc)-(D)-cyclohexylalanyprolyl-[5-(3-amidino-1-methyl)pyrazolylmethyl]amide Hydroacetate The product obtained in accordance with b) (180 mg, 0.3 mmol) was dissolved in methanol (1 ml), and acetylcysteine (52.8 mg, 0.32 mmol) was added. Ammonia was subsequently passed in at 35° C. until the reaction was complete. The solvent was removed in a rotary evaporator and the crude product was converted into the acetate using an ion exchanger (acetate on polymeric support, Fluka 00402). The crude product was purified by chromatography (RP-18, acetonitrile, water). Yield: 50 mg (16%), FAB-MS (M+H$^+$): 618.

d) N-(Hydroxycarbonylmethylene)-(D)-cyclohexylalanylprolyl-[5-(3-amidino-1-methyl)pyrazolylmethyl]amide Hydrochloride The product obtained in accordance with c) (50 mg, 0.081 mmol) was dissolved in dichloromethane (5 ml), and 5M hydrochloric acid in diethyl ether (0.147 ml) was added. After stirring for 12 hours at RT, the solvent was removed in a rotary evaporator, and the product was taken up in water and lyophilized. Yield: 40 mg (92%), FAB-MS (M+H$^+$): 462.

EXAMPLE 21

N-(Hydroxycarbonylmethylene)-(D)-cyclohexylalanylprolyl-[5-(3 midino)-1,2,4-oxadiazolylmethyl amide Hydrochloride can be Prepared Analogously to Example 20 Starting From t-BuO$_2$C—CH$_2$-(Boc)-(D)-Cha-Pro-OH and 5-Amino-3-cyano-1,2,4-oxadiazole

EXAMPLE 22

N-(Hydroxycarbonylmethylene)-(D)-cyclohexylglycylprolyl-[5-(2-amidino-3-methyl)thienylmethyl]amide This compound was synthesized starting from N-(t-BuO$_2$C—CH$_2$) N-Boc-(D)-Chg-Pro-OH and 5-aminomethyl-3-methylthiophene-2-carbonitrile hydrochloride by a method similar to that described in Ex. 2a)–e).

FAB-MS (M+H$^+$): 464.

EXAMPLE 23

N-(Hydroxycarbonylmethylene)-(D)-cyclohexylalanylprolyl-[5-(2-amidino-3-methyl)thienylmethyl]amide This compound was synthesized starting from N-(t-BuO$_2$C—CH$_2$)-N-Boc-(D)-Cha-Pro-OH and 5-aminomethyl-3-methylthiophene-2-carbonitrile hydrochloride by a method similar to that described in Ex. 2 a)–e).

FAB-MS (M+H$^+$): 478.

EXAMPLE 24

N-(Hydroxycarbonylmethylene)-(D)-cyclohexylalanylprolyl-[5-(3 amidino-1-methyl)triazylmethyl]amide This compound was synthesized starting from N-(t-Bub$_2$C—CH$_2$)-N-Boc-(D)-Cha-Pyr-OH and 5-aminomethyl-1-methyl-1H-[1,2,4]triazole-3-carboxamide. First, a method similar to that described in Ex. 20a)–d) was followed, and N-(hydroxycarbonylmethylene)-(D)-cyclohexylalanyldehydroprolyl-[5-(3-amidino-1-methyl)triazylmethyl]amide was obtained. This compound was converted into the title compound by a method similar to that described in Ex. 4b).

FAB-MS (M+H$^+$): 463.

EXAMPLE 25

N-(Hydroxycarbonylmethylene)-(D)-cyclohexylglycylprolyl-[5-(3 amidino-1-methyl)triazylmethyl]amide This compound was synthesized starting from N-(t-BuO$_2$C—CH$_2$)-N-Boc-(D)-Chg-Pyr-OH and 5-aminomethyl-1-methyl-1H-[1,2,4]triazole-3-carboxamide. First, a method similar to that described in Ex. 20a)–d) was followed, and N-(hydroxycarbonylmethylene)-(D)-cyclohexylglycyldehydroprolyl-[5-(3-amidino-1-methyl)triazylmethyl]amide was obtained. This compound was converted into the title compound by a method similar to that described in Ex. 4b).

FAB-MS (M+H$^+$): 449.

EXAMPLE 26

N-(Hydroxycarbonylmethylene)-(D)-cyclohexylalanylprolyl-[5-(3-amidino-4-chloro)thienylmethyl]amide This compound was synthesized starting from N-(t-BuO$_2$C—CH$_2$)-N-Boc-(D)-Cha-Pro-OH and 5-aminomethyl-4-chlorothiophene-3-thiocarboxamide hydrochloride by a method similar to that described in Example 1a)–d).

ESI-MS (M+H$^+$): 498.

EXAMPLE 27

N-(Ethoxycarbonylmethylene)-(D)-cyclohexylalanylprolyl-[5-(3-amidino-4-chloro)thienylmethyl]amide This compound was synthesized by passing hydrogen chloride to saturation into a solution, cooled to 0° C., of 100 mg (0.186 mmol) of N-(hydroxycarbonylmethylene)-(D)-cyclohexylalanylprolyl-[5-(3amidino-4-methyl)thienyl]methylamide (Example 26 above) in 10 ml of ethanol and stirring for five hours at room temperature. The mixture was concentrated and co-distilled three times with a little toluene each time in order to remove residual hydrogen chloride. The residue (89 mg, 85%) was dissolved in ethanol and converted into the corresponding acetate by means of an acetate ion exchanger (Fluka, Product No. 00402). FAB-MS (M+H$^+$): 506.

EXAMPLE 28

N-(Hydroxycarbonylmethylene)-(D)-cyclohexylalanylproly-1[5-(3-amidino-4-methyl)thienylmethyl]amide This compound was synthesized starting from N-(t-BuO$_2$C—CH$_2$)-N-Boc-(D)-Cha-Pro-OH and 5-aminomethyl-4-methylthiophene-3-thiocarboxamide hydrochloride by a method similar to that described in Example 1a)–d). ESI-MS (M+H$^+$): 478.

EXAMPLE 29

N-(Ethoxycarbonylmethylene)-(D)-cyclohexylalanylprolyl-[5-(3-amidino-4-methyl)thienylmethyl]amide This compound was synthesized by passing hydrogen chloride to saturation into a solution, cooled to 0° C., of 100 mg (0.186 mmol) of N-(hydroxycarbonylmethylene)-(D)-cyclohexylalanylprolyl-[5-(3-amidino-4-methyl)thienyl]methylamide (Example 28 above) in 10 ml of ethanol and stirring the mixture for 5 hours at room temperature. The mixture was concentrated and co-distilled three times with a little toluene each time in order to remove residual hydrogen chloride. The residue (89 mg, 85%) was dissolved in ethanol and converted into the corresponding acetate by means of an acetate ion exchanger (Fluka, Product No. 00402).

FAB-MS (M+H$^+$): 506.

EXAMPLE 30

N-(Hydroxycarbonylmethylene)-(D)-cyclohexylalanylprolyl-[5-(2-amidino-3-chloro)thienylmethyl]amide This compound can be prepared by the following reaction sequence: coupling of N-(t-BuO$_2$C—CH$_2$)-Boc-(D)-Cha-Pro-OH with 5-H$_2$N—CH$_2$-(2-CN-3-Cl)-thioph to give N-(t-BuO$_2$C—CH$_2$)-Boc-(D)-Cha-Pro-NH—CH$_2$-5-(2-CN-3-Cl)-thioph, amidine formation and subsequent elimination of the protective groups by a method similar to that described in Example 2.

EXAMPLE 31

N-(Hydroxycarbonylmethylene)-(D)-yclohexylglycylprolyl-[5-(2-amidino-3-chloro)thienylmethyl]amide This compound can be prepared by the following reaction sequence: coupling of N-(t-BuO$_2$C—CH$_2$)-N-BQc-(D)-

Chg-Pro-OH with 5-H₂N—CH₂-(2-CN-3-Cl)-thioph to give N-(t-BuO₂C—CH₂)-N-Boc-(D)-Chg-Pro-NH—CH₂-5-(2-CN-3-Cl)-thioph, amidine formation and subsequent elimination of the protective groups by a method similar to that described in Example 2.

EXAMPLE 32

N-(Methoxycarbonylmethylene)-(D)-cyclohexylalanylprolyl-[4-(2-amidino)thienylmethyl]amide This compound can be synthesized from N-(t-BuO₂C—CH₂)-N-Boc-(D)-Cha-Pro-NH—CH₂-4-(2-am)-thioph by elimination of the protective groups and transesterification (HCl in methanol at room temperature).

EXAMPLE 33

N-(Methoxycarbonylmethylene)-(D)-cyclohexylglycylprolyl[4-(2-amidino)thienylmethyl]amide This compound can be synthesized from N-(t-BuO₂C—CH₂)-N-Boc-(D)-Chg-Pro-NH—CH₂-4-(2-am)-thioph by elimination of the protective groups and transesterification (HCl in methanol at room temperature).

EXAMPLE 34

N-(Methoxycarbonylmethylene)-(D)-cyclohexylalanyl-azetidine-2-carboxylic Acid 4-(2-amidino)thienylmethylamide This compound can be synthesized from N-(t-BuO₂C—CH₂)-N-Boc-(D)-Cha-Aze-NH—CH₂-4-(2-am)-thioph by elimination of the protective groups and transesterification (HCl in methanol at room temperature).

EXAMPLE 35

N-(Methoxycarbonylmethylene)-(D)-cyclohexylglycyl-azetidine-2-carboxylic acid 2-(4-amidino)thienylmethylamide This compound can be synthesized from N-(t-BuO₂C—CH₂)-N-Boc-(D)-Chg-Aze-NH—CH₂-4-(2-am)-thioph by elimination of the protective groups and transesterification (HCl in methanol at room temperature).

EXAMPLE 36

N-(Methoxycarbonylmethylene)-(D)-cyclohexylalanylprolyl-[2-(4-amidino)thiazolylmethylamide This compound can be synthesized from N-(t-BuO₂C—CH₂)-N-Boc-(D)-Cha-Pro-NH—CH₂-2-(4-am)-thiaz by elimination of the protective groups and transesterification (HCl in methanol at room temperature).

EXAMPLE 37

N-(Methoxycarbonylmethylene)-(D)-cyclohexylglycylprolyl-[2-(4-amidino)thiazolylmethylamide This compound can be synthesized from N-(t-BuO₂C—CH₂)-N-Boc-(D)-Chg-Pro-NH—CH₂-2-(4-am)-thiaz by elimination of the protective groups and transesterification (HCl in methanol at room temperature).

EXAMPLE 38

N-(Methoxycarbonylmethylene)-(D)-cyclohexylalanyl-azetidine-2-carboxylic acid 2-(4-amidino)thiazolylmethylamide This compound can be synthesized from N-(t-BuO₂C—CH₂)-N-Boc-(D)-Cha-Aze-NH—CH₂-2-(4-am)-thiaz by elimination of the protective groups and transesterification (HCl in methanol at room temperature).

EXAMPLE 39

N-(Methoxycarbonylmethylene)-(D)-cyclohexylglycyl-azetidine-2-carboxylic acid 2-(4-amidino)thiazolylmethylamide This compound can be synthesized from N-(t-BuO₂C—CH₂)-N-Boc-(D)-Chg-Aze-NH—CH₂-2-(4-am)-thiaz by elimination of the protective groups and transesterification (HCl in methanol at room temperature).

EXAMPLE 40

N-(Hydroxycarbonylmethylene)-(D)-cyclohexylalanylprolyl-[4-(2-hydroxyamidino)thienylmethyl]amide This compound can be synthesized by reacting (t-BuO₂C—CH₂-)-(Boc)-(D)-Cha-Pro-NH—CH₂-(2-CN)-4-thioph with hydroxylamine hydrochloride (methanol, diisopropylethylamine, room temperature) and subsequent elimination of the protective groups (HCl in dichloromethane at room temperature).

EXAMPLE 41

N-(Methoxycarbonylmethylene)-(D)-cyclohexylalanylprolyl-[4-(2-hydroxyamidino)thienylmethyl]amide This compound can be synthesized by reacting (t-BuO₂C—CH₂-)-(Boc)-(D)-Cha-Pro-NH—CH₂-(2-CN)-4-thioph with hydroxylamine hydrochloride (methanol, diisopropylethylamine, room temperature) and subsequent elimination of the protective groups and transesterification (HCl in methanol at room temperature).

EXAMPLE 42

N-(Ethoxycarbonylmethylene)-(D)-cyclbhexylalanylprolyl-[4-(2-hydroxyamidino)thienylmethyl]amide This compound can be synthesized by reacting (t-BuO₂C—CH₂-)-(Boc)-(D)-Cha-Pro-NH—CH₂-(2-CN)-4-thioph with hydroxylamine hydrochloride (methanol, diisopropylethylamine, room temperature) and subsequent elimination of the protective groups and transesterification (HCl in ethanol at room temperature).

EXAMPLE 43

N-(Hydroxycarbonylmethylene)-(D)-cyclohexylglycylprolyl-[4-(2-hydroxyamidino)thienylmethyl]amide This compound can be synthesized by reacting (t-BuO₂C—CH₂-)-(Boc)-(D)-Chg-Pro-NH—CH₂-(2-CN)-4-thioph with hydroxylamine hydrochloride (methanol, diisopropylethylamine, room temperature) and subsequent elimination of the protective groups (HCl in dichloromethane at room temperature).

EXAMPLE 44

N-(Methoxycarbonylmethylene)-(D)-cyclohexylglycylprolyl-[4-(2-hydroxyamidino)thienylmethyl]amide This compound can be synthesized by reacting (t-BuO$_2$C—CH$_2$-)-(Boc)-(D)-Chg-Pro-NH—CH$_2$-(2-CN)-4-thioph with hydroxylamine hydrochloride (methanol, diisopropylethylamine, room temperature) and subsequent elimination of the protective groups and transesterification (HCl in methanol at room temperature).

EXAMPLE 45

N-(Ethoxycarbonylmethylene)-(D)-cyclohexylglycylprolyl-[4-(2-hydroxyamidino)thienylmethyl]amide This compound can be synthesized by reacting (t-BuO$_2$C—CH$_2$-)-(Boc)-(D)-Chg-Pro-NH—CH$_2$-(2-CN)-4-thioph with hydroxylamine hydrochloride (methanol, diisopropylethylamine, room temperature) and subsequent elimination of the protective groups and transesterification (HCl in ethanol at room temperature).

EXAMPLE 46

N-(Hydroxycarbonylmethylene)-(D)-cyclohexylglycyl-azetidine-2-carboxylic Acid 4-(2-Hydroxyamidino)-thienylmethyl]amide This compound can be synthesized by reacting (t-BuO$_2$C—CH$_2$-)-(Boc)-(D)-Chg-Aze-NH—CH$_2$-(2-CN)-4-thioph with hydroxylamine hydrochloride (methanol, diisopropylethylamine, room temperature) and subsequent elimination of the protective groups (HCl in dichloromethane at room temperature).

EXAMPLE 47

N-(Methoxycarbonylmethylene)-(D)-cyclohexylglycyl-azetidine-2-carboxylic Acid [4-(2-Hydroxyamidino)-thienylmethyl]amide This compound can be synthesized by reacting (t-BuO$_2$C—CH$_2$-)-(Boc)-(D)-Chg-Aze-NH—CH$_2$-(2-CN)-4-thioph with hydroxylamine hydrochloride (methanol, diisopropylethylamine, room temperature) and subsequent elimination of the protective groups and transesterification (HCl in methanol at room temperature).

EXAMPLE 48

N-(Ethoxycarbonylmethylene)-(D)-cyclohexylglycyl-azetidine-2-carboxylic Acid [4-(2-Hydroxyamidino)-thienylmethyl]amide This compound can be synthesized by reacting (t-BuO$_2$C—CH$_2$-)-(Boc)-(D)-Chg-Aze-NH—CH$_2$-(2-CN)-4-thioph with hydroxylamine hydrochloride (methanol, diisopropylethylamine, room temperature) and subsequent elimination of the protective groups and transesterification (HCl in ethanol at room temperature).

EXAMPLE 49

N-(Hydroxycarbonylmethylene)-(D)-cyclohexylalanyl-azetidine-2-carboxylic Acid [4-(2-Hydroxyamidino)-thienylmethyl]amide This compound can be synthesized by reacting (t-BuO$_2$C—CH$_2$-)-(Boc)-(D)-Cha-Aze-NH—CH$_2$-(2-CN)-4-thioph with hydroxylamine hydrochloride (methanol, diisopropylethylamine, room temperature) and subsequent elimination of the protective groups (HCl in dichloromethane at room temperature).

EXAMPLE 50

N-(Methoxycarbonylmethylene)-(D)-cyclohexylalanyl-azetidine-2-carboxylic Acid 14-(2-Hydroxyamidino)-thienylmethyl]amide This compound can be synthesized by reacting (t-BuO$_2$C—CH$_2$-)-(Boc)-(D)-Cha-Aze-NH—CH$_2$-(2-CN)-4-thioph with hydroxylamine hydrochloride (methanol, diisopropylethylamine, room temperature) and subsequent elimination of the protective groups and transesterification (HCl in methanol at room temperature).

EXAMPLE 51

N-(Ethoxycarbonylmethylene)-(D)-cyclohexylalanyl-azetidine-2-carboxylic Acid [4-(2-Hydroxyamidino)-thienylmethyl]amide This compound can be synthesized by reacting (t-BUO$_2$C—CH$_2$-)-(Boc)-(D)-Cha-Aze-NH—CH$_2$-(2-CN)-4-thioph with hydroxylamine hydrochloride (methanol, diisopropylethylamine, room temperature) and subsequent elimination of the protective groups and transesterification (HCl in ethanol at room temperature).

EXAMPLE 52

N-(Hydroxycarbonylmethylene)-(D)-cyclohexylalanylprolyl-[2-(4-hydroxyamidino)thiazolylmethyl]amide This compound can be synthesized by reacting (t-BUO$_2$C—CH$_2$-)-(Boc)-(D)-Cha-Pro-NH—CH$_2$-(4-CN)-2-thiaz with hydroxylamine hydrochloride (methanol, diisopropylethylamine, room temperature) and subsequent elimination of the protective groups (HCl in dichloromethane at room temperature).

EXAMPLE 53

N-(Methoxycarbonylmethylene)-(D)-cyclohexylalanylprolyl-[2-(4-hydroxyamidino)thiazolylmethyl]amide This compound can be synthesized by reacting (t-BuO$_2$C—CH$_2$-)-(Boc)-(D)-Cha-Pro-NH—CH$_2$-(4-CN)-2-thiaz with hydroxylamine hydrochloride (methanol, diisopropylethylamine, room temperature) and subsequent elimination of the protective groups and transesterirfication (HCl in methanol at room temperature).

EXAMPLE 54

N-(Ethoxycarbonylmethylene)-(D)-cyclohexylalanylprolyl-(2-(4-hydroxyamidino)thiazolylmethyl]amide This compound can be synthesized by reacting (t-BuO$_2$C—CH$_2$-)-(Boc)-(D)-Cha-Pro-NH—CH$_2$-(4-CN)-2-thiaz with hydroxylamine hydrochloride (methanol, diisopropylethylamine, room temperature) and subsequent elimination of the protective groups and transesterification (HCl in ethanol at room temperature).

EXAMPLE 55

N-(Hydroxycarbonylmethylene)-(D)-cyclohexylglycylprolyl-[2-(4-hydroxyamidino)thiazolylmethyl]amide This compound can be synthesized by reacting (t-BuO$_2$C—CH$_2$-)-(Boc)-(D)-Chg-Pro-NH—CH$_2$-(4-CN)-2-thiaz with hydroxylamine hydrochloride (methanol, diisopropylethylamine, room temperature) and subsequent elimination of the protective groups (HCl in dichloromethane at room temperature).

EXAMPLE 56

N-(Methoxycarbonylmethylene)-(D)-
cyclohexylglycylprolyl-[2-(4-hydroxyamidino)
thiazolylmethyl]amide This compound can be synthesized by reacting (t-BuO$_2$C—CH$_2$-)-(Boc)-(D)-chg-Pro-NH—CH$_2$-(4-CN)-2-thiaz with hydroxylamine hydrochloride (methanol, dilsopropylethylamine, room temperature) and subsequent elimination of the protective groups and transesterification (HCl in methanol at room temperature).

EXAMPLE 57

N-(Ethoxycarbonylmethylene)-(D)-
cyclohexylglycylprolyl-[2-(4-hydroxyamidino)
thiazolylmethyl]amide This compound can be synthesized by reacting (t-BUO$_2$C—CH$_2$-)-5 (Boc)-(D)-Chg-Pro-NH—CH$_2$-(4-CN)-2-thiaz with hydroxylamine hydrochloride (methanol, diisopropylethylamine, room temperature) and subsequent elimination of the protective groups and transesterification (HCl in ethanol at room temperature).

EXAMPLE 58

N-(Hydroxycarbonylmethylene)-(D)-
cyclohexylglycyl-azetidine-2-carboxylic Acid [2-(4-Hydroxyamidino)-thiazolylmethyl]amide This compound can be synthesized by reacting (t-BuO$_2$C—CH$_2$-)-(Boc)-(D)-Chg-Aze-NH—CH$_2$-(4-CN)-2-thiaz with hydroxylamine hydrochloride (methanol, diisopropylethylamine, room temperature) and subsequent elimination of the protective groups (HCl in dichloromethane at room temperature).

EXAMPLE 59

N-(Methoxycarbonylmethylene)-(D)-
cyclohexylglycyl-azetidine-2-carboxylic Acid [2-(4-Hydroxyamidino)-thiazolylmethyl]amide This compound can be synthesized by reacting (t-BuO$_2$C—CH$_2$-)-(Boc)-(D)-Chg-Aze-NH—CH$_2$-(4-CN)-2-thiaz with hydroxylamine hydrochloride (methanol, diisopropylethylamine, room temperature) and subsequent elimination of the protective groups and transesterification (HCl in methanol at room temperature).

EXAMPLE 60

N-(Ethoxycarbonylmethylene)-(D)-
cyclohexylglycyl-azetidine-2-carboxylic Acid [2-(4-Hydroxyamidino)-thiazolylmethyl]amide This compound can be synthesized by reacting (t-BuO$_2$C—CH$_2$-)-(Boc)-(D)-Chg-Aze-NH—CH$_2$-(4-CN)-2-thiaz with hydroxylamine hydrochloride (methanol, diisopropylethylamine, room temperature) and subsequent elimination of the protective groups (HCl in ethanol at room temperature).

EXAMPLE 61

N-(Hydroxycarbonylmethylene)-(D)-
cyclohexylalanyl-azetidine-2-carboxylic Acid [2-(4-Hydroxyamidino)-thiazolylmethyl]amide This compound can be synthesized by reacting (t-BuO$_2$C—CH$_2$-)-(Boc)-(D)-Cha-Aze-NH—CH$_2$-(4-CN)-2-thiaz with hydroxylamine hydrochloride (methanol, dlisopropylethylamine, room temperature) and subsequent elimination of the protective groups (HCl in dichloromethane at room temperature).

EXAMPLE 62

N-(Methoxycarbonylmethylene)-(D)-
cyclohexylalanyl-azetidine-2-carboxylic Acid [2-(4-Hydroxyamidino)-thiazolylmethyl]amide This compound can be synthesized by reacting (t-BuO$_2$C—CH$_2$-)-(Boc)-(D)-Cha-Aze-NH—CH$_2$-(4-CN)-2-thiaz with hydroxylamine hydrochloride (methanol, diisopropylethylamine, room temperature) and subsequent elimination of the protective groups and transesterification (HCl in methanol at room temperature).

EXAMPLE 63

N-(Ethoxycarbonylmethylene)-(D)-
cyclohexylalanyl-azetidine-2-carboxylic Acid [2-(4-Hydroxyamidino)-thiazolylmethyl]amide This compound can be synthesized by reacting (t-BuO$_2$C—CH$_2$-)-(Boc)-(D)-Cha-Aze-NH—CH$_2$-(4-CN)-2-thiaz with hydroxylamine hydrochloride (methanol, diisopropylethylamine, room temperature) and subsequent elimination of the protective groups and transesterification (HCl in ethanol at room temperature).

EXAMPLE 64

N-(Hydroxycarbonylmethylene)-(R)-
cyclohexylalanyl-(3S)-2,3,4,5-tetrahydropyridazine-3-carboxylic Acid [4-(2-Amidino)thienylmethyl]
amide Hydrochloride a) N-Boc-N-(tert-Butoxycarbonylmethylene)-(D)-cyclohexylalanyl-(3S)-2,3,4,5-tetrahydropyridazine-3-carboxylic Acid 3.3 g (25.8 mmol) of diisopropylethylamine and 1.5 g (12.3 mmol) of dimethylaminopyridine were added at −5° C. to a solution of 9.95 g (25.8 mmol) of N-Boc-N-(tert-butoxy-carbonylmethylene)-(D)-cyclohexylalanine, 7.4 g (25.8 mmol) of (S)-4-benzyl-3-[(S)-2,3,4,5-tetrahydro-3-pyridazinyl]-2-oxazolidinone (Y. Nakamura, C. Shin, Chem. Lett. 1991, 1953) and 7.4 g (38.7 mmol) of EDC hydrochloride in 80 ml of CH$_2$Cl$_2$ and the mixture was stirred for 2 hours at −5° C. and for 12 hours at room temperature.

The reaction solution was diluted with 200 ml of ether, washed with 5% strength citric acid solution, 5% strength NaHCO$_3$ solution and water, and, after the mixture had been dried and the solvent stripped off, the residue was purified by column chromatography (methylene chloride acetone [sic], 50/2.5). This gave 4.0 g (24% of theory) of a yellowish oil, FAB-MS (M+H$^+$): 655. This was dissolved in 80 ml of THF and 27 ml of water, and, at 0° C., 2.8 ml of 30% strength H$_2$O$_2$ and 12.6 ml of 1N NaOH were successively added dropwise and stirring was continued for 2.5 hours. After addition of 15 g of a saturated aqueous Na$_2$S$_2$O$_3$ solution, the mixture was extracted with ether and the alkaline phase was separated off and acidified with 1M KHSO$_4$ solution. After repeated extraction with ether, drying and removal of the solvent by distillation, 2.2 g of a white amorphous powder remained.

b) HOOC—CH$_2$-(D)-Cha-(3S)-2,3,4,5-Tetrahydropyridazine-3-carboxylic Acid [2-(4am) Thienylmethyl]amide Hydrochloride 0.7 g (1.4 mmol) of the above acid and 0.3 g of 2-aminomethyl-4-amidinothiophene dihydrochloride were suspended in 4 ml of DMF. After addition of 0.145 g (1.44 mmol) of N-methylmorpholine at 0° C., almost complete solution took place, and 0.475 g (1.45 mmol) of 0-[cyanoethoxycarbonylmethylene)amino]-N,N,N',N'-tetramethyluroniumtetrafluoroborate [sic] (TOTU) and a further 0.14 g of N-methylmorpholine were added. The reaction mixture was stirred for 3 hours at 0° C. under nitrogen and most of the DMF was subsequently distilled off at a bath temperature of 35° C. and −1 mbar. The residue was purified by column chromatography (eluant: $CH_2Cl_2$/MeOH, 45/5, toward the end with addition of 0.7 parts of 50% strength acetic acid). This gave 0.75 g of a slightly yellowish amorphous powder.

The latter was dissolved in 5 ml of $CH_2Cl_2$ and 10 ml of trifluoroacetic acid and the solution was left to stand overnight at room temperature. After addition of 30 ml of toluene, the mixture was concentrated in vacuo, and the residue was treated with ether and subsequently converted into the betain on a silica gel column (eluant: MeOH/25% strength $NR_3$, 50/2). The betain was dissolved in 20 ml of water, brought to pH 4.5 with 1N HCl and lyophilized. This gave 0.36 g of amorphous powder, FAB-MAS (M+H$^+$): 476.

EXAMPLE 65

N-(Hydroxycarbonylmethylene)-(R)-cyclohexylalanyl-(3S)-pyrazolidine-3-carboxylic Acid 2-(4-Amidino-thienylmethyl)amide Hydrochloride 8.36 g (21.7 mmol) of N-Boc-N-(tert-butoxycarbonylmethylene)-(D)-cyclohexylalanine and 5 g (21.7 mmol) of methyl (3S)-1-tert-butoxycarbonylpyrazoline-3-carboxylate [H. O. Kim, C. Lum, M. S. Lee (1997), THL 38 (28), 4935] were dissolved in 60 ml of $CH_2Cl_2$, 6.1 g (31.8 mmol) of EDC.HCl were added with stirring at −80C, and, after a further 20 minutes, 4.0 g (31 mmol) of diisopropylethylamine were added. After the mixture had been stirred for 40 minutes, 0.8 g of DMAP was added and the mixture was left to stand for 2 days at room temperature. After addition of 200 ml of ether, the mixture was washed with 5% strength citric acid, 5% strength $NaHCO_3$ solution and water, and, after drying, the ether was distilled off. After purification by column chromatography (eluant: $CH_2Cl_2$/acetone, 50/2), 8.2 g (63% of theory) of a white, amorphous powder were isolated.

Hydrolysis: 8.0 g (13.4 mmol) of the ester were dissolved in 60 ml of dioxane and 12 ml of water, and 15 ml of 1N NaOH were added at 10° C. After 1.5 hours, the pH was brought to 8 with 1N HCl, the dioxane was distilled off, and the residue was diluted with 250 ml of water and extracted with ether. The aqueous phase was brought to pH 2.5 with 1N $KHSO_4$ solution, and the acid which had separated out was extracted with ether. After the ether had been stripped off, 7.7 g of amorphous acid remained. A sample recrystallized from water-saturated n-hexane melts at 115 to 120° C. and has an angle of rotation $[\alpha]_D^{20}$ of +112.4° C. (CHCl$_3$, c=1).

The coupling with 4-aminomethyl-2-amidinothiophene dihydrochloride was carried out by a method similar to that described in Example 64 step b). After purification by column chromatography (eluant: $CH_2Cl_2$/MeOH/50% strength acetic acid, 40/10/0.7, 4 g of N-Boc-N-(tert-butoxycarbonylmethylene)-(R)-cyclohexylalanyl-(3S)-pyrazolidine-3-carboxylic acid [4-(2-amidino)thienylmethyl]amide acetate were obtained starting from 4.15 g of the above acid.

Cleavage [sic] of the protective group: The above compound was dissolved in 12 ml of dioxane, 20 ml of 1N HCl were added, and the mixture was heated for 4.5 hours at 75° C. The solution was diluted with 50 ml of water, brought to pH 4 with an ion exchanger (3-A4 resin, BioRad), and the water was distilled off. The residue was dissolved in isopropanol and the hydrochloride was precipitated by addition of ether. After purification by column chromatography (eluant: $CH_2Cl_2$/MeOH/50% strength acetic acid, 35/15/7), the residue was dissolved in water, brought to pH 4 with 1N HCl and lyophilized. This gave 1.6 g of the amorphous hydrochloride, FAB-MS (M+H$^+$): 465.

The following were obtained by a method similar to that described in Example 65:

EXAMPLE 66

N-(Hydroxycarbonylmethylene)-(R)-cyclohexylalanyl-(3R)-pyrazolidine-3-carboxylic Acid [4-(2-Amidino)thienylmethyl]amide Hydrochloride White Amorphous Powder. FAB-MS (M+H$^+$): 465

EXAMPLE 67

N-(Hydroxycarbonylmethylene)-(R)-cyclohexylglycyl-(3R)-pyrazolidine-3-carboxylic Acid [4-(2-Amidino)-thienylmethyl]amide Hydrochloride White Amorphous Powder. FAB-MS (M+H$^+$): 451

EXAMPLE 68

N-(Hydroxycarbonylmethylene)-(R)-cyclohexylglycyl-(3S)-pyrazolidine-3-carboxylic Acid [4-(2-Amidino)-thienylmethyl]amide Hydrochloride White Amorphous Powder. FAB-MS (M+H$^+$): 451

EXAMPLE 69

N-(Hydroxycarbonylmethylene)-((R)-cyclohexylglycyl-(−)-thiazolidine-2-carboxylic Acid [4-(2-Amidino)thienylmethyl]amide Hydrochloride Starting Material: Methyl (−)-Thiazolidine-2-carboxylate [R. L. Johnson, E. E. Smissman (1978), J. Med. Chem. 21, 165]

EXAMPLE 70

N-(Hydroxycarbonylmethylene)-(R)-cyclohexylalanyl-(−)-thiazolidine-2-carboxylic Acid [4-(2-Amidino)thienylmethyl]amide White Amorphous Powder. FAB-MS (M+H$^+$): 482

EXAMPLE 71

N-(Hydroxycarbonylmethylene)-(R)-cyclohexylalanyl-(L)-octahydroindole-2-carboxylic Acid [4-(2-Amidino)-thienylmethyl]amide Hydrochloride White Amorphous Powder. FAB-MS (M+H$^+$): 518

EXAMPLE 72

N-(Hydroxycarbonylmethylene)-(R)-cyclohexylglycyl-(L)-octahydroindole-2-carboxylic Acid [4-(2-Amidino)-thienylmethyl]amide Hydrochloride White Amorphous Powder. FAB-MS (M+H$^+$): 504

EXAMPLE 73

N-(Hydroxycarbonylmethylene)-(D)-cyclohexylalanyl-(45)-5.5-dimethylthiazolidine-4-carboxylic [sic] Acid [2-(4-Amidino)thienylmethyl] amide This compound can be prepared by the following reaction sequence: coupling of N-(t-BuO$_2$C—CH$_2$)-N-Boc-(D)-Cha- OH with (5)-5.5-Me$_2$-thz-4-OMe- [sic] [J. Samanen u.a. (1990), Int. J. Peptide Protein Res. 35, 501 (1990)] to give N-(t-BuO$_2$C—CH$_2$)-Boc-(D)-Cha-(2,2-Me$_2$-thz-4)-OMe, alkaline hydrolysis of the methyl ester, coupling of the resulting acid with H$_2$N—CH$_2$-(2-CN)-2-thioph to give N-(t-BuO$_2$C—CH$_2$)-N-Boc-(D)-Cha-(2.2.Me$_2$-thz-4)-NE-CH$_2$-2-(4-CN)-thioph [sic], amidine formation and subsequent elimination of the protective groups by a method similar to that described in Example 2b–e. FAB-MS (M+H$^+$): 505; m.p. 184–7° C. (decomp.)

EXAMPLE 74

N-(Hydroxycarbonylmethylene)-(D)-cyclohexylglycyl-5,5-dimethylthiazolidine-4-carboxylic Acid [4-(2-Amidino)thienylmethyl]amide This compound can be prepared by the following reaction sequence: coupling of N-(t-BuO$_2$C—CH$_2$)-N-Boc-(D)-Chg-OH 10 with 5.5-Me$_2$-thz-4-OMe- [sic] to give N-(t-BuO$_2$C—CH$_2$)-N-Boc-(D)-Chg-(2,2-Me$_2$-thz-4)-OMe, alkaline hydrolysis of the methyl ester, coupling of the resulting acid with H$_2$N—CH$_2$-(2-CN)-4-thioph to give N-(t-BuO$_2$C—CH$_2$)-N-Boc-(D)-Chg-(5.5-Me$_2$-thz-4)-NH—CH$_2$-4-(2-CN)-thioph [sic], amidine formation and subsequent elimination of the protective groups by a method similar to that described in Example 2b-e. FAB-MS (M+H$^+$): 491, m.p. 164–166° C. (decomp.)

EXAMPLES 75–90

The following compounds can be synthesized from the corresponding A—B—D— and E—F— units using a method similar to that described in Example 14 in WO98/06741:

75. HOOC—CH$_2$-(D)-(p-OMe-Phe)-Pro-NH—CH$_2$-2-(4-am)-thioph
76. HOOC—CH$_2$-(D)-(p-OMe-m-Cl-Phe)-Pro-NH—CH$_2$-2-(4-am)-thioph
77. HOOC—CH$_2$-(D)-(p-OMe-Phe)-Pro-NH—CH$_2$-5-(2-am-3-Me)-thioph
78. HOOC—CH$_2$-(D)-(p-CF$_3$-Phe)-Pro-NH—CH$_2$-5-(2-am-3-Me)-thioph
79. HOOC—CH$_2$-(D)-(p-Cl-m-Cl-Phe)-Pro-NH—CH$_2$-5-(2-am-3-Me)-thioph
80. HOOC—CH$_2$-(D)-(p-CF$_3$-Phe)-Pro-NH—CH$_2$-2-(4-am)-thioph
81. HOOC—CH$_2$-(D)-Cha-Pro-NH—CH$_2$-2-(4-am-5-Me)-thiaz
82. HOOC—CH$_2$-(D)-Chg-Pro-NH—CH$_2$-2-(4-am-5-Me)-thiaz
83. HOOC—CH$_2$-(D)-(p-OMe-Phe)-Pro-NH—CH$_2$-2-(4-am-5-Me)-thiaz
84. HOOC—CH$_2$-(D)-(p-OMe-Phe)-Pro-NH—CH$_2$-2-(4-am)-thiaz
85. HOOC—CH$_2$-(D)-(p-CF$_3$-Phe)-Pro-NH—CH$_2$-2-(4-am)-thiaz
86. HOOC—CH$_2$-(D)-(p-CF$_3$-Phe)-Pro-NH—CH$_2$-2-(4-am-5-Me)-thiaz
87. HOOC—CH$_2$-(D)-(p-iPr-m-Me-Phe)-Pro-NH—CH$_2$-2-(4-am)-thiaz
88. HOOC—CH$_2$-(D)-(p-OMe-m-Cl-Phe)-Pro-NH—CH$_2$-2-(4-am)-thiaz
89. HOOC—CH$_2$-(D)-(p-Cl-m-Cl-Phe)-Pro-NH—CH$_2$-2-(4-am)-thiaz
90. HOOC—CH$_2$-(D)-(p-Cl-m-Cl-Phe)-Pro-NH—CH$_2$-2-(5-am-4-Me)-thiaz

EXAMPLE 91

The following compound can be synthesized from the corresponding E— unit and N-(t-BuO$_2$C—CH$_2$)-N-Boc-(D)-Cha-Pro-OH by a method similar to that described in Example 20:

HOOC—CH$_2$-(D)-Cha-Pro-NH—CH$_2$-3-(5 am-1-Me)-pyraz

EXAMPLE 92

HOOC—CH$_2$-(D)-Cha-Thz-4-NH—CH$_2$-5-(2-am)-thioph was synthesized from Boc-Thz-4-OH, 5-H$_2$N—CH$_2$-thioph-2-CN and N-(t-BUO$_2$C—CH$_2$)-N-Boc-(D)-Cha-Pro-OH by a method similar to that described in Example 3.

PHARMACOLOGICAL EXAMPLES

EXAMPLE A

Chromogenic Test for Kallikrein Inhibitors

Reagents: Human plasma kallikrein (No. K 3126, Sigma, Deisenhofen, Germany)

Substrate: Chromozym GK (No. 709875, Boehringer, Mannheim, Germany)

Buffer: 20 mM Tris(HCl [sic] pH=8.50

Experimental Procedure:

Chromogenic test for determining the kallikrein activity is carried out in microplates. 2 gl of the solution of the substance in DMSO are added to 93 μl of buffer, and this is mixed with a final concentration of 0.01 units/ml kallikrein. Incubation is for 10 minutes at 20 to 25° C. The test is started by adding 100 μl of substrate (500 μmol/l final concentration). After incubation for a further 30 minutes, the absorption is measured in a photometer at 405 nm.

EXAMPLE B

Thrombin Time

Reagents: Thrombin Reagent (Product No. 126 594, Boehringer, Mannheim, Germany)

Preparation of the Citrate Plasma:

9 parts of venous human blood from the vena cephalica are mixed with one part of sodium citrate solution (0.11 mol/l). The mixture is subsequently centrifuged. The plasma can be stored at −20° C.

Experimental Procedure:

50 μl of the solution of the test substance and 50 μl of citrate plasma are incubated for 2 minutes at 37° C. (CL8, ball type, Bender & Hobein, Munich, FRG). 100 μl of thrombin reagent (37° C.) are subsequently added. The time that elapses until the fibrin clot forms is determined.

EXAMPLE C

Chromogenic Test for Thrombin Inhibitors

Reagents: Human Plasma Thrombin (No. T-8885, Sigma, Deisenhofen, Germany)

Substrate: H-D-Phe-Pip-Arg-pNA2HCl (S-2238, Chromogenix, Mölndahl, Sweden)

Buffer: Tris 50 mmol/l, NaCl 154 mmol/l, pH 8.0

Experimental Procedure:

The chromogenic test can be carried out in microtiter plates. 10 μl of a solution of the substance in DMSO are added to 250 μl of buffer with thrombin (final concentration 0.1 NIH units/ml) and the mixture is incubated for 5 minutes at 20 to 28° C. The test is started by adding 50 μl of the solution of the substrate in buffer (final concentration 100 μmol/l), and the mixture is incubated at 28° C. and, after 5 minutes, the reaction is stopped by adding 50 μl of citric acid (35% strength). The absorption is measured at 405/630 nm.

EXAMPLE D

Platelet Aggregation in Platelet-rich Plasma

Reagents: Human Plasma Thrombin (No. T-8885, Sigma, Deisenhofen, Germany)

Preparation of the Citrate-rich Platelet-rich Plasma:

Venous blood is collected from vena cephalica from healthy unmedicated subjects. The blood is mixed 9:1 with 0.13-molar trisodium citrate.

Platelet-rich plasma (PRP) is prepared by centrifugation at 250×g (10 minutes at room temperature). Platelet-poor plasma (PPP) is prepared by centrifugation for 20 minutes at 3600×g. PRP and PPP can be stored for 3 hours at room temperature in closed PE vessels. The platelet concentration is measured with a hematocytometer and should be between 2.5 and $2.8.10^8$/ml.

Experimental Procedure:

The platelet aggregation is measured turbidimetrically at 37° C. (PAP 4, Biodata Corporation, Horsham, PA, USA). Before thrombin is added, 215.6 μl of PRP are incubated for 3 minutes with 2.2 μl of test substance and the mixture is then stirred for 2 minutes at 1000 rpm. At a final concentration of 0.15 NIH units/ml, 2.2 μl of thrombin solution lead to the maximum aggregation effect at 37° C./1000 rpm. The inhibitory effect of the test substances is determined by comparing the rate at which thrombin aggregates (slope) without substance with the rate of thrombin with test substance at various concentrations.

We claim:

1. A compound of the formula I

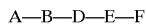

A—B—D—E—F  I in which A, B, D, E and F have the following meanings:

A:

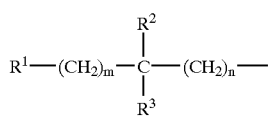

where m is 0, 1 or 2, n is 0, 1 or 2, $R^1$ is HOOC—, $C_{1-6}$-alkyl-OOC—, aryl-$C_{0-4}$-alkyl-OOC or —OH, $R^2$ is H—, $C_{1-4}$-alkyl- or $R^1$—$(CH_2)_m$— and $R^3$ is H— or $C_{1-4}$-alkyl-,

B:

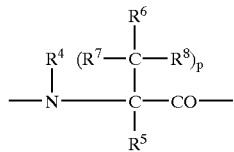

where $R^4$ is H—, $C_{1-4}$-alkyl- or $R^1$—$(CH_2)_m$—(where $R^1$ and m have the abovementioned meanings), p is 0 or 1, $R^5$ is H— or $C_{1-4}$-alkyl-, $R^6$ is H—, $C_{1-8}$-alkyl-, 2-thienyl-, 3-thienyl-, 3-indolyl-, 4-imidazolyl-, 2-pyridyl-, 3-pyridyl-, 4-pyridyl-, phenyl- which may carry up to three identical or different radicals selected from the group of $C_{1-4}$-alkyl-, $CF_3$—, $C_{1-4}$-alkoxy-, HO—, BnO—, F— and Cl—, $C_{3-8}$-cycloalkyl- which may carry up to four identical or different $C_{1-4}$-alkyl- radicals and/or where one or two C—C single bonds in the ring can be replaced by a C=C double bond and/or a phenyl ring can be fused on, $C_7$-$C_{12}$-bicycloalkyl- or $C_{10}$-tricycloalkyl- or $R^4$ and $R^6$ together are an ethylene or propylene group, $R^7$ is H, $C_{1-8}$-alkyl-, phenyl- which may carry up to three identical or different radicals from the group of $C_{1-4}$-alkyl-, $CF_3$—, $C_{1-4}$-alkoxy-, F— and Cl—, or $C_{3-8}$-cycloalkyl- which may carry up to four identical or different $C_{,4}$-alkyl radicals, and $R^8$ is H or $C_{1-4}$-alkyl,

D:

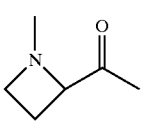

II

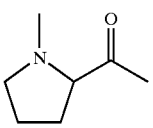

III

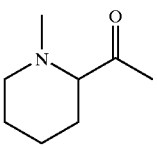

IV

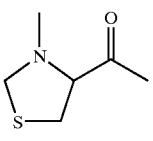

VI

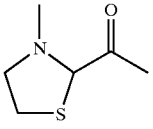

VII

-continued

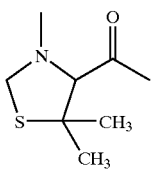

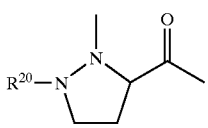

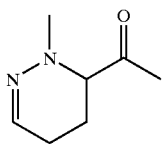

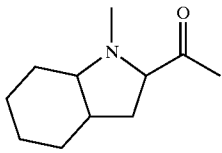

where R$^{20}$ is H, C$_{1-4}$-alkyl, Bnor BnO(CO)— and where the following applies:
if D is II, III or XI, then E has the following meaning:

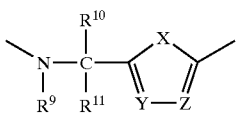

where
a) in the event that X=S, O, NH or NR$^{12}$,
  Y is —CR$^{13}$=, —CH= and
  Z is —CR=
  or
  Y is —CR$^3$= and
  Z is —CH=
  or
b) in the event that X=NR$^{12}$,
  Y is —CH= and
  Z is —CH=
  or
c) in the event that X=S, O or NH,
  Y is —CR$^{15}$= and
  Z is —N=
  or
  Y is —N= and
  Z is —CR$^{15}$=
  or
d) in the event that X=—NR$^{12}$—,
  Y is —N= and
  Z is —CR$^{16}$=, —N=
  or
  Y is —CR$^{16}$= and
  Z is —N=
and
R$^9$ is H— or C$_{1-3}$-alkyl-,
R$^{10}$ is H— or C$_{1-4}$-alkyl-,
R$^{11}$ is H— or C$_{1-4}$-alkyl-,
R$^{12}$ is CH$_3$— or C$_2$H$_5$—, VIII  R$^{13}$ is Cl—, CF$_3$— or C$_{1-4}$-alkyl-,
R$^{14}$ is Cl—, CF$_3$— or C$_{1-4}$-alkyl-,
R$^{15}$ is CF$_3$— or C$_{1-4}$-alkyl-,
R$^{16}$ is H—, CF$_3$— or C$_{1-4}$-alkyl- and
R$^{20}$ is as above,
or, if D is IV, VI, VII, VIII, IX or X, then E has the following meaning:

IX

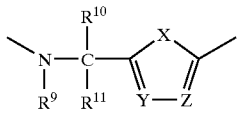

X   where
X is O, S or —NR$^{17}$—
and
Y is —N= and
Z is —CR$^{16}$= or —N=
XI  or
Y is —CR$^{16}$= and
Z is —N=
or
Y is —CR$^{18}$= and
Z is —CR$^{19}$=
and
R$^9$, R$^{10}$, R$^{11}$, R$^{16}$ and R$^{20}$ are as above,
R$^{17}$ is H, CH$_3$— or C$_2$H$_5$—,
R$^{18}$ is H—, Cl—, CF$_3$— or C$_{1-4}$-alkyl-,
R$^{19}$ is H—, Cl—, CF$_3$— or C$_{1-4}$-alkyl-,
or
if D is II, III, IV, VI, VII, VIII, IX, X or XI, E has the following meanings:

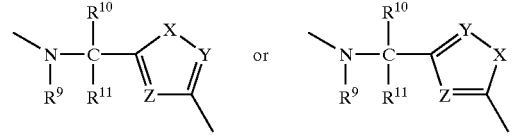

where
a) in the event that X=S,
  Y is —CR$^{18}$= and
  Z is CR$^{19}$=
  or
  Y is —CR$^{16}$= and
  Z is —N=
  or
b) in the event that X=O or —NR$^{12}$—,
  Y is —N=, —CR$^{16}$= and
  Z is —N=, —CR$^{18}$=
and
R$^9$, R$^{10}$, R$^{11}$, R$^{12}$, R$^{16}$, R$^{18}$, R$^{19}$ and R$^{20}$ have the abovementioned meanings,
F:

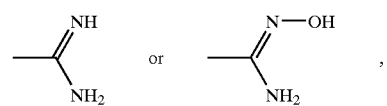

or a salt thereof with a physiologically acceptable acid.
2. A compound of the formula I as claimed in claim 1, where A to E have the following meanings:

A:

HOOC—(CH$_2$)$_t$—(t=1, 2 or 3), (HOOC—CH$_2$)$_2$—CH—,
HOOC—CH$_2$—CH(COOH)—, HOOC—CH(C$_{1-4}$-alkyl)-,
HOOC—C(C$_{1-4}$-alkyl)$_2$—,
C$_{1-6}$-alkyl-OOC—(CH$_2$)$_t$—,

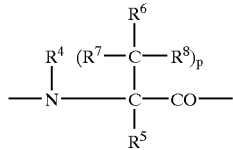

p is 0 or 1,
R$^4$ is H—, C$_{1-4}$-alkyl- or HOOC—(CH$_2$)$_m$— (m=1, 2 or 3),
R$^5$ is H—, methyl-
R$^6$ is H—, C$_{1-8}$-alkyl-, 2-thienyl-, 3-thienyl-, 3-indolyl-, 4-imidazolyl-, 2-pyridyl-, 3-pyridyl-, 4-pyridyl-, phenyl- which may carry up to three identical or different radicals from the group of CH$_3$—, CF$_3$—, CH$_3$—O—, HO—, BnO—, F— and Cl—, C$_{3-8}$-cycloalkyl, which may carry up to four methyl radicals, bicyclooctyl-, bicycloheptyl-, adamantly-, indanyl-, or decalinyl-,
R$^7$ is H, C$_{1-8}$-alkyl-, phenyl-, which may carry up to three identical or different radicals from the group of CH$_3$—, CF$_3$—, CH$_3$O—, F— or Cl—, or C$_{3-8}$-cycloalkyl- which may carry up to four methyl radicals,
R$^8$ is H, C$_{1-4}$-alkyl,

D:

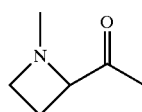 II

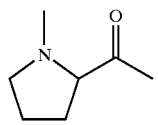 III

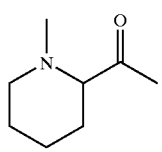 IV

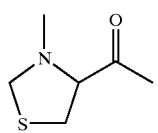 VI

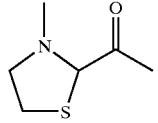 VII

-continued

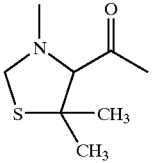 VIII

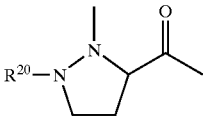 IX

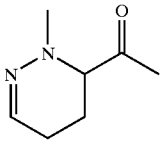 X

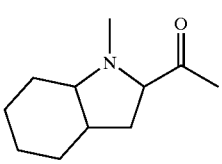 XI where R$^{20}$ is H, CH$_3$, Bn or BnO(CO)— and where the following applies:
if D is II, III or XI, then E has the meaning:

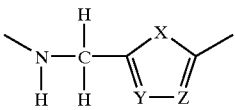

where
a) in the event that X=S, O, NH or NR$^{17}$,
Y is —CR$^{13}$= or —CH= and
Z is —CR$^{14}$=
or
Y is —CR$^{13}$= and
Z is —CH=
or
b) in the event that X=NR$^{12}$,
Y is —CH= and
Z is —CH=
or
c) in the event that X=S, O or NH,
Y is —CR$^{15}$= and
Z is —N=
or
Y is —N= and
Z is —CR$^{15}$=
or
d) in the event that X=NR$^{12}$,
Y is —N= and
Z is —CR$^{16}$— or —N=
or
Y is —CR$^{16}$= and
Z is —N=
and
R$^{12}$ is CH$_3$— or C$_2$H$_5$—,
R$^{13}$ is Cl—, CF$_3$— or C$_{1-4}$-alkyl-,
R$^{14}$ is Cl—, CF$_3$— or C$_{1-4}$-alkyl-,
R$^{15}$ is CF$_3$— or C$_{1-4}$-alkyl-, $R^{16}$ is H—, $CF_3$— or $C_{1-4}$-alkyl- and
$R^{17}$ is H, $CH_3$— or $C_2H_5$—,
$R^{20}$ is as above, or if D is IV, VI, VII, VIII, IX or X, then E has the meaning:

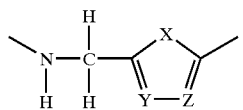

where $X$ is O, S or —$NR^{17}$— and where
$Y$ is —N= and
$Z$ is —$CR^{16}$= or —N=
or
$Y$ is —$CR^{16}$= and
$Z$ is —N=
or
$Y$ is —$CR^{18}$= and
$z$ is —$CR^{19}$=
and
$R^{16}$, $R^{17}$, and $R^{20}$ have the abovementioned meanings,
$R^{18}$ is H—, Cl—, $CF_3$— or $C_{1-4}$-alkyl-, and
$R^{19}$ is H—, Cl—, $CF_3$— or $C_{1-4}$-alkyl-,
or if D is II, III, IV, VI, VII, VIII, IX, X or XI, then E has the meanings:

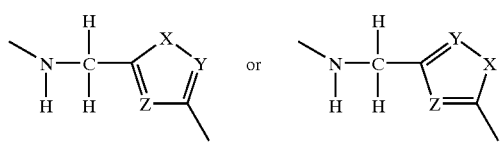

where a) in the event that X=S,
$Y$ is —$CR^{18}$= and
$Z$ is —$CR^{19}$=
or
$Y$ is —$CR^{16}$= and
$Z$ is —N=
or
b) in the event that X=O or —$NR^{12}$—,
$Y$ is —N= or —$CR^{16}$= and
$Z$ is —N= or —$CR^{18}$= and $R^{12}$, $R^{11}$, $R^{18}$, $R^{19}$ and $R^{20}$ have the abovementioned meanings,

F:

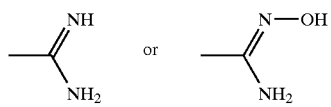

and their salts with physiologically acceptable acids.

3. A compound of the formula I as claimed in claim 1, where A, B, D, E and F have the following meanings:

A: HOOC—$CH_2$, HOOC—$CH_2$—$CH_2$, HOOC—CH($CH_3$), HOOC—CH($C_2H_5$)

B:

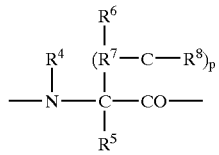

p is 0 or 1,
$R^4$ is H—, $CH_3$—
$R^5$ is H—, $CH_3$—,
$R^6$ is $C_{1-8}$-alkyl-, $C_{5-8}$-cycloalkyl- which may carry up to four methyl radicals, 2-thienyl-, 3-indolyl-, 4-imidazolyl-, 2-pyridyl-, 3-pyridyl-, 4-pyridyl, phenyl- which may carry up to three identical or different radicals from the group of $CH_3$—, $CF_3$—, $CH_3O$—, HO—, BnO—, F— and Cl—, bicyclooctyl, bicycloheptyl, adamantly, indanyl, or decalinyl,
$R^7$ is H, $CH_3$—,
$R^8$ is H, $CH_3$—,

D:

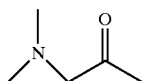  II

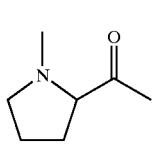  III

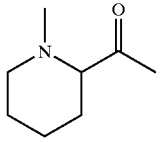  IV

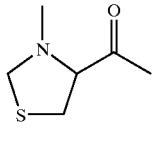  VI

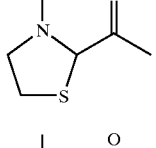  VII

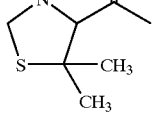  VIII

-continued

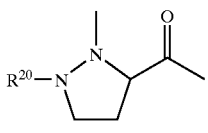

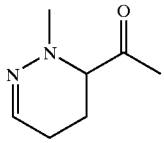

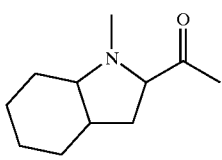

where $R^{20}$ is H, BnO(CO)— and
where the following applies:
if D is II, III or XI, then E has the meaning:

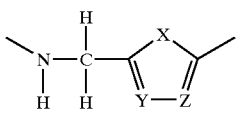

where
X is —S— and where
Y is —CH= and
Z is —CR$^3$=
or
Y is —CR$^{13}$= and
Z is —CH=
or
Y is —CR$^{15}$= and
Z is —N=
or
Y is —N= and
Z is —CR$^{15}$=
and
$R^{13}$ is Cl—, CF$_3$— or CH$_3$—
$R^{15}$ is CF$_3$— or CH$_3$— and
$R^{20}$ is as above,
or
if D is IV, VI, VII, VIII, IX or X, then E has the meaning:

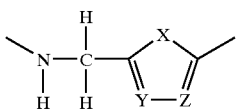

where
X is S and where
Y is —N= and
Z is —CR$^{16}$=
or
Y is —CR$^{16}$= and
Z is —N=
or
Y is —CR$^{13}$= and
Z is —CH=
or
Y is —CH= and
Z is —CR$^{13}$=
or
Y is —CH= and
Z is —CH=
and
$R^{13}$, $R^{20}$ have the abovementioned meanings,
$R^{16}$ is H—, CF$_3$— or CH$_3$—
or if D is II, III, IV, VI, VII, VIII, IX, X or XI, then E has the meanings:

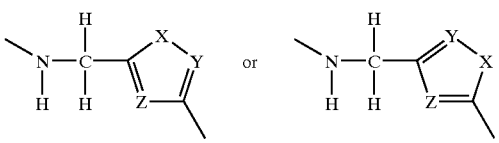

where either
a) in the event that X=S,
Y is —CH= and
Z is —CR$^{18}$=
or
Y is —CR$^{16}$= and
Z is —N=
or
Y is —CR$^{18}$= and
Z is —CH=
or
b) in the event that X=O or —NCH$_3$
Y is —CH= and
Z is —CR$^{16}$=
or
Y is —CR$^{16}$= and
Z is —CH=
or
c) in the event that X=—NR$^{12}$—
Y is —N= and
Z is —CR$^{18}$=
and
$R^{12}$ is CH$_3$— or C$_2$H$_5$— and
$R^{18}$ is H, Cl—, CF$_3$— or CH$_3$—, and
$R^{16}$, $R^{20}$ have the abovementioned meanings
F:

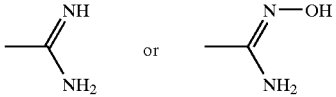

and their salts with physiologically acceptable acids.

4. A compound of the formula I as claimed in claim 1, where A, B, D, E and F have the following meanings:

A: HOOC—$CH_2$, HOOC—$CH_2$—$CH_2$, HOOC—CH($CH_3$), HOOC—CH($C_2H_5$)

B:

[structure showing: —N($R^4$)—C($R^7$—C($R^6$)—$R^8$)$_p$—C($R^5$)—CO—]

p is 0 or 1,
$R^4$ is H—,
$R^5$ is H—,
$R^6$ is $C_{1-8}$-alkyl-, 2-thienyl-, 3-indolyl-, 4-imidazolyl-, 2-pyridyl-, 3-pyridyl-, 4-pyridyl-, $C_{5-8}$-cycloalkyl- which may carry up to four methyl radicals, phenyl- which may carry up to three identical or different radicals from the group of $CH_3$—, $CF_3$—, $CH_3O$—, HO—, BnO—, F—and Cl—, bicyclooctyl, bicycloheptyl, adamantly, indanyl, or decalinyl,
$R^7$ is H,
$R^8$ is H,

D:

II [azetidinyl ketone structure]

III [pyrrolidinyl ketone structure]

IV [piperidinyl ketone structure]

VI [thiazolidin-4-yl ketone structure]

VII [thiazolidin-2-yl ketone structure]

VIII [dimethyl-thiazolidinyl ketone structure]

IX [pyrazolidinyl ketone structure with $R^{20}$]

X [tetrahydropyridazinyl ketone structure]

XI [octahydroindolyl ketone structure]

where the following applies:
if D is II, III or XI, then E has the meaning:

[structure: —N(H)(CH)—C(H)(H)—X=Y—Z with methyl]

where
X is S and
Y is —$CR^{13}$= and
Z is —CH=
or
is —CH= and
Z is —$CR^{13}$=
or
Y is —$CR^{15}$= and
Z is —N=
or
Y is —N= and
Z is —$CR^{15}$=
and
$R^{13}$ is Cl—, $CF_3$— or $CH_3$— and
$R^{15}$ is $CF_3$— or $CH_3$—,
or
if D is IV, VI, VII, VIII, IX or X, then E has the meaning:

[structure: —N(H)(CH)—C(H)(H)—X=Y—Z with methyl]

where
X is S and
Y is —N= and
Z is —$CR^{16}$=
or
Y is —$CR^{16}$= and
Z is —N=
or Y is —CH= and
Z is —CR¹³=
or
Y is —CR¹³= and
Z is —CH=
or
Y is —CH= and
Z is —CH=
and
R¹³ has the abovementioned meaning and
R¹⁶ is H—, CF₃— or CH₃—, or
if D is II, III, IV, VI, VII, VIII, IX, X or XI, then E has the meanings:

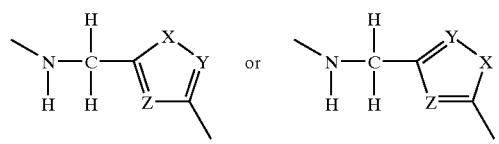

where
a) in the event that X=S,
Y is —CH= and
Z is —CR¹⁸=
or
Y is —CR¹⁸= and
Z is —CH=
or
Y is —CR¹⁶= and
Z is —N=
or
b) in the event that X=O or —NCH₃
Y is —CH= and
Z is —CR¹⁶=
or
Y is —CR¹⁶= and
Z is —CH=
or
c) in the event that X=NCH₃
Y is —N= and
Z is —CR¹⁶=
and
R¹⁶ has the abovementioned meaning and
R¹⁸ is H, Cl—, CF₃— or CH₃—,
F:

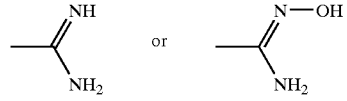

and their salts with physiologically acceptable acids.

5. A compound which contains the structural element

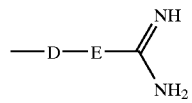

where D and E have the meanings given in any of claims 1 to 4 and where a hydrogen atom, a protective group, an unsubstituted or substituted natural or unnatural amino acid, an unsubstituted or substituted carboxylic acid or an unsubstituted or substituted alkyl radical is located on the nitrogen atom of building block D.

6. A compound which contains the structural element

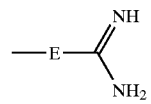

where E has the meaning given in any of claims 1 to 4 and where a hydrogen atom, a protective group, an unsubstituted or substituted natural or unnatural amino acid, an unsubstituted or substituted carboxylic acid or an unsubstituted or substituted alkyl radical is located on the nitrogen atom of NR⁹.

7. A compound containing a structural element of the formula

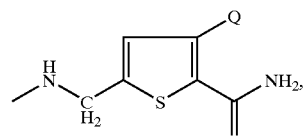

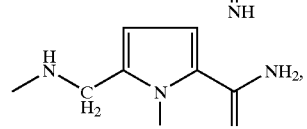

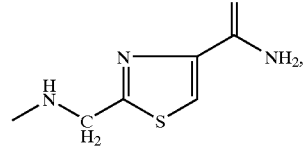

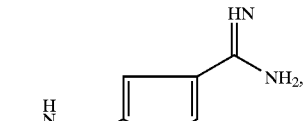

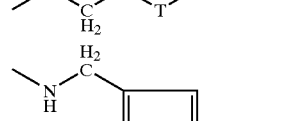

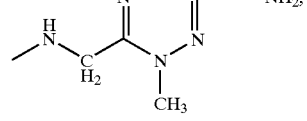

where Q is CH₃ or Cl, T is NCH₃, O or S and W is NCH₃ or S.

8. A compound of the formula Va or Vb

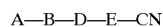   Va,

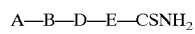   Vb, where A, B, D and E have the meanings given in claim 1.

9. A drug comprising, in addition to drug adjuvants and/or excipients, a compound as defined in claim 1 and a compound which contains the structural element

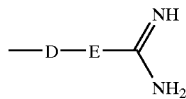

where D and E have the meanings given in claim 1.

10. A process for combating a disease selected from the group consisting of deep vein thrombones, pulmonary embolisms, myocardial or cerebral infarcts, unstable angina, disseminated intravascular coagulation, lengthened renerfusion time and shortened reocclusion time in a patient in need thereof which comprises treating the patient with an effective amount of a drug as defined in claim 1.

11. A method for reducing coagulation in extracorporeal circulation, comprising coating an artificial surface or a tubing system or line of a machine used for this purpose with a compound of the formula I as claimed in claim 1.

12. A process for inhibiting thrombin in a patient in need of such treatment, comprising introducing an effective amount of a compound as defined in claim 1 such that the compound interacts with and inhibits the activity of thrombin.

13. A process for combating an inflammatory disease selected from the group consisting of asthma, pancreatitis, rhinitis, arthritis and urticaria in a pateient in need thereof which comprises treating the patient with an effective amount of a compound of claim 1 and a compound which contains the structural element

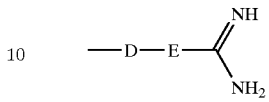

where D and E have the meanings given in claim 1 and where a hydrogen atom, a protective group, an unsubstituted or substituted amino acid, an unsubstituted or substituted carboxylic acid or an unsubstituted or substituted alkyl radical is located on the nitrogen atom of building block D.

14. A process for producing drugs which are suitable as thrombin inhibitors, comprising combining a compound as claimed in claim 1 with drug adjuvants and/or excipients.

* * * * *